United States Patent
Isaka et al.

(10) Patent No.: US 10,495,602 B2
(45) Date of Patent: Dec. 3, 2019

(54) GAS SENSOR MANUFACTURING METHOD AND GAS SENSOR MANUFACTURING APPARATUS

(71) Applicant: NGK INSULATORS, LTD., Nagoya (JP)

(72) Inventors: Kenji Isaka, Nagoya (JP); Koji Egawa, Nagoya (JP); Nobukazu Ikoma, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 180 days.

(21) Appl. No.: 15/464,740

(22) Filed: Mar. 21, 2017

(65) Prior Publication Data
US 2017/0276638 A1 Sep. 28, 2017

(30) Foreign Application Priority Data

Mar. 25, 2016 (JP) ................................ 2016-061512

(51) Int. Cl.
*G01N 27/407* (2006.01)
*G01N 27/406* (2006.01)
(Continued)

(52) U.S. Cl.
CPC ..... *G01N 27/4078* (2013.01); *G01N 27/4067* (2013.01); *G01N 33/0037* (2013.01);
(Continued)

(58) Field of Classification Search
CPC ........... G01N 27/4062; G01N 27/4067; G01N 27/407; G01N 27/4078; G01N 27/409;
(Continued)

(56) References Cited

U.S. PATENT DOCUMENTS 9,188,576 B2 * 11/2015 Hirata ................ G01N 33/0009
9,335,312 B2 * 5/2016 Kato .................. G01N 27/4078
(Continued)

FOREIGN PATENT DOCUMENTS

EP 2 730 917 A1 5/2014
EP 2 784 498 A1 10/2014
(Continued)

OTHER PUBLICATIONS

U.S. Appl. No. 15/464,710, filed Mar. 21, 2017, Kenji Isaka.
Partial European Search Report, European Application No. 17162909.0, dated Jul. 27, 2017 (14 pages).

*Primary Examiner* — Peter Dungba Vo
*Assistant Examiner* — Joshua D Anderson
(74) *Attorney, Agent, or Firm* — Burr & Brown, PLLC

(57) ABSTRACT

Provided is a method for manufacturing a gas sensor which suppresses a defective product caused by a defective posture of a sensor element therein. The method includes a step of obtaining an assembled body constituting the gas sensor, including steps of: causing one end of the sensor element to come to abut to a positioning member for positioning the sensor element; and applying a first force to the annularly-mounted members including a powder compact annularly mounted to the sensor element under a state that the sensor element is positioned and thereby compressing the powder compact so as to fix the sensor element inside of the tubular body, and the compression is performed while constraining the sensor element in a predetermined constraining region in the other end side of the sensor element.

34 Claims, 38 Drawing Sheets

(51) Int. Cl.
 *G01N 33/00* (2006.01)
 *G01N 27/417* (2006.01)

(52) U.S. Cl.
 CPC ..... *G01N 27/4175* (2013.01); *Y10T 29/49829* (2015.01); *Y10T 29/49934* (2015.01); *Y10T 29/53187* (2015.01)

(58) Field of Classification Search
 CPC ........... G01N 27/4175; G01N 33/0009; G01N 33/0037; Y10T 29/49002; Y10T 29/49007; Y10T 29/49126; Y10T 29/49826; Y10T 29/49828; Y10T 29/49829; Y10T 29/49904; Y10T 29/49934; Y10T 29/5313; Y10T 29/53187; Y10T 29/53265
 USPC ........... 703/23.2, 23.31, 31.05; 204/424–431
 See application file for complete search history.

(56) References Cited

U.S. PATENT DOCUMENTS

| | | | |
|---|---|---|---|
| 9,423,368 | B2* | 8/2016 | Makino .................. G01N 27/12 |
| 2005/0022361 | A1 | 2/2005 | Matsuo et al. |
| 2015/0253298 | A1 | 9/2015 | Isaka et al. |
| 2016/0273944 | A1* | 9/2016 | Hattori ............... G01N 27/4078 |
| 2018/0281331 | A1* | 10/2018 | Isaka ........................ B30B 9/00 |

FOREIGN PATENT DOCUMENTS

| | | |
|---|---|---|
| EP | 3 093 655 A1 | 11/2016 |
| JP | 2005-037372 A | 2/2005 |
| JP | 2008-145339 A | 6/2008 |
| JP | 2015-169606 A1 | 9/2015 |

* cited by examiner

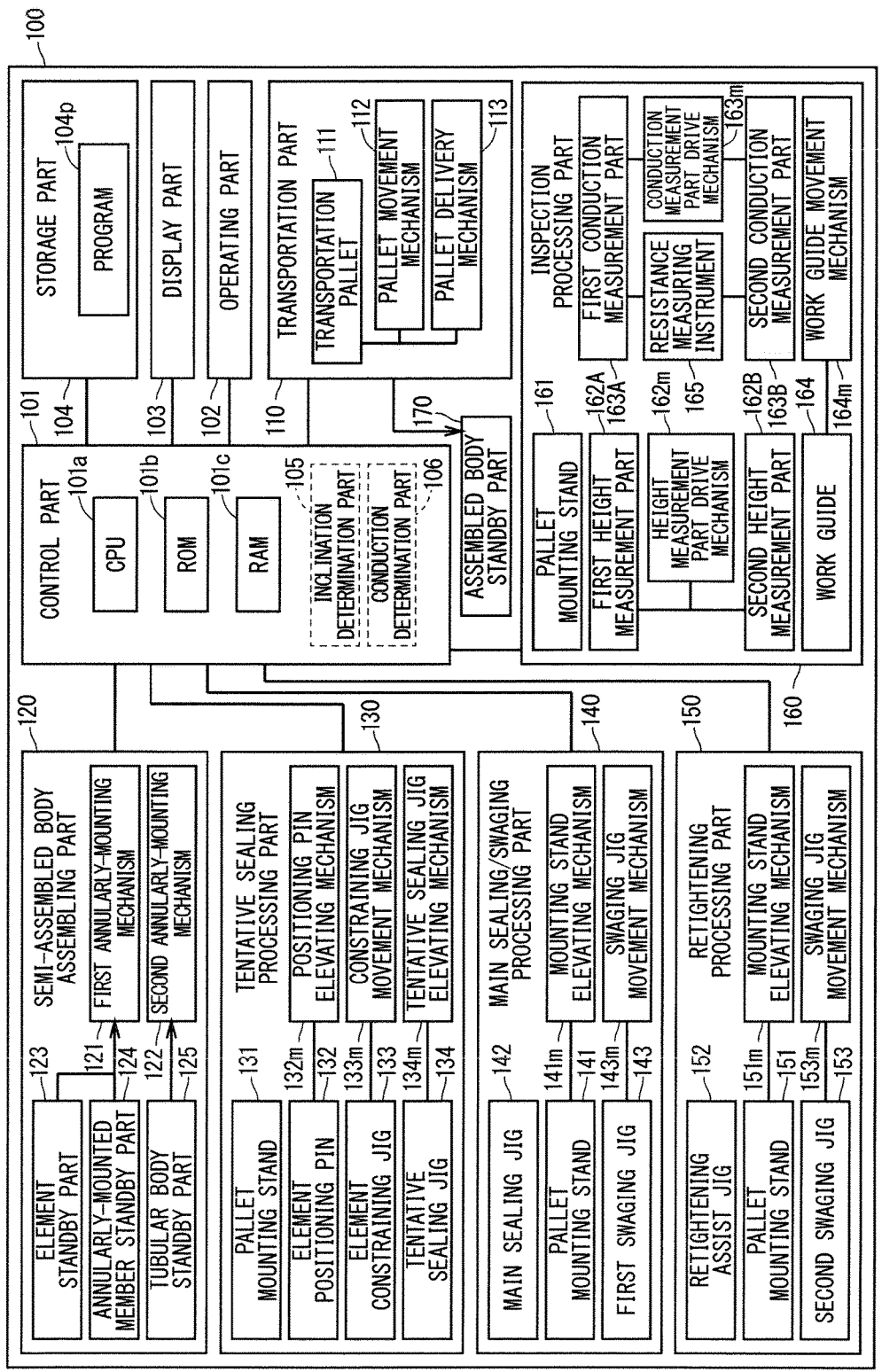
F I G. 6

F I G. 1 5
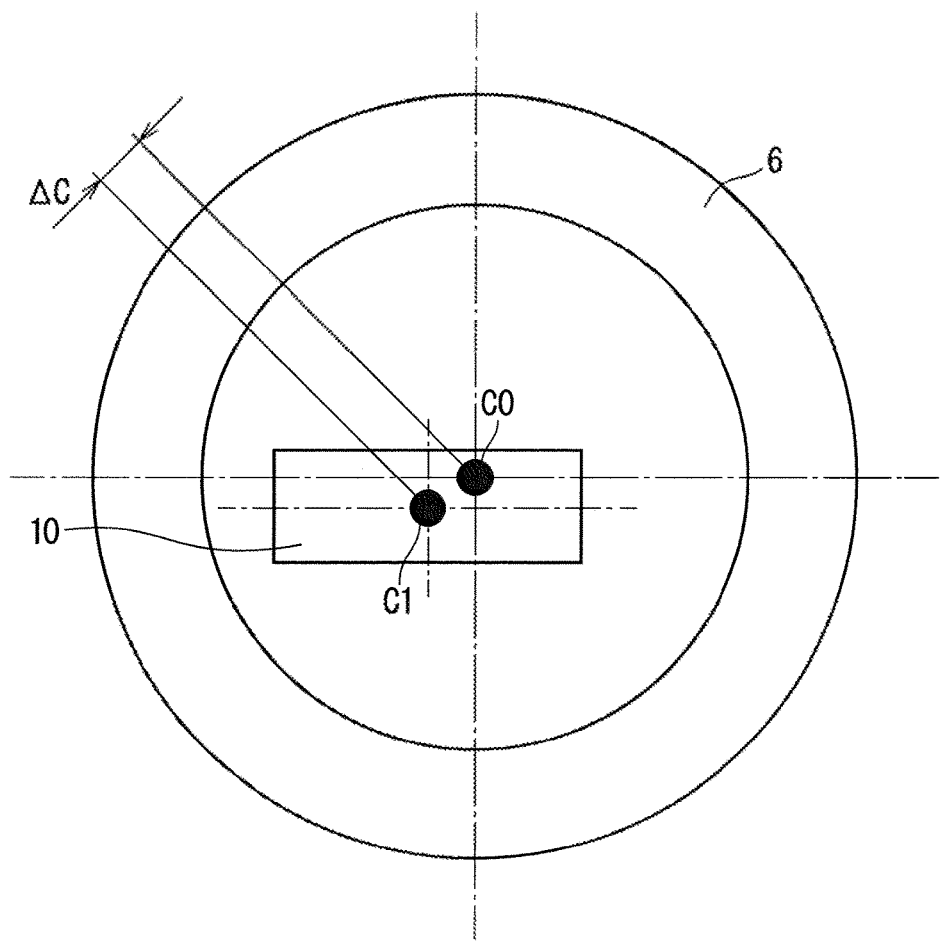

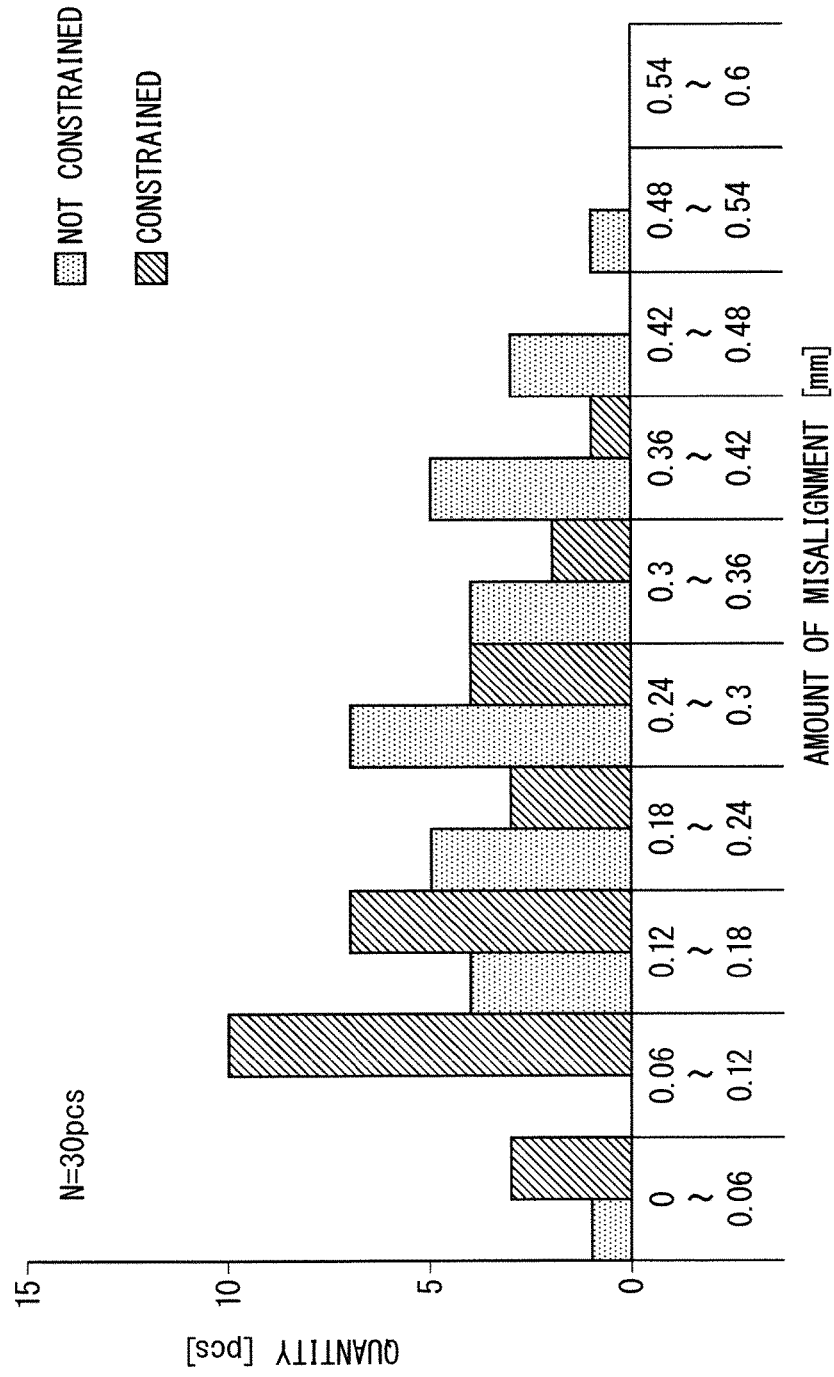

F I G. 1 8
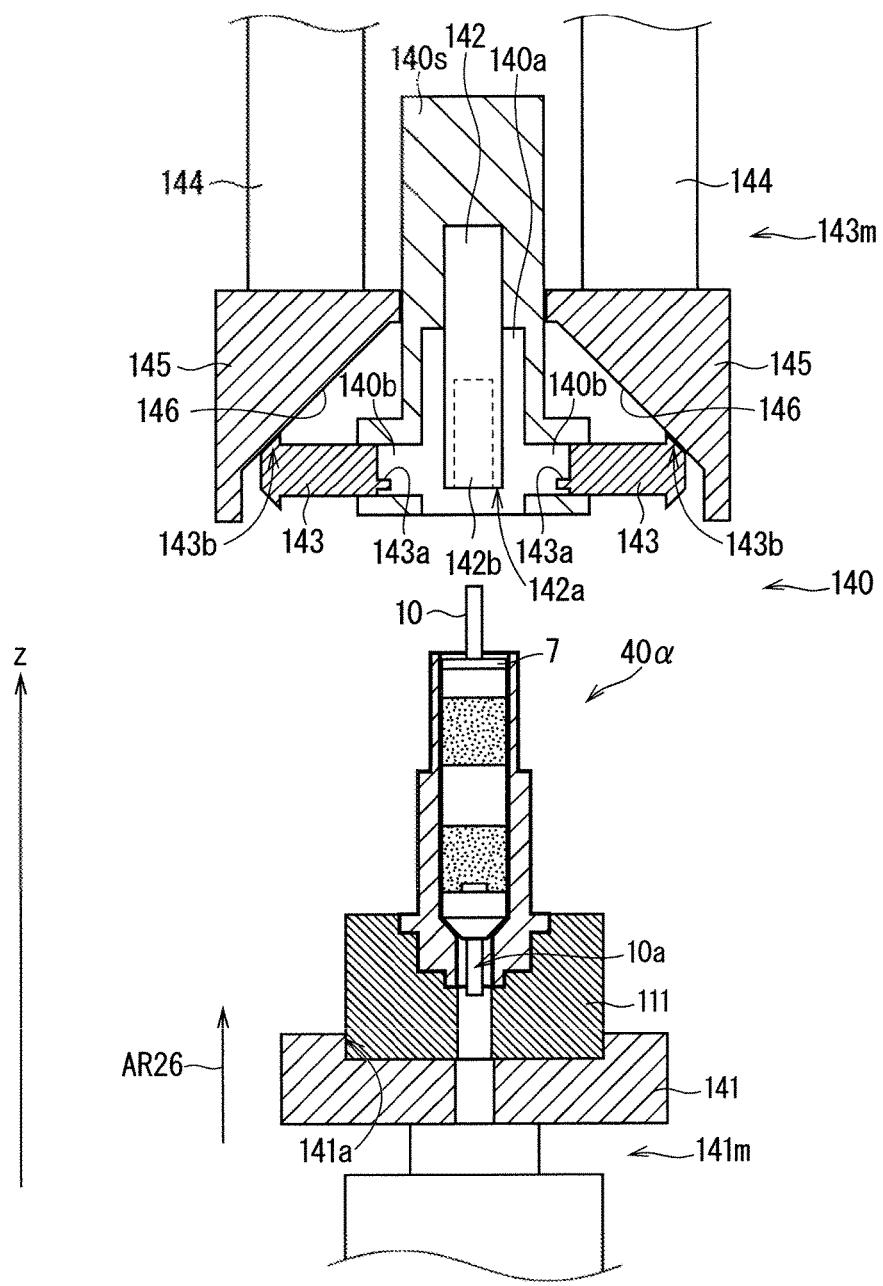

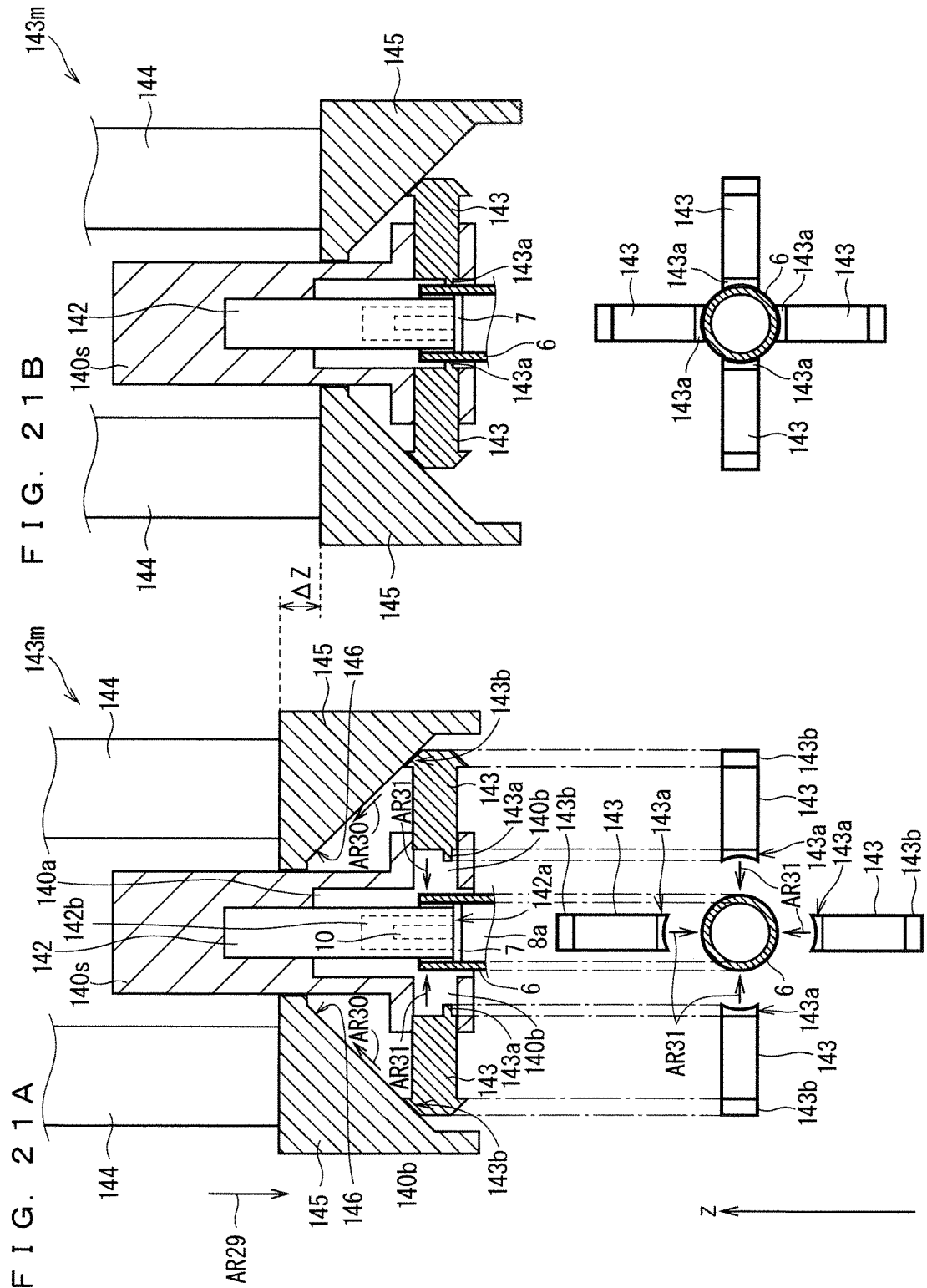

F I G. 2 2
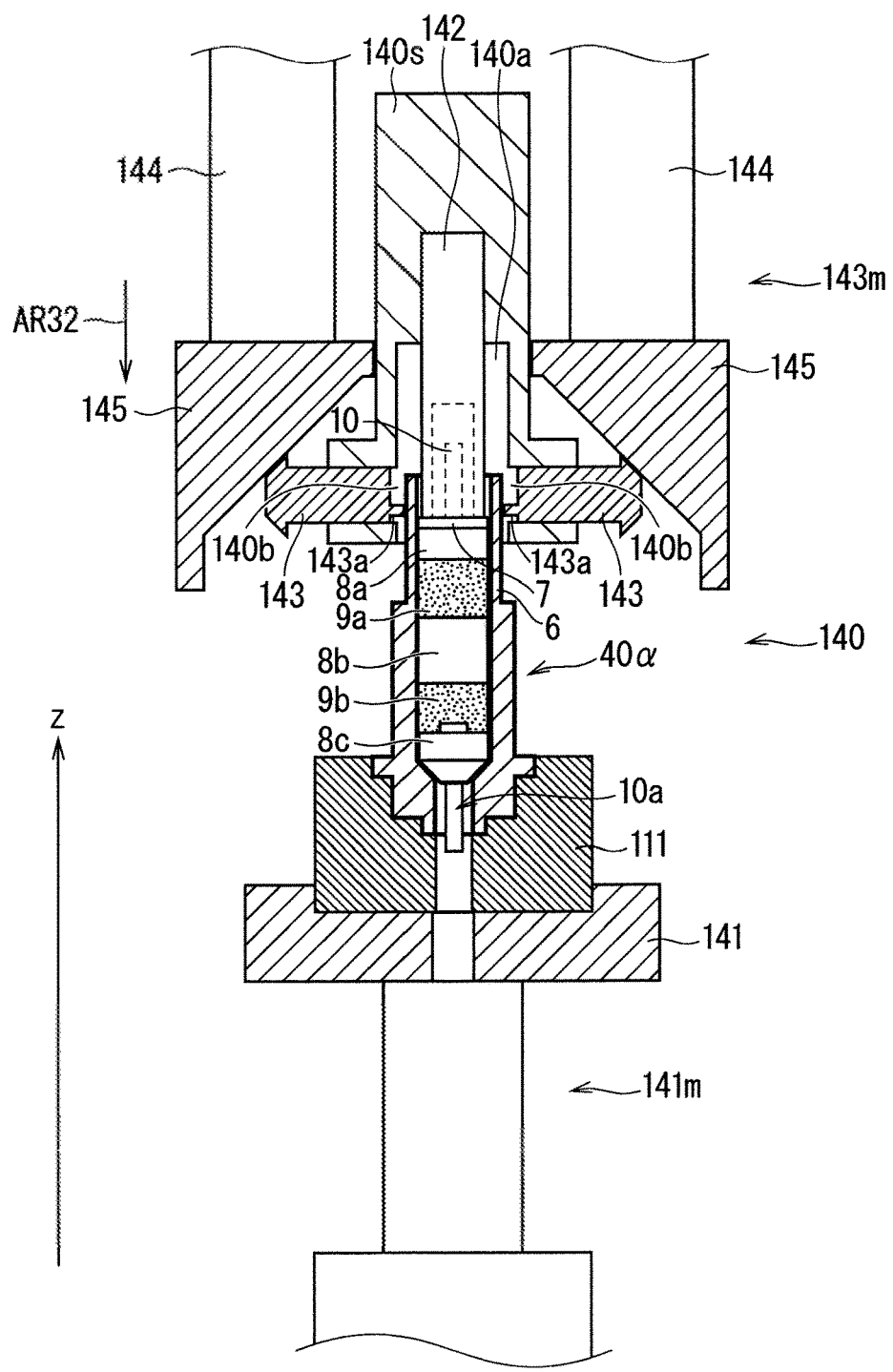

F I G. 2 3
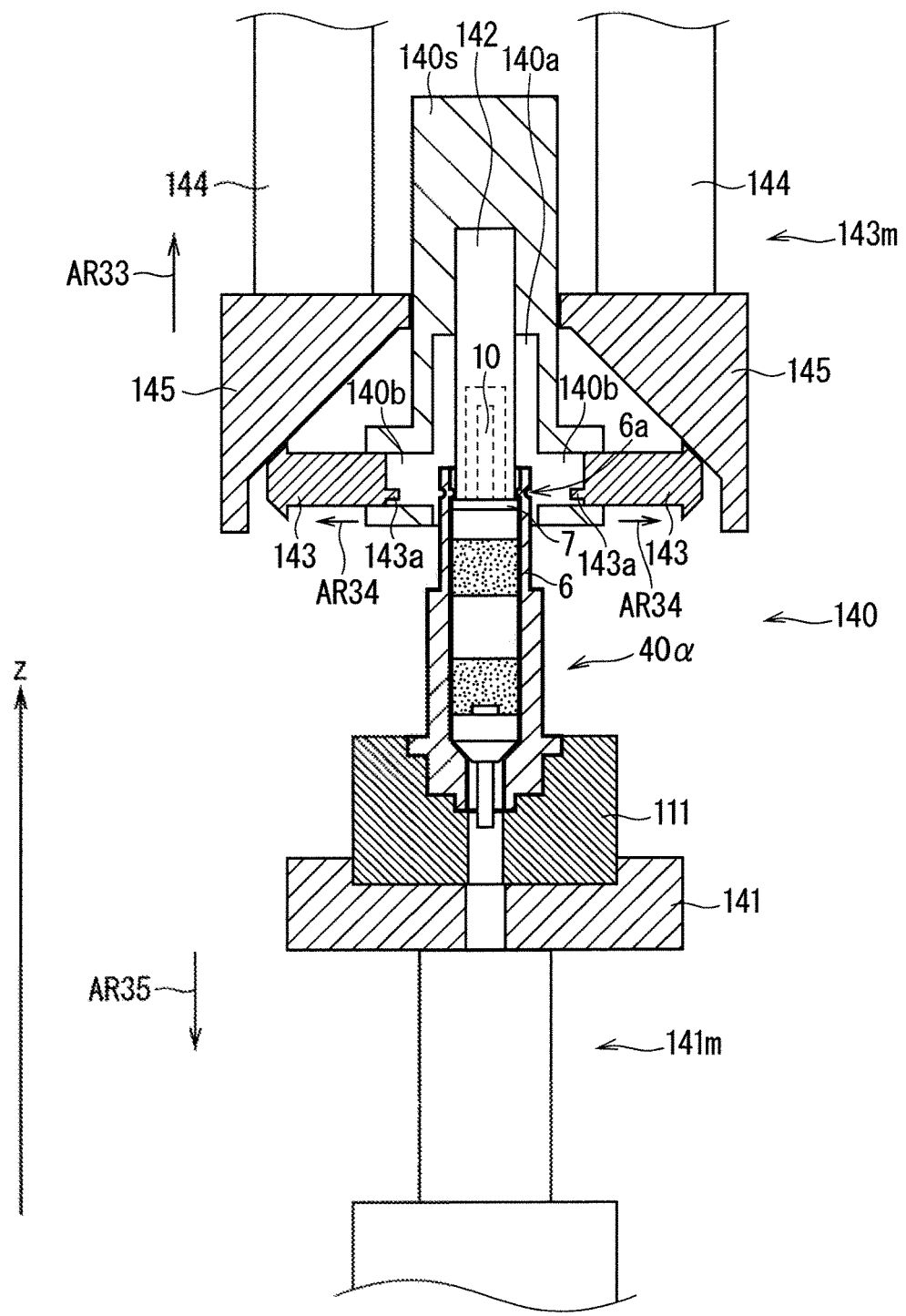

FIG. 24
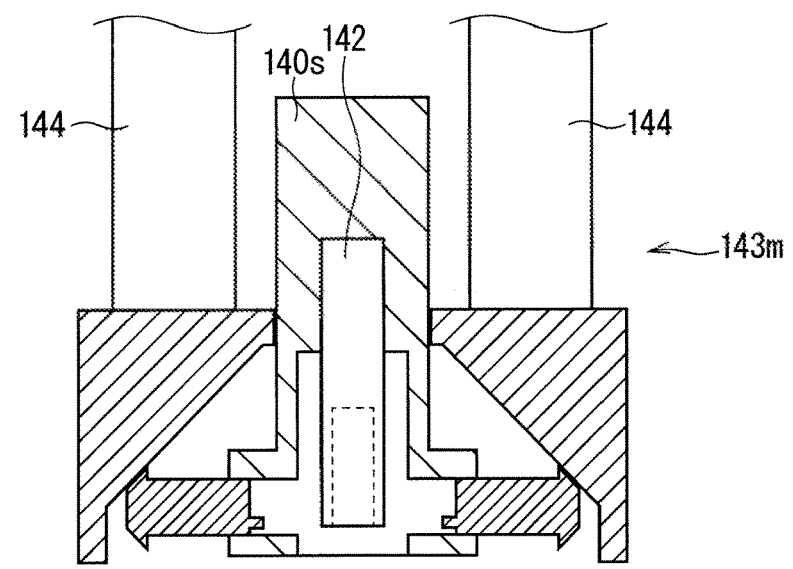
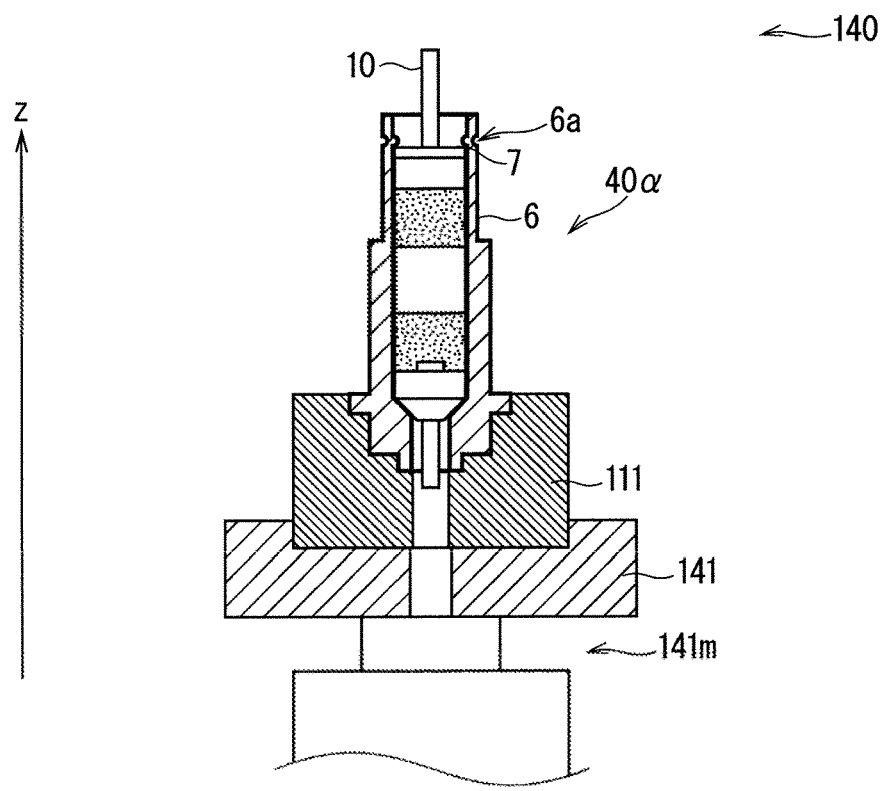

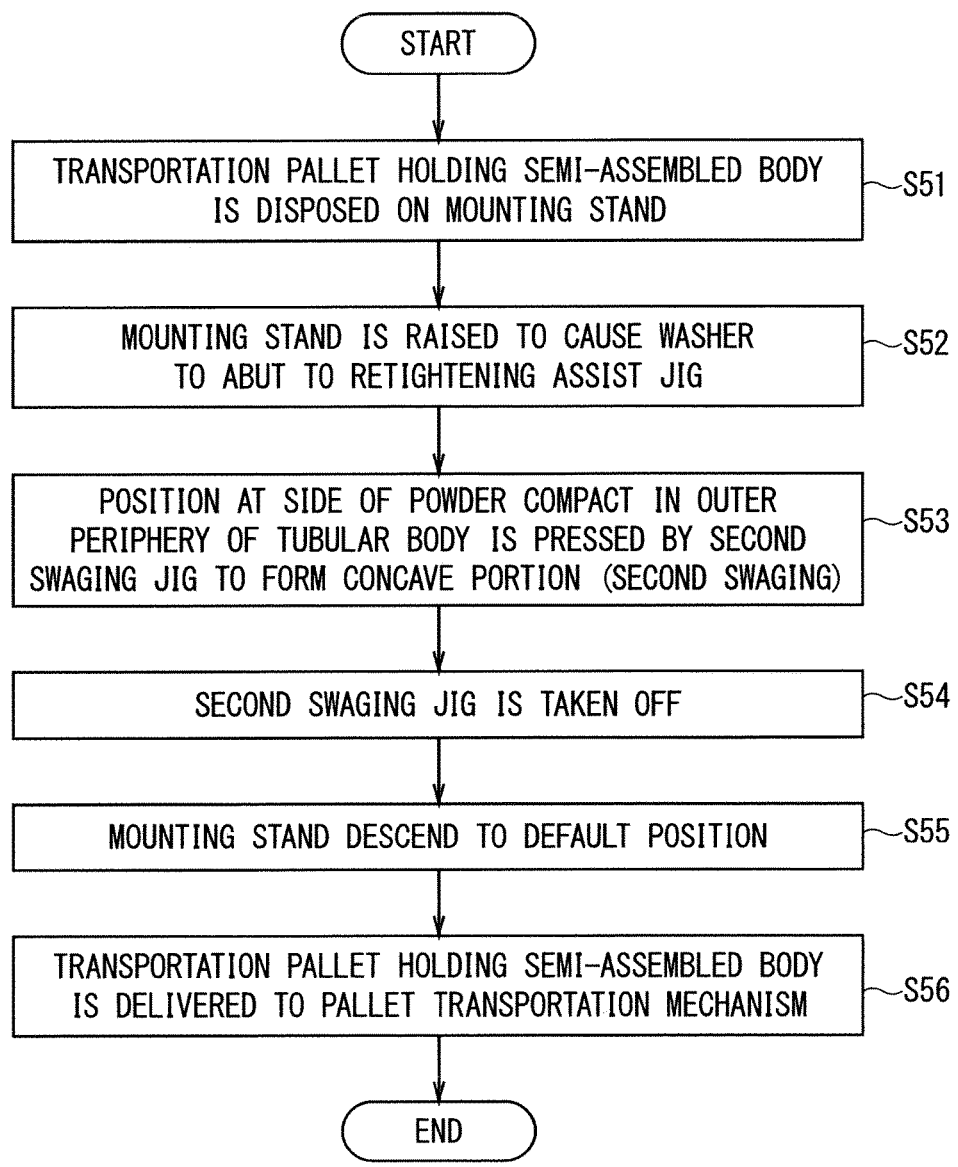
F I G. 2 5

F I G. 2 7
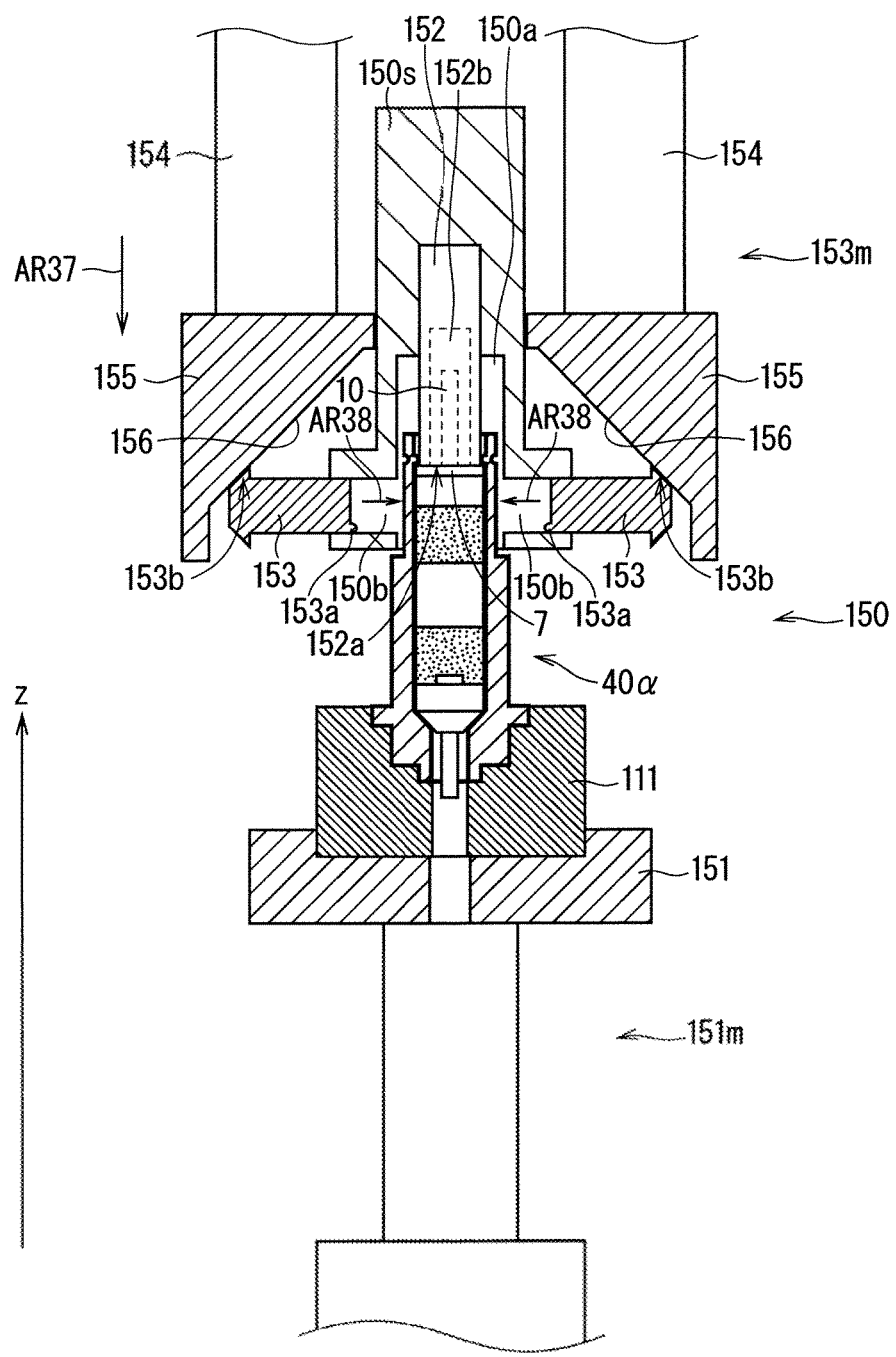

F I G. 3 2
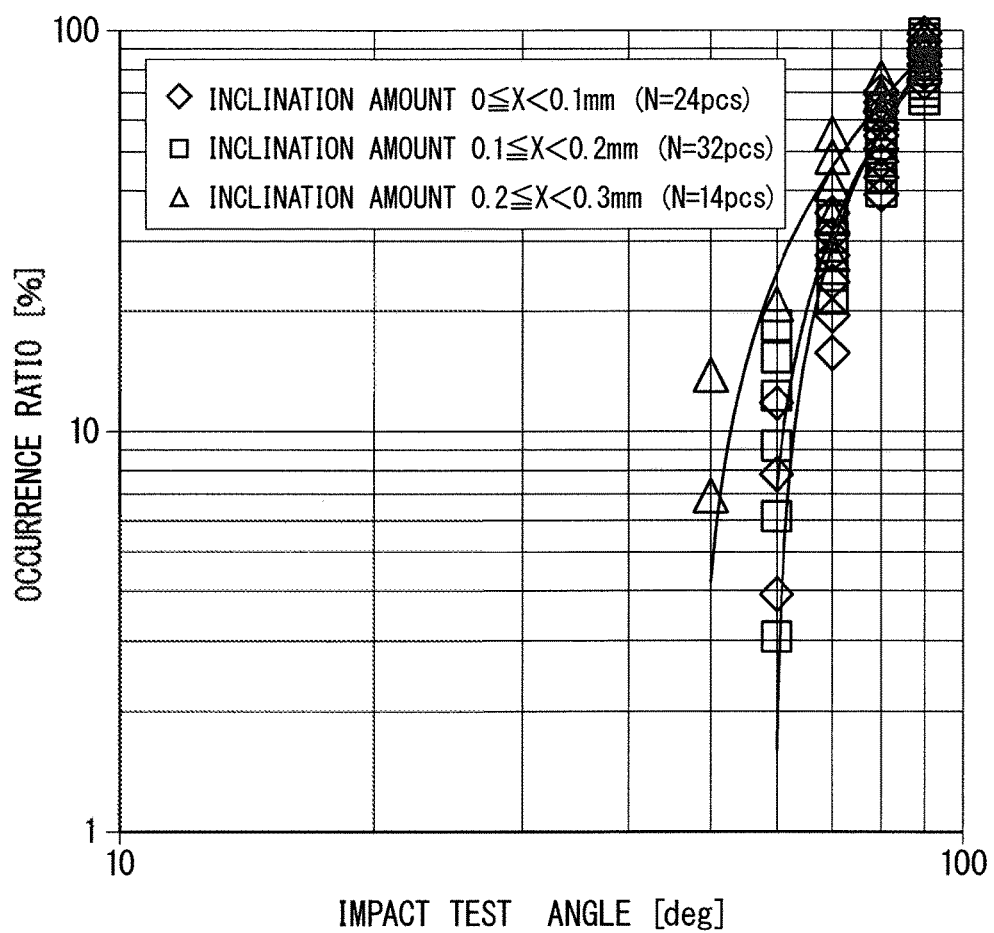

GAS SENSOR MANUFACTURING METHOD AND GAS SENSOR MANUFACTURING APPARATUS

BACKGROUND OF THE INVENTION

Field of the Invention

The present invention relates to a method for manufacturing a gas sensor including a ceramic sensor element.

Description of the Background Art

Conventionally, there have been well known gas sensors having sensor elements formed from an oxygen-ion conductive solid electrolyte ceramic, such as zirconia (ZrO2), as devices for determining the concentrations of predetermined gas components in measurement gas, such as combustion gasses and exhaust gasses in internal combustion engines such as automobile engines.

Such gas sensors generally include a sensor element (detection element) with an elongated plate shape which is made of a ceramic, wherein the sensor element is secured by a plurality of ceramic supporters which are ceramic insulators and by powder compacts made of ceramics such as talc which are embedded between the ceramic supporters, in a hollow portion of a metal housing and a cylindrical inner tube secured thereto through welding, so that the powder compacts provide hermetic sealing between a space on one end side of the sensor element and a space on the other end side of the sensor element. The hermetic sealing is achieved by pressing the ceramic supporters and the powder compacts which are sequentially and annularly mounted to the sensor element using a predetermined sealing jig to compress the powder compacts, and subsequently swaging the inner tube from outside using a predetermined swaging jig (refer to Japanese Patent Application Laid-Open No. 2015-169606, for example).

In order to secure airtightness with the hermetic sealing described above, a pressing by a sealing jig needs to be performed with a relatively high load of 400 kgf or more, for example. In addition, the sensor element needs to be disposed in a correct position in a correct attitude after the hermetic sealing so that the gas sensor satisfies desired characteristics.

If the sensor element is inclined and comes in contact with the ceramic supporters at the time of the sealing, thereby being subjected to an action of a stress from the ceramic supporters, a crack may occur in a portion of the sensor element being in contact with the ceramic supporters in a process of manufacture or in use, or the sensor element may be broken at the contact portion. In a manufacturing process, it is required that a generation of such a defective product is reduced and, if the defective product is generated, it needs to be reliably found and excluded from a shipping object.

SUMMARY OF THE INVENTION

The present invention relates to a method for manufacturing a gas sensor including a ceramic sensor element and, more particularly, is directed to a suppression of breakage failure of the element at a time of assembly.

According to the present invention, a method for manufacturing a gas sensor, the method including a step of obtaining an assembled body constituting the gas sensor by performing a predetermined processing on a semi-assembled body which is manufactured in advance, and the semi-assembled body includes: an annular-mounted assembly in which a plurality of annularly-mounted members, at least one of which is a ceramic powder compact, each having a disc shape or cylindrical shape are annularly mounted to a sensor element with an elongated plate shape which is mainly made of a ceramic; and a tubular body which is annularly mounted to an outer periphery of the annularly-mounted members and capable of engaging one end side of the annularly-mounted members therein. The step of obtaining the assembled body includes steps of: a) causing one end of the sensor element constituting the semi-assembled body to abut to a predetermined positioning member for positioning the sensor element; and b) applying a first force to the annularly-mounted members from the other end side of the sensor element having been positioned through the step a) and thereby compressing the powder compact so as to fix the sensor element inside of the tubular body, wherein the step b) is performed while constraining the sensor element in a predetermined constraining region in the other end side of the sensor element.

According to the present invention, an occurrence of a breakage failure of the element inside the assembled body, which constitutes the main body of the gas sensor, can be appropriately suppressed, so that a generation of a defective product in the gas sensor is suppressed.

Preferably, in the method for manufacturing the gas sensor of the present invention, the step of obtaining the assembled body further includes a step of: c) after the step b), applying a second force which is larger than the first force to the annularly-mounted members from the other end side of the sensor element with the one end of the sensor element not abutting to the positioning member and thereby further compressing the powder compact so as to hermetically seal between spaces located on one end side and the other end side of the sensor element inside of the tubular body.

In this case, the second compression for the hermetic sealing between the spaces located on one end side and the other end side of the sensor element inside of the tubular body is successively performed subsequent to the first compression performed mainly for purpose of positioning the sensor element, without using the element positioning member, so that the hermetic sealing can be achieved without a chip or break in the sensor element.

Alternatively, preferably, in the method for manufacturing the gas sensor of the present invention, the annularly-mounted members include a washer, and the method further includes steps of: f) obtaining an inclination amount of the washer in a state where the assembled body is in the assembly posture; and g) determining that the assembled body is a defective product when the inclination amount exceeds a predetermined threshold value.

In this case, the usage of the assembled body having the breakage failure of the element due to the washer inclination or holding a potential of it in the future, to the gas sensor can be appropriately prevented.

Accordingly, the object of the present invention is to provide a method for manufacturing a gas sensor which suppresses a generation of a defective product caused by an improper posture of the sensor element inside the gas sensor.

BRIEF DESCRIPTION OF THE DRAWINGS

FIG. 6 is a block diagram schematically illustrating a structure of a manufacturing apparatus 100.

FIG. 15 is a view describing how to evaluate a misalignment of the sensor element 10 in the assembled body 40.

FIG. 16 is a view exemplifying an effect of the element constraining jig 133.

FIG. 18 is a side view schematically illustrating a structure of a main sealing/swaging processing part 140.

FIGS. 21A and 21B are views for describing an operation of a swaging jig movement mechanism 143m at the time of the first swaging.

FIG. 22 is a view illustrating a state halfway through the first swaging process in stages.

FIG. 23 is a view illustrating a state halfway through the first swaging process in stages.

FIG. 24 is a view illustrating a state halfway through the first swaging process in stages.

FIG. 25 is a view illustrating a more specific procedure of a second swaging process.

FIG. 27 is a view illustrating a state halfway through the second swaging process in stages.

FIG. 32 is a view exemplifying a result of an impact test performed using the impact test apparatus 1000.

DESCRIPTION OF THE PREFERRED EMBODIMENTS

<Configuration of Gas Sensor>

Figure 1:
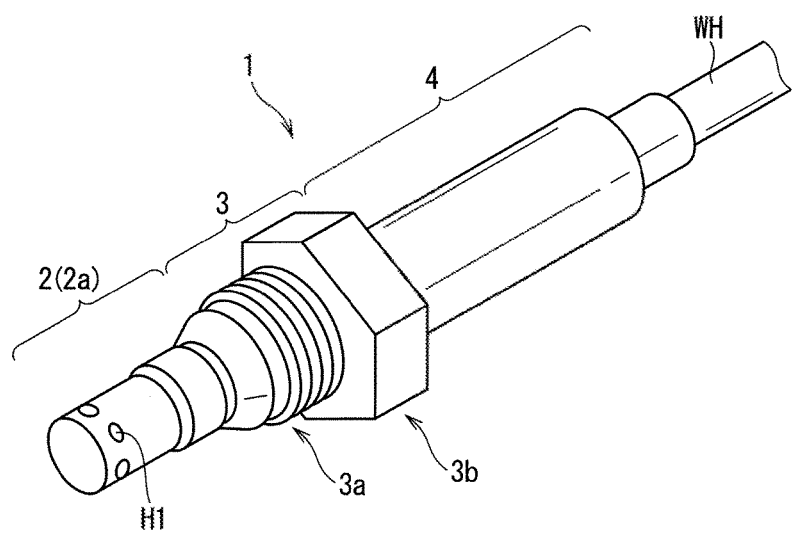
FIG. 1 is a perspective view of an external appearance of a gas sensor 1.
Figure 2:
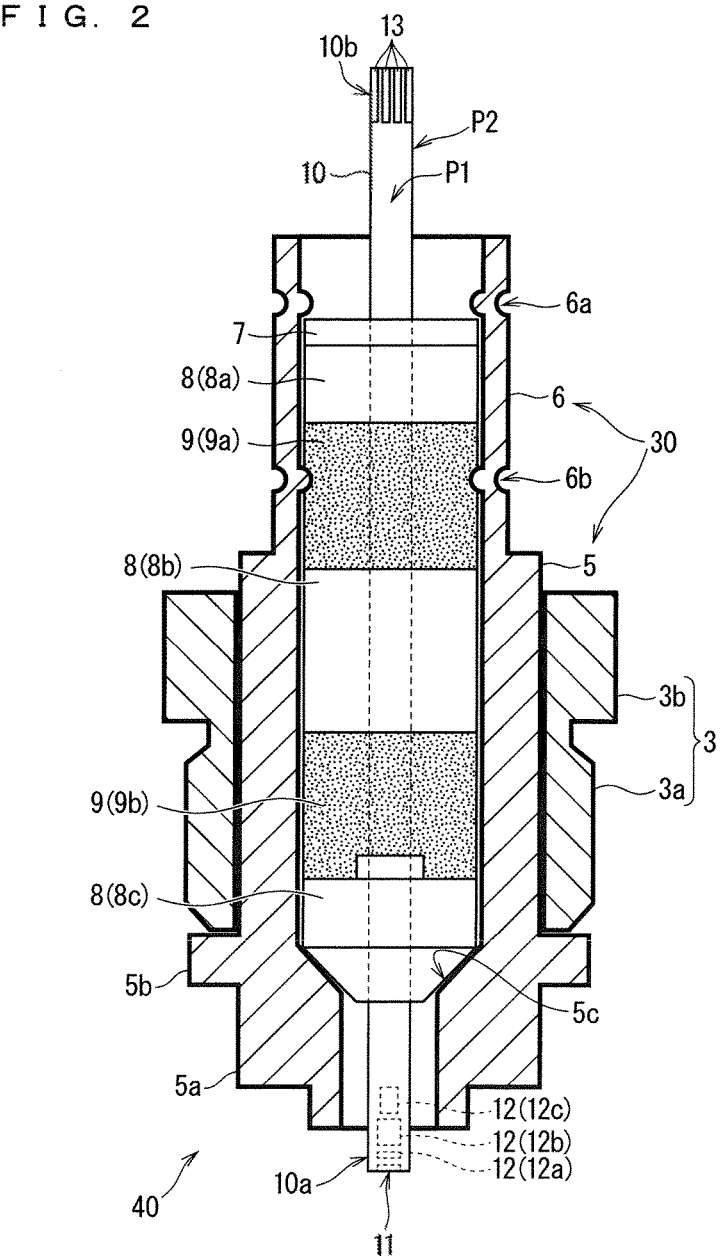
FIG. 2 is a partial cross-sectional view illustrating a main structure inside the gas sensor 1.

FIG. 1 is an external perspective view of a gas sensor (more specifically, its main body) 1 to be manufactured in this preferred embodiment. FIG. 2 is a partial cross-sectional view illustrating a main structure inside the gas sensor 1. In this preferred embodiment, the gas sensor 1 serves to detect a predetermined gas component (such as NOx) with a sensor element 10 (FIG. 2) included therein.

The sensor element 10 is an elongated columnar or thin-plate like member including, as a main constituent material, an oxygen-ion conductive solid electrolyte ceramic such as zirconia. The sensor element 10 has a configuration in which a gas inlet, an internal space, and the like are provided on a first tip portion 10a side and various electrodes and wiring patterns are provided on a surface and inside of an element body. In the sensor element 10, a detection gas introduced into the internal space is reduced or decomposed in the internal space, to thereby generate oxygen ions. The gas sensor 1 determines the concentration of the gas component based on a fact that an amount of oxygen ions flowing inside an element is proportional to the concentration of the gas component in the detection gas. A surface facing a front in FIG. 2 is referred to as a main surface P1 of the sensor element 10, and a surface that is perpendicular to the main surface P1 and extends along a longitudinal direction is referred to as a side surface P2. Both the main surface P1 and the side surface P2 extend in the longitudinal direction of the sensor element 10, and a width of the main surface P1 is larger than that of the side surface P2.

The outside of the gas sensor 1 is mainly formed of a first cover 2, a fixing bolt 3, and a second cover 4.

The first cover 2 is an approximately cylindrical exterior member that protects a portion of the sensor element 10 that comes in direct contact with the detection gas in use, which is specifically the first tip portion 10a including a gas inlet 11 and a closed space 12 (buffer space 12a, first internal space 12b, and second internal space 12c) and the like. The gas inlet 11 is open at the first tip portion 10a, which is the lowermost end of the sensor element 10 in FIG. 2. Each of the buffer space 12a, first internal space 12b, and second internal space 12c is provided inside the sensor element 10. The gas inlet 11, the buffer space 12a, the first internal space 12b, and the second internal space 12c are arranged in this order along the longitudinal direction of the sensor element 10 and are communicated with each other via a diffusion-controlling part.

More specifically, the first cover 2 has a double-layer structure of an outside cover 2a and an inside cover (not shown). Each of the outside cover 2a and inside cover has a circular bottom on one side and has a plurality of through holes through which a gas passes in its side surface. FIG. 1 exemplifies through holes HI provided in the outside cover 2a, which are merely an example. A position and number of through holes arranged may be appropriately determined in consideration of how a measurement gas flows into the first cover 2.

The fixing bolt 3 is an annular member to be used when the gas sensor 1 is fixed at a measurement position. The fixing bolt 3 includes a threaded bolt portion 3a and a held portion 3b to be held when the bolt portion 3a is screwed. The bolt portion 3a is screwed with a nut provided at a position at which the gas sensor 1 is mounted. For example, the bolt portion 3a is screwed with a nut portion provided in the car exhaust pipe, whereby the gas sensor 1 is fixed to the exhaust pipe such that the first cover 2 side thereof is exposed in the exhaust pipe.

The second cover 4 is a cylindrical member that protects other part of the gas sensor 1. A wire harness WH which houses a plurality of lead wires (not shown) for electrically connecting the gas sensor 1 and a drive controller (not shown) extends from an end of the second cover 4.

FIG. 2 shows the internal configuration of the gas sensor 1, more specifically, the configuration of the gas sensor 1 except for the first cover 2 and second cover 4 shown in FIG. 1.

As shown in FIG. 2, inside the gas sensor 1, a washer 7, three ceramic supporters 8 (8a, 8b, and 8c), and two powder compacts 9 (9a and 9b) are each annularly mounted to the part of the sensor element 10 except for the first tip portion 10a, which includes the gas inlet 11 and the like, and a second tip portion 10b, which includes a connection terminal (electrode terminal) 13 for connection with the lead wires (not shown) housed in the wire harness WH, such that the sensor element 10 is positioned about the axis. The ceramic supporter 8 is a ceramic insulator. Meanwhile, the powder compact 9 is obtained by shaping ceramic powders such as talc. In the following description, the washer 7, the ceramic supporters 8, and the powder compacts 9 are collectively referred to as annularly-mounted members, in some cases, and an assembly in a state that these annularly-mounted members are annularly mounted to the sensor element 10 is referred to as a post-annularly-mounted assembly 31 (refer to FIGS. 7A to 7C), in some cases.

As shown in FIG. 2, a cylindrical tubular body (inner tube welded product) 30, which is obtained by integrating a housing 5 being a metallic cylindrical member and an inner tube 6 being a metallic cylindrical member, is annularly mounted to the outer peripheries of the washer 7, the ceramic supporters 8 (8a, 8b and 8c), and the power compacts 9 (9a and 9b).

The tubular body 30 is a member that the housing 5 and the inner tube 6 are integrated, with one end of the inner tube 6 welded to the housing 5. The housing 5 and the inner tube 6 have substantially the same inside diameter and are connected coaxially. An inside diameter of the tubular body 30 is set to be larger than designed values of maximum outside diameters of the respective annularly-mounted members.

The housing 5 is provided with a tapered portion 5c at one end side of the inside thereof. One end side of the post-annularly-mounted assembly 31 is engaged with an inside of the tubular body 30 by the tapered portion 5c. In a position of the inner tube 6 right above the washer 7 and a position of the inner tube 6 at the side of the powder compact 9a, respectively, concave portions 6a and 6b concaved inwardly are formed. Other end side of the post-annularly-mounted assembly 31 is engaged with an inside of the tubular body 30 by the concave portions 6a and 6b.

More specifically, the powder compact 9 is compressed after being annularly mounted, and is thereby attached firmly to the sensor element 10. The concave portions 6a and 6b are provided after compressing the powder compact 9. As a result that the firm attachment of the powder compact 9 to the sensor element 10 is achieved, in the tubular body 30, the sensor element 10 is fixed, and a sealing is achieved between the first tip portion 10a side including the gas inlet 11 or the like and the second tip portion 10b including the connection terminal (electrode terminal) 13 for the connection with the lead wires or the like in the sensor element 10. According to the above configuration, airtightness between a measurement gas space including the inspected gas (the measurement gas) which the first tip portion 10a of the sensor element 10 contacts and a reference gas space including a reference gas such as the atmosphere, for example, which the second tip portion 10b contacts is secured. The concave portions 6a and 6b are provided to maintain the compression state of the powder compact 9.

In this preferred embodiment, the sealing (the hermetic sealing) for maintaining the airtightness is performed in two stages, that is, a tentative sealing (a first compression) and a main sealing (a second compression). The detail of the hermetic sealing is described hereinafter.

In the following description, referred to as the assembled body 40 is a configuration that the tubular body 30 is annularly mounted to the post-annularly-mounted assembly 31 and the concave portions 6a and 6b are provided in the post-annularly-mounted assembly 31 as shown in FIG. 2. In the meanwhile, a workpiece under a state that the formation of the concave portion 6b, which is last performed in sequential assembling processes except for the inspection process, is not completed is referred to as a-semi-assembled body 40α (refer to FIGS. 7A to 7C).

The assembled body 40 having the aforementioned configuration in FIG. 2 is covered with the first cover 2, fixing bolt 3, and second cover 4, finally to form the gas sensor 1. Specifically, the first cover 2 is connected to a tubular portion 5a at a tip portion of the housing 5. The fixing bolt 3 is annularly mounted to the outer periphery of the housing 5 so as to come in contact with a projection (a flange portion) 5b. Moreover, the second cover 4 is mounted so as to be fitted into an annular groove (not shown) between the fixing bolt 3 and housing 5, which is formed through the above annular mounting.

Due to the above-mentioned configuration, in the gas sensor 1, the atmosphere around the first tip portion 10a of the sensor element 10 (atmosphere in the first cover 2) is completely cut off from the outside atmosphere in a case that the gas sensor 1 is mounted at a predetermined position. This allows for accurate measurement of the concentration of the targeted gas component in the detection gas.

Figure 3A:
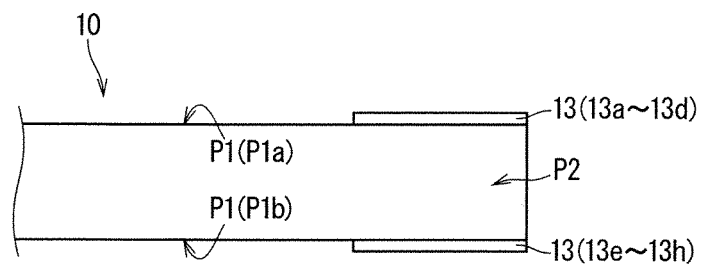
FIGS. 3A to 3C are views for describing details of an electrode terminal 13 of a sensor element 10.
Figure 3B:
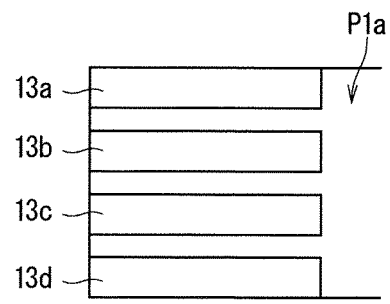
Figure 3C:
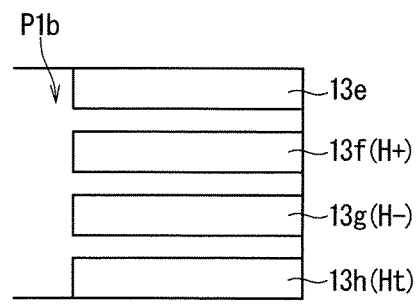

FIGS. 3A to 3C are views for describing details of an electrode terminal 13 of the sensor element 10. As shown in FIG. 3A, the plurality of electrode terminals 13 are provided in the side of the second tip portion 10b in the two main surfaces P1 (P1a and P1b) facing each other in the sensor element 10. More precisely, as shown in FIGS. 3B and 3C, each of the two main surfaces P1 is provided with the four electrode terminals 13, that is, the eight electrode terminals 13 in total. Specifically, electrode terminals 13a to 13d are provided in the one main surface P1a, and electrode terminals 13e to 13h are provided in the other main surface P1b. Particularly, the electrode terminals 13f to 13h in the above electrode terminals 13 are also referred to as H+ electrode, H− electrode, and Ht electrode, respectively.

Figure 4:
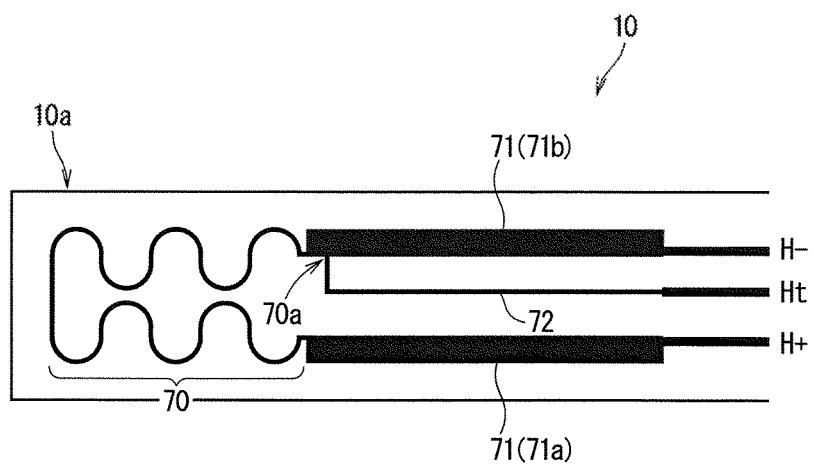
FIG. 4 is a view exemplifying a heater structure included in the sensor element 10.

FIG. 4 is a view exemplifying a heater structure included in the sensor element 10. The sensor element 10 comprises therein a heater 70 and a pair of heater leads 71 (71a and 71b) connected to both ends of the heater 70. The heater 70 is a resistance heater which generates heat when electrical power is supplied from outside of the sensor element 10 via the heater lead 71 which is an energizing path. The heater 70 can be formed of platinum, for example. The heater 70 is embedded in the side of the first tip portion 1a of the sensor element 10. An insulating layer made of alumina, for example, is formed above and below the heater 70 and heater lead 71 with a view to obtaining an electric insulation with an oxygen-ion conductive solid electrolyte.

The heater lead 71a and the heater lead 71b are provided to have substantially the same shape, that is to say, to have the same resistance value as each other. The one heater lead 71a is connected to the H+ electrode (the electrode terminal 13f) inside the sensor element 10, and the other heater lead 71b is connected to the H− electrode (the electrode terminal 13g) inside the sensor element 10.

Furthermore, a resistance detection lead 72 is provided in a manner of being lead from a connection part 70a of the heater 70 and the heater lead 71b. A resistance value of the resistance detection lead 72 can be ignored. The resistance detection lead 72 is connected to the Ht electrode (the electrode terminal 13h) inside the sensor element 10.

The electrode terminals 13f to 13h are also referred to as the heater electrode terminal hereinafter.

In the sensor element 10, electrical current is applied between the H+ electrode and the H− electrode heat with the heater 70, so that the closed space 12 and a surrounding area thereof (and the electrodes provided in each of them) can be heated to and kept at a predetermined temperature. The oxygen-ion conductivity of the solid electrolyte constituting the sensor element 10 is increased by the heat generation of the heater 70.

Since the heater lead 71a and the heater lead 71b have the same resistance value as each other and the resistance value of the resistance detection lead 72 can be ignored, a resistance value of the heater 70 (the heater resistance value) $R_H$ is calculated by the following equation when a resistance value between the H+ electrode and the Ht electrode is represented by $R_1$ and a resistance value between the H− electrode and the Ht electrode is represented by $R_2$:

$$R_H = R_1 - R_2 \quad (1)$$

As described hereinafter, the heater resistance value calculated by the equation (1) is subject to the inspection in a process of manufacturing the gas sensor 1 as the mass-produced product and shipping it according to this preferred embodiment.

<Outline of Manufacture and Inspection of Assembled Body>

Figure 5:
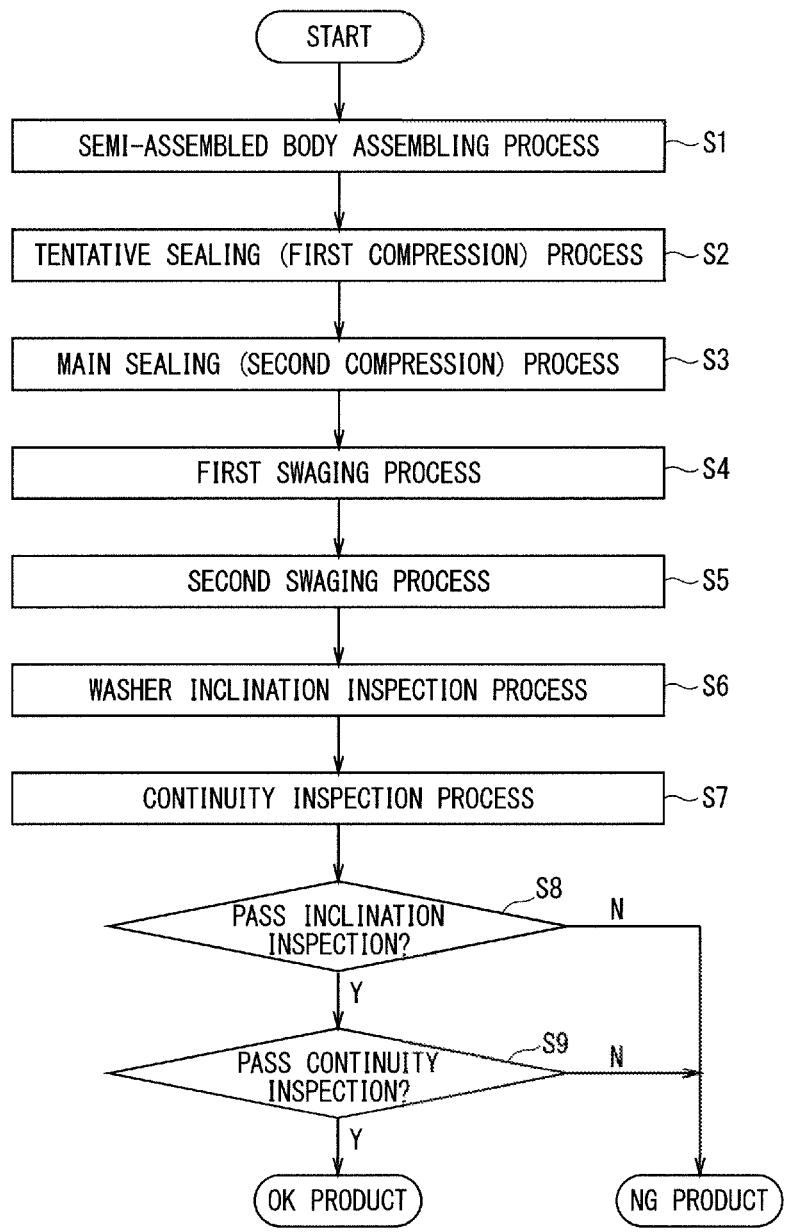
FIG. 5 is a view schematically illustrating a procedure of manufacturing and inspecting an assembled body 40.

Next, there will be described a process of manufacturing the assembled body 40, which is a main subject in this preferred embodiment, in a process of manufacturing the gas sensor 1 and a subsequent inspection process. FIG. 5 is a view schematically illustrating a procedure of manufacturing and inspecting the assembled body 40.

The assembled body 40 is manufactured by performing the following processes, in the procedure shown in FIG. 5, on the semi-assembled body 40α assembled by a-semi-assembled body assembling process (a step S1): performing the sealing process for hermetically sealing the inside of the semi-assembled body 40α in two stages, that is, the tentative sealing (the first compression) process (a step S2) and the main sealing (the second compression) process (a step S3), then forming the concave portion 6a in the inner tube 6 by the first swaging process (a step S4), and further forming the concave portion 6b in the inner tube 6 by the second swaging process (a step S5).

Then, sequentially performed as the inspection process are a washer inclination inspection process of inspecting an inclination of the washer 7 (a step S5) and a continuity inspection process of inspecting a conductive state by measuring a resistance value of the heater 70 (a heater resistance value) $R_H$ (a step S6).

When an index value for representing the inclination of the washer 7 obtained in the washer inclination inspection process meets a predetermined acceptability criterion (YES in a step S8) and also when the heater resistance value $R_H$ obtained in the continuity inspection process meets a predetermined acceptability criterion (YES in a step S9), the assembled body 40 is determined to be an OK product (an acceptable product) and is then provided to the process in the subsequent stages. In the meanwhile, when the index value obtained in the washer inclination inspection process or the heater resistance value obtained in the continuity inspection process does not meet their acceptability criteria (NO in the step S8 or NO in the step S9), the assembled body is determined to be an NG product (a defective product) and is excluded from a manufacturing object.

<Outline of Manufacturing Apparatus>

FIG. 6 is a block diagram schematically illustrating a structure of a manufacturing apparatus 100 for manufacturing and inspecting the assembled body 40 by the procedure shown in FIG. 5.

The manufacturing apparatus 100 includes a control part 101 for controlling the overall operations of the manufacturing apparatus 100, which is constituted by a CPU 101a, a ROM 101b, a RAM 101c and the like, an operating part 102 being an input interface constituted by switches, buttons, a touch panel and the like for providing various types of execution commands to the manufacturing apparatus 100, a display part 103 constituted by a display and measuring instruments for displaying various types of operation menus and operation states of the manufacturing apparatus 100, and a storage part 104 storing an operation program 104p for the manufacturing apparatus 100 and operation condition data and the like which are not illustrated. In the manufacturing apparatus 100, the operation program 104p is executed by the control part 101, so that a series of operations which will be described later are performed through automatic processing.

As components for actually manufacturing and inspecting the assembled body, the manufacturing apparatus 100 further includes a transportation part 110, a-semi-assembled body assembling part 120, a tentative sealing processing part 130, a main sealing/swaging processing part 140, a retightening processing part 150, and an inspection processing part 160.

The transportation part 110 is a part for transporting the semi-assembled body 40α and the assembled body 40 in the manufacturing apparatus 100. The transportation part 110 includes a transportation pallet 111 on which the semi-assembled body 40α and the assembled body 40 are disposed, a pallet movement mechanism 112 which moves the transportation pallet 111 to each part by a predetermined procedure, and a pallet delivery mechanism 113 for delivering the transportation pallet 111, in which the semi-assembled body 40α and the assembled body 40 are disposed, between each processing part.

The semi-assembled body assembling part 120 is a part for assembling the semi-assembled body 40α. The semi-assembled body assembling part 120 includes a first annularly-mounting mechanism 121 for annularly mounting the annularly-mounted members to the sensor element 10 to obtain the post-annularly-mounted assembly 31 and a second annularly-mounting mechanism 122 for annularly mounting the tubular body 30 to the post-annularly-mounted assembly 31 to obtain the semi-assembled body 40α.

Further, the semi-assembled body assembling part 120 includes an element standby part 123 and an annularly-mounted member standby part 124 in which the sensor element 10 and the annularly-mounted members (the washer 7, the ceramic supporter 8, and the powder compact 9), which are to be assembled, are disposed respectively, and also includes a tubular body standby part 125.

The tentative sealing processing part 130 is a part for performing the tentative sealing (the first compression), which is a processing for compressing the powder compact 9, mainly for purpose of positioning (fixing) the sensor element 10. The tentative sealing processing part 130 includes a pallet mounting stand 131 on which the transportation pallet 111 is disposed, an element positioning pin 132 for positioning the sensor element 10 at the time of the tentative sealing, an element constraining jig 133 for constraining the sensor element 10 during the tentative sealing to be located within a predetermined range, and a tentative sealing jig (a first compression jig) 134 for pressing the washer 7 at the time of the tentative sealing.

The tentative sealing processing part 130 further includes a positioning pin elevating mechanism 132m for performing operations for elevating the element positioning pin 132 in a vertical direction, a constraining jig movement mechanism 133m for moving the element constraining jig 133 in a horizontal plane, and a tentative sealing jig elevating mechanism 134m for performing operations for elevating the tentative sealing jig 134 in the vertical direction.

The main sealing/swaging processing part 140 is a part for performing the main sealing (the second compression) to secure the airtightness (hermetic sealing) between the measurement gas space and the reference gas space in the gas sensor 1 and forming the concave portion 6a by swaging the inner tube 6 (the first swaging). The main sealing/swaging processing part 140 includes a pallet mounting stand 141 on which the transportation pallet 111 is disposed, a main sealing jig 142 for pressing the washer 7 at the time of the main sealing, and a first swaging jig 143 for swaging the inner tube 6 to form the concave portion 6a.

The main sealing/swaging processing part 140 further includes a mounting stand elevating mechanism 141m for performing operations for elevating the pallet mounting stand 141 in the vertical direction and a swaging jig movement mechanism 143m for performing operations for moving the first swaging jig 143 in a horizontal plane.

The retightening processing part 150 is a part for forming the concave portion 6b by swaging the inner tube 6 (the second swaging). In this preferred embodiment, referred to as a retightening is the formation, in the inner tube 6, of the concave portion 6b in the second swaging process subsequent to the formation of the concave portion 6a in the first swaging process. The retightening processing part 150 includes a pallet mounting stand 151 on which the transportation pallet 111 is disposed, a retightening assist jig 152 abutting on the washer 7 at the time of the retightening, and a second swaging jig 153 for swaging the inner tube 6 to form the concave portion 6b.

The retightening processing part 150 further includes a mounting stand elevating mechanism 151m for performing operations for elevating the pallet mounting stand 151 in the vertical direction and a swaging jig movement mechanism 153m for performing operations for moving the second swaging jig 153 in a horizontal plane.

The inspection processing part 160 is a part for performing the washer inclination inspection and the continuity inspection on the assembled body 40 having reached to completion through the retightening performed by the retightening processing part 150. The inspection processing part 160 includes a pallet mounting stand 161 on which the transportation pallet 111 is disposed, a first height measurement part 162A and second height measurement part 162B for measuring height positions in different two parts of the washer 7 at the same time, a first conduction measurement part 163A and second conduction measurement part 163B electrically connected to the electrode terminals 13 provided in the different sides of the two main surfaces P1 (P1a and P1b) of the sensor element 10, and a work guide 164 for holding the sensor element 10 in measuring the conductivity.

The inspection processing part 160 further includes a height measurement part drive mechanism 162m for performing operations for elevating the first height measurement part 162A and second height measurement part 162B in the vertical direction and rotating them in the horizontal plane, a conduction measurement part drive mechanism 163m for performing operations for moving the first conduction measurement part 163A and second conduction measurement part 163B in the horizontal plane, a work guide movement mechanism 164m for performing operation for moving the work guide 164 in the horizontal plane, and a resistance measuring instrument 165 for outputting a resistance value of a component at the time when the first conduction measurement part 163A and second conduction measurement part 163B are electrically connected to the electrode terminal 13.

In addition, the manufacturing apparatus 100 further includes an inclination determination part 105 and a conduction determination part 106 as functional constituent elements achieved by a control part 101 due to the execution of the operation program 104p.

The inclination determination part 105 performs a processing for calculating the index value representing the inclination of the washer 7 based on a measurement result of the height position of the washer 7 in the first height measurement part 162A and second height measurement part 162B and thereby determining whether or not the calculated value falls within a range of a predetermined acceptability criterion (a threshold value).

The conduction determination part 106 performs a processing for obtaining resistance values from the resistance measuring instrument 165 for respective parts to which each of the first conduction measurement part 163A and second conduction measurement part 163B are connected, and performing a calculation based on the equation (1) from those resistance values to determine whether or not the obtained values fall within a predetermined acceptability criterion.

<Assembly of Intermediate Member>

A detailed description of the manufacturing and inspecting the assembled body 40 performed by the procedure shown in FIG. 5 is sequentially provided hereinafter.

Figure 7A:
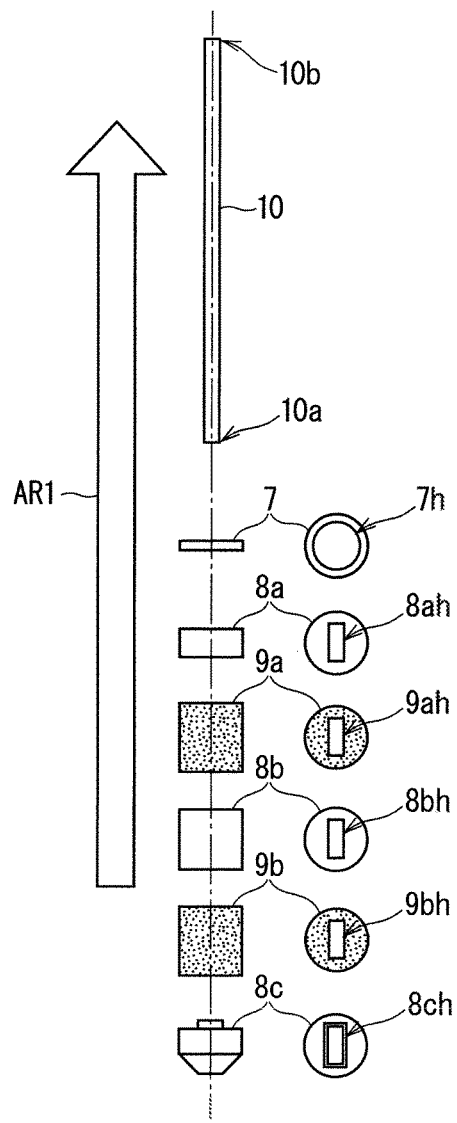
FIGS. 7A to 7C are views schematically illustrating a-semi-assembled body assembling process.
Figure 7B:
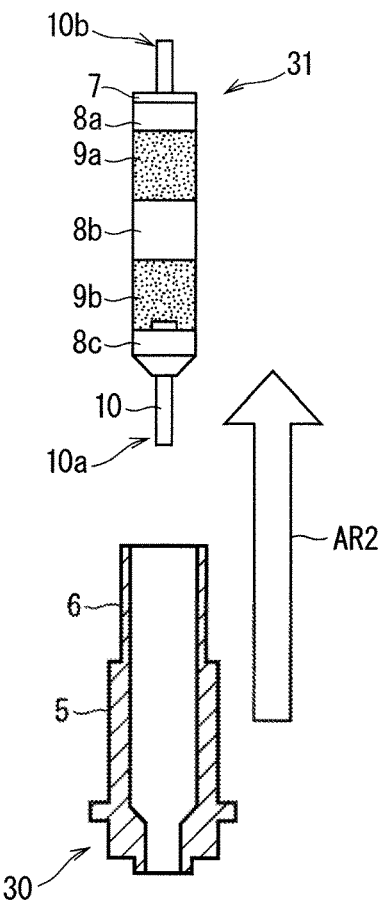
Figure 7C:
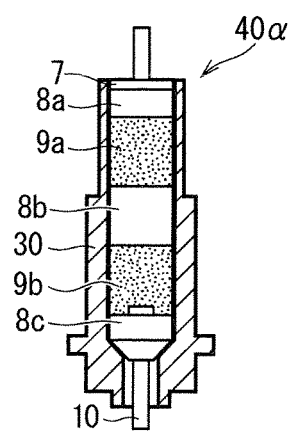

FIGS. 7A to 7C are views schematically illustrating a-semi-assembled body assembling process performed in the semi-assembled body assembling part 120 (the step S1 in FIG. 5).

In the semi-assembled body assembling process, firstly, the first annularly-mounting mechanism 121 obtains the sensor element 10 from the element standby part 123 and holds the sensor element 10 using a holding means not shown in the drawings. Subsequently, the first annularly-mounting mechanism 121 obtains the washer 7, the ceramic supporter 8a, the powder compact 9a, the ceramic supporter 8b, the powder compact 9b, and the ceramic supporter 8c from the annularly-mounted member standby part 124 in this order and then annularly mounts them to the sensor element 10 from the first tip portion 10a side of the sensor element 10 as indicated by an arrow AR1 in FIG. 7A. Accordingly, the post-annularly-mounted assembly 31 shown in FIG. 7B is obtained. The sensor element 10 and each annularly-mounted member are manufactured in a predetermined place in advance and prepared in the element standby part 123 and the annularly-mounted member standby part 124, respectively, prior to the execution of the semi-assembled body assembling process.

More specifically, each annularly-mounted member has a disc shape or cylindrical shape. For annularly mounting as described above, a circular through hole 7h is provided at the axis center position of the washer 7, and through holes 8ah, 9ah, 8bh, 9bh, and 8ch having a rectangular shape corresponding to the cross-sectional shape of the sensor element 10 are provided in the ceramic supporter 8a, powder compact 9a, ceramic supporter 8b, powder compact 9b, and ceramic supporter 8c, respectively. Those through holes are fitted with the sensor element 10, so that the members are each annularly mounted to the sensor element 10. In the above case, the washer 7, ceramic supporters 8, and powder compacts 9 are coaxially arranged.

From the point of securing the airtightness, the through holes of the ceramic supporters 8 and the through holes of the powder compacts 9 are configured such that a difference with a design cross-sectional size of the sensor element 10 is 0.25 to 0.35 mm and a dimensional tolerance is 0.1 mm. Meanwhile, the through hole 7h of the washer 7 is provided so as to have a difference with the design cross-sectional size of the sensor element 10 of at least 1 mm or more and 1.3 mm or less. The washer 7, ceramic supporters 8, and powder compacts 9 are configured to have a difference in outside diameter value of approximately 0.35 mm at a maximum.

Next, the second annularly-mounting mechanism 122 obtains the tubular body from the tubular body standby part 125 to annularly mount it to the post-annularly-mounted assembly 31 from an inner tube 6 side. Specifically, the tubular body 30 is annularly mounted to the post-annularly-mounted assembly 31 from a side providing the first tip portion 10a of the sensor element 10, as indicated by an arrow AR2 in FIG. 7B. Accordingly, the semi-assembled body 40α shown in FIG. 7C is obtained. At this time, since the semi-assembled body 40α is not sealed yet, the sensor element 10 is not completely fixed. Accordingly, the sensor element 10 can be displaced in the longitudinal direction due to an action of an external force, for example. In other words, in the semi-assembled body 40α which is not yet sealed, the sensor element 10 is not positioned. The sensor element 10 is positioned in the tentative sealing process performed in a next step.

<Transportation and Delivery by Transportation Part>

The semi-assembled body 40α assembled in the semi-assembled body assembling part 120 is then transported by the transportation part 110 and is delivered between the transportation part 110 and respective parts performing processing in subsequent stages.

Figure 8:
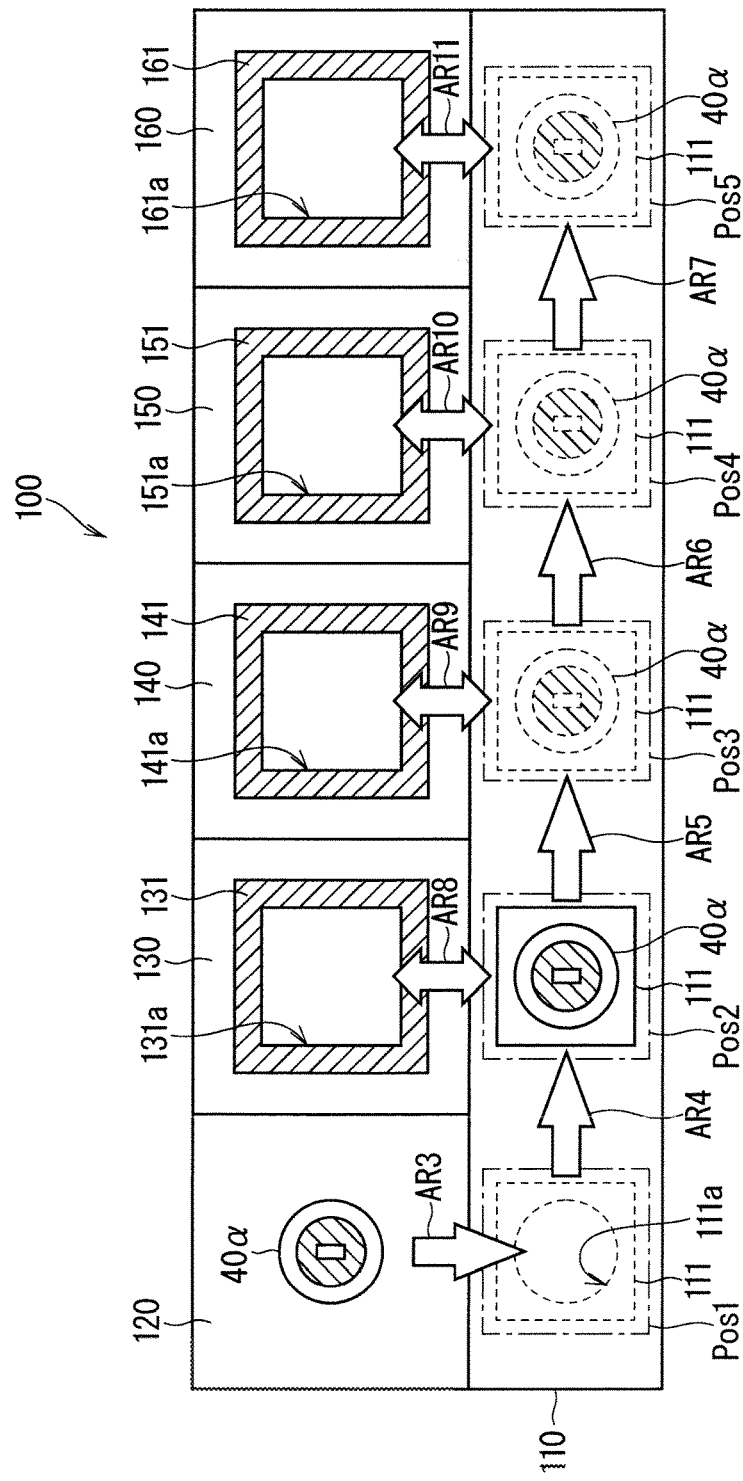
FIG. 8 is a planar view schematically illustrating a transport of a-semi-assembled body 40α and the assembled body 40 in a transportation part 110 and a delivery of the semi-assembled body 40α between the transportation part 110 and respective parts.

FIG. 8 is a planar view schematically illustrating a transportation of the semi-assembled body 40α and the assembled body 40 in the transportation part 110 and the delivery of the semi-assembled body 40α and the assembled body 40 between the transportation part 110 and respective parts.

In outline, the transportation part 110 is configured such that the semi-assembled body 40α and the assembled body 40 are transported in a state of being disposed on the transportation pallet 111, and the delivery of the semi-assembled body 40α or the assembled body 40 between the transportation part 110 and respective parts is performed together with the transportation pallet 111 on which the semi-assembled body 40 or the assembled body 40 is disposed.

A fitting part 111a is provided in an upper part of the transportation pallet 111, and the semi-assembled body 40α or the assembled body 40 is fitted with the fitting part 111a, so that the semi-assembled body 40α or the assembled body 40 is disposed on and fixed to the transportation pallet 111. More specifically, a lower portion of the tubular body 30 of the semi-assembled body 40α or the assembled body 40 in such a posture that its side provided with the washer 7 is directed upward is fitted into the fitting part 111a, so that the semi-assembled body 40α or the assembled body 40 is disposed on and fixed to the transportation pallet 111 (refer to FIG. 10, for example.) In this preferred embodiment, the lower portion of the tubular body 30 indicates the projection 5b and a part located below the projection 5b in the housing 5 in FIG. 2. In other words, the semi-assembled body 40α and the assembled body 40 are transported by the transportation pallet 111 in such a posture that the longitudinal direction of the sensor element 10 extends in the vertical direction and its side provided with the second tip portion 10b is directed upward. Such a posture of the semi-assembled body 40α and the assembled body 40 is also referred to as an assembly posture.

The semi-assembled body 40α and the assembled body 40 are preferably positioned so that a rotational deviation is prevented in the horizontal plane at the time of the disposition and fixing. This may be achieved by causing an outer periphery shape of the housing 5 to have anisotropy and also causing the fitting part 111a to have a shape corresponding to the outer periphery shape, or the holding means (not shown) included in the transportation pallet 111 may hold a horizontal posture of the semi-assembled body 40α and the assembled body 40.

In the transportation part 110, determined in advance are a first delivery position Pos1 for receiving the assembled semi-assembled body 40α from the semi-assembled body assembling part 120 and second delivery position Pos2 to fifth delivery position Pos5 for delivering the semi-assembled body 40α or the assembled body 40 between the transportation part 110 and the tentative sealing processing part 130, the main sealing/swaging processing part 140, the retightening processing part 150, and the inspection procession part 160, respectively.

The tentative sealing processing part 130, the main sealing/swaging processing part 140, the retightening processing part 150, and the inspection processing part 160 are provided with the pallet mounting stands 131, 141, 151, and 161 which the transportation pallet 111 is disposed on and fixed to, respectively. The pallet mounting stands 131, 141, 151, and 161 include pallet fitting parts 131a, 141a, 151a, and 161a, respectively, and the transportation pallet 111 is fitted into these pallet fitting parts 131a, 141a, 151a, and 161a in each processing part to achieve a state where the transportation pallet 111 is disposed on and fixed to the pallet mounting stands 131, 141, 151, and 161.

The pallet movement mechanism 112 (not shown in FIG. 8) firstly places the transportation pallet 111 in the first delivery position Pos1 at a timing of assembling the semi-assembled body 40α in the semi-assembled body assembling part 120. The obtained semi-assembled body 40α is delivered to the transportation pallet 111 disposed in the first delivery position Pos1, as indicated by an arrow AR3, by the pallet delivery mechanism 113 not shown in FIG. 8.

Subsequently, alternately performed are the transport of the transportation pallet 111 to the second delivery position Pos2 to fifth delivery position Pos5 performed by the pallet movement mechanism 112 indicated by arrows AR4 to AR7 and the delivery of the transportation pallet 111 between each delivery position and pallet mounting stand performed by the pallet delivery mechanism 113 indicated by arrows AR8 to AR11 in FIG. 8.

The transportation pallet 111 is returned from the inspection processing part 160 to the fifth delivery position Pos5 after the completion of the inspection processing in the inspection processing part 160. When the assembled body 40 held by the transportation pallet 111 is an acceptable product in the inspection performed in the inspection processing part 160, the assembled body 40 is delivered to an assembled body standby part 170. In the meanwhile, when the assembled body 40 is a rejected product in the inspection, the assembled body 40 is discarded. In any case, the transportation pallet 111 which has become empty is returned to the first delivery position Pos1 and is then used in the subsequent processing again.

Alternatively, it is also applicable the transportation pallet 111 which has transported the semi-assembled body 40α or the assembled body 40 from a previous delivery position to a delivery position corresponding to a certain processing part is different from the transportation pallet 111 which transports the semi-assembled body 40α or the assembled body 40 to a next delivery position after the completion of the processing in the processing part.

<Tentative Sealing>

The semi-assembled body 40α which has been assembled in the semi-assembled body assembling part 120 is provided to the tentative sealing (the first compression) process (the step S2 in FIG. 5) performed in the tentative sealing processing part 130. The tentative sealing process is a process performed mainly for purpose of tentatively fixing the sensor element 10 in a position where the sensor element 10 abuts to the element positioning pin 132. The term "tentative" is used herein by reason that a slight displacement of the sensor element 10 occurs at the time of the main sealing (the second compression) which is to be performed subsequently.

Figure 9:
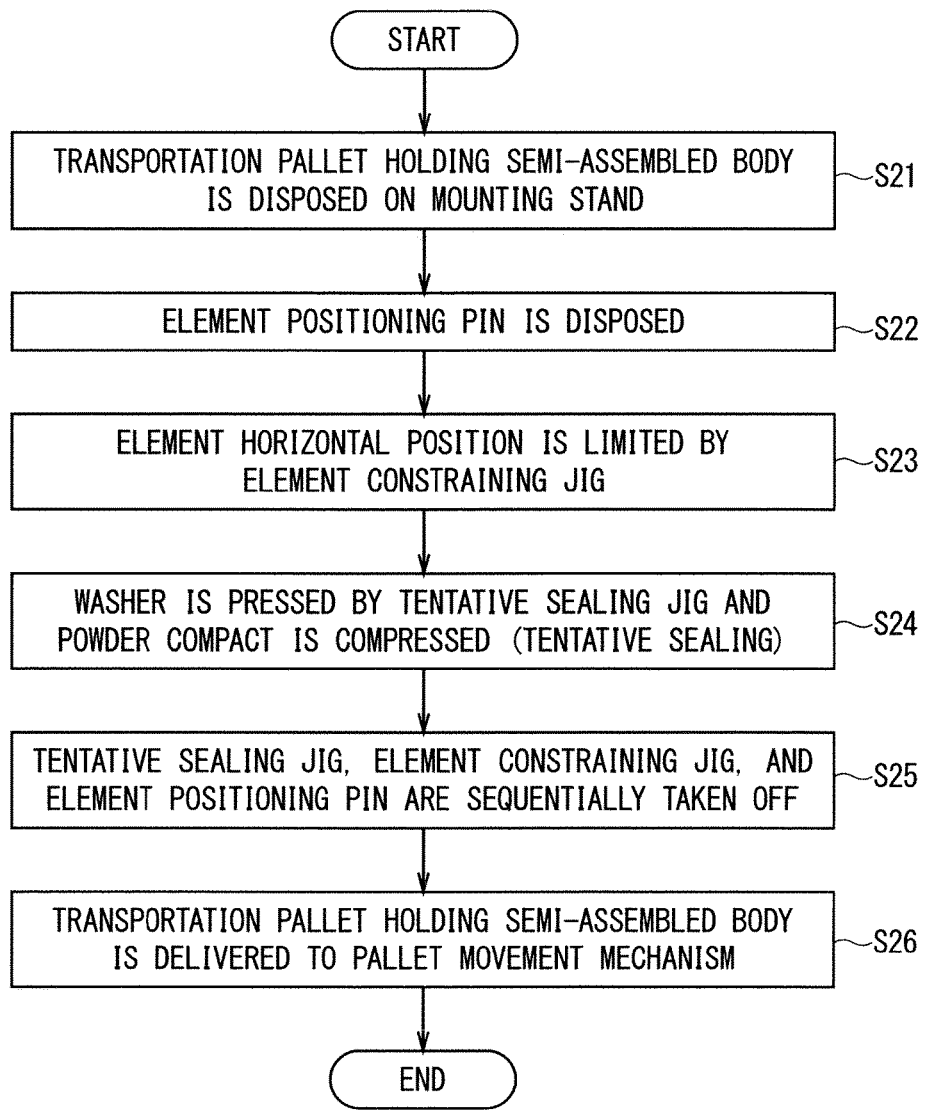
FIG. 9 is a view illustrating a more specific procedure of a tentative sealing process.
Figure 10:
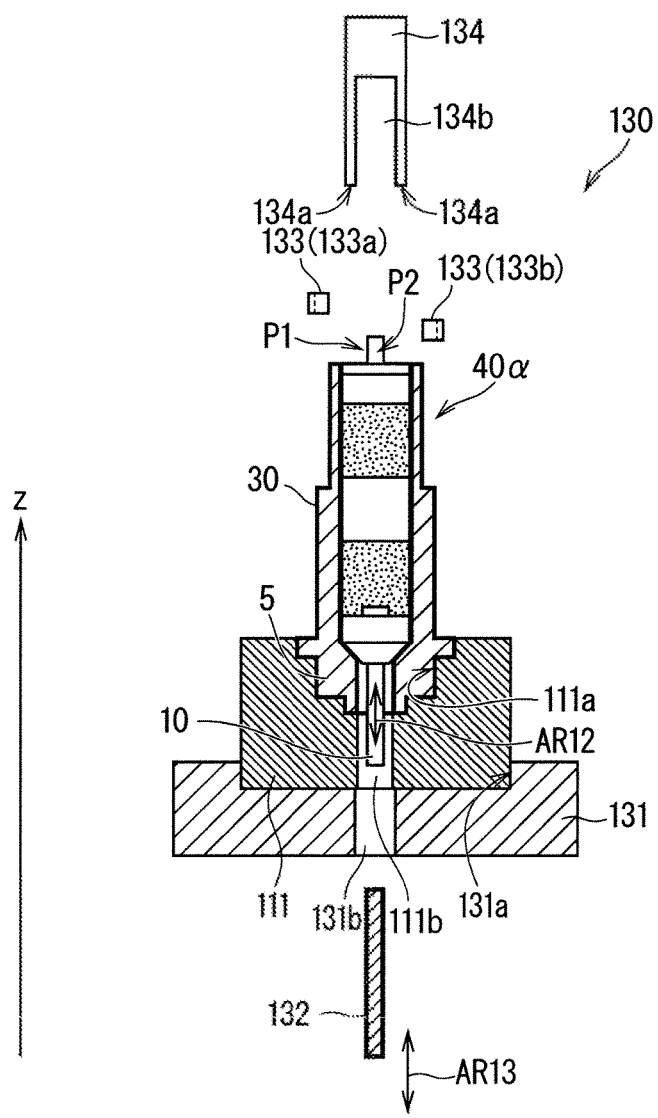
FIG. 10 is a side view schematically illustrating a structure of a tentative sealing processing part 130.
Figure 11A:
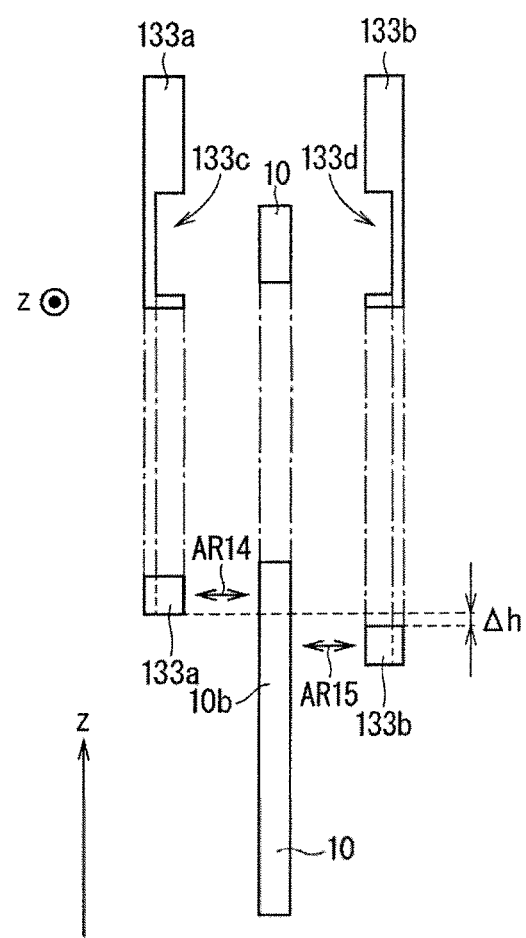
FIGS. 11A and 11B are views for describing an element constraining jig 133.
Figure 11B:
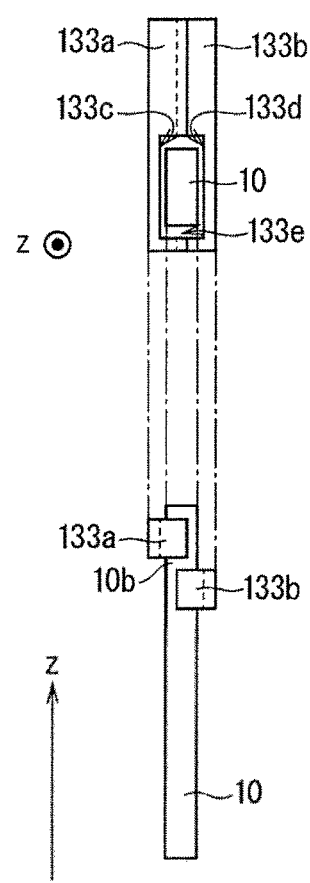

FIG. 9 is a view illustrating a more specific procedure of the tentative sealing process. FIG. 10 is a side view (a partial cross-sectional view) schematically illustrating a structure of the tentative sealing processing part 130. FIGS. 11A and 11B are views for describing the element constraining jig 133. Furthermore, FIGS. 12A to 13B are views illustrating a state halfway through the tentative sealing process in stages.

The tentative sealing processing part 130 mainly includes the pallet mounting stand 131, the element positioning ping 132, the pair of element constraining jigs 133 (133a and 133b), and the tentative sealing jig 134.

FIG. 10 illustrates a state where the transportation pallet 111 holding (placing and fixing) the semi-assembled body 40α is disposed on the pallet mounting stand 131. FIG. 10 illustrates a state where the semi-assembled body 40α is disposed and fixed in the assembly posture, in which a thickness direction of the sensor element 10 coincides a horizontal direction of FIG. 10, in other words, the main surface P1 is perpendicular to the horizontal direction of FIG. 10, and one of the side surfaces P2 is directed to a near side of FIG. 10. The state where the transportation pallet 111 to which the semi-assembled body 40α is placed and fixed is disposed on and fixed to the pallet mounting stand 131 is also referred to simply as a state where the semi-assembled body 40α is fixed to the pallet mounting stand 131. In FIG. 10 and subsequent drawings, a coordinate in which a vertical upper side is defined as a forward direction of a z axis is illustrated, appropriately.

As shown in FIG. 10, a hole part 111b is provided in a lower side of the fitting part 111a in the transportation pallet 111 to prevent the sensor element 10 protruding in a lower side of the semi-assembled body 40α from interfering with the transportation pallet 111. In addition, the pallet mounting stand 131 also includes a hole part 131b in a lower side of the pallet fitting part 131a. The hole part 131b is provided so as to come to be coaxial with the hole part 111b of the transportation pallet 111 at the time when the transportation pallet 111 is disposed on the pallet fitting part 131a.

As described above, since the sensor element 10 is not positioned, it can displaced up and down in the hole part 111b and further in the hole part 131b as indicated by an arrow AR12.

The hole parts 111b and 131b are also used as a space of elevating the element positioning pin 132. Although not shown in the drawings, the hole part 131b has a configuration that the sensor element 10 does not protrude from the transportation pallet 111.

The element positioning pin 132 has a configuration that it can be elevated in the vertical direction as indicated by an arrow AR13 and can enter the hole parts 111b and 131b in the positioning pin elevating mechanism 132m not shown in FIG. 10. Although the detail will be described hereinafter, the element positioning pin 132 raised by the positioning pin elevating mechanism 132m comes to abut to the sensor element 10 in the hole part 111b at the time of the tentative sealing, and the sensor element 10 is thereby positioned.

The pair of element constraining jigs 133 (133a and 133b) are provided in a position which is located in an upper side of the semi-assembled body 40α in the state where the semi-assembled body 40α is fixed to the pallet mounting stand 131. As shown in FIG. 11A, the element constraining jigs 133a and 133b have shapes line-symmetrical to each other in planar view but are provided at a predetermined distance Δh from each other in the vertical direction, which is also an extending direction of the sensor element 10. That is to say, they are provided in different height positions.

More specifically, the element constraining jigs 133a and 133b have groove portions 133c and 133d at their end portions, respectively, and the element constraining jigs 133a and 133b are disposed so that these groove portions 133c and 133d face each other in planar view.

The element constraining jigs 133a and 133b can move close to and away from each other in the horizontal plane as indicated by arrows AR14 and AR15 in FIG. 11A by the constraining jig movement mechanism 133m not shown in FIGS. 11A and 11B. More specifically, the element constraining jigs 133a and 133b are brought close to each other by the constraining jig movement mechanism 133m, with the sensor element 10 existing therebetween as shown in FIG. 11A, and then they forms the constraining region 133e having a rectangular shape in planar view with an intersection of each other as shown in FIG. 11B, so that the sensor element 10 (more specifically, the second tip portion 10b side) can be constrained within a range of the constraining region 133e.

The element constraining jig 133a and the element constraining jig 133b might be provided in the same height position. However, when their height position are differently provided as this preferred embodiment, a collision between them does not need to be considered at a time of bringing the element constraining jig 133a and the element constraining jig 133b close to each other to form the constraining region 133e. Therefore, this preferred embodiment is advantageous in view of a degree of freedom in processing the element constraining jig 133a and the element constraining jig 133b and size accuracy of the constraining region 133e.

The tentative sealing jig 134 is provided so as to be elevated in the vertical direction by the tentative sealing jig elevating mechanism 134m not shown in FIG. 10 in a position which is located in a vertical upper side of the semi-assembled body 40α (more specifically, the sensor element 10) in the state where the semi-assembled body 40α is fixed to the pallet mounting stand 131. The tentative sealing jig 134 includes a pair of abutting parts 134a in its lower side in the vertical direction. The pair of abutting parts 134a extend toward a vertically lower side, and abut to two portions, opposing each other of an upper surface of the washer 7, which constitutes the semi-assembled body 40α, from the upper side at the time of the tentative sealing. The tentative sealing jig 134 is disposed coaxially with the semi-assembled body 40α fixed to the pallet mounting stand 131.

A cavity part 134b is located between the pair of abutting parts 134a. The cavity part 134b is a part in which the sensor element 10 and the element constraining jig 133 are housed at the time of the tentative sealing. The cavity part 134b is provided to prevent interference between the tentative sealing jig 134 and the sensor element 10 and element constraining jig 133 when the tentative sealing jig 134 descends for the tentative sealing.

In performing the tentative sealing process in the tentative processing part 130, firstly, the transportation pallet 111, which has been delivered from the semi-assembled body assembling part 120 in the first delivery position Pos1 and holds (places and fixes) the semi-assembled body 40α, is disposed in the second delivery position Pos2 by the pallet movement mechanism 112, and then, the transportation pallet 111 is disposed on and fixed to the pallet mounting stand 131 in the tentative sealing processing part 130 together with the semi-assembled body 40α, by the pallet delivery mechanism 113, as shown in FIG. 10 (a step S21).

Figure 12A:
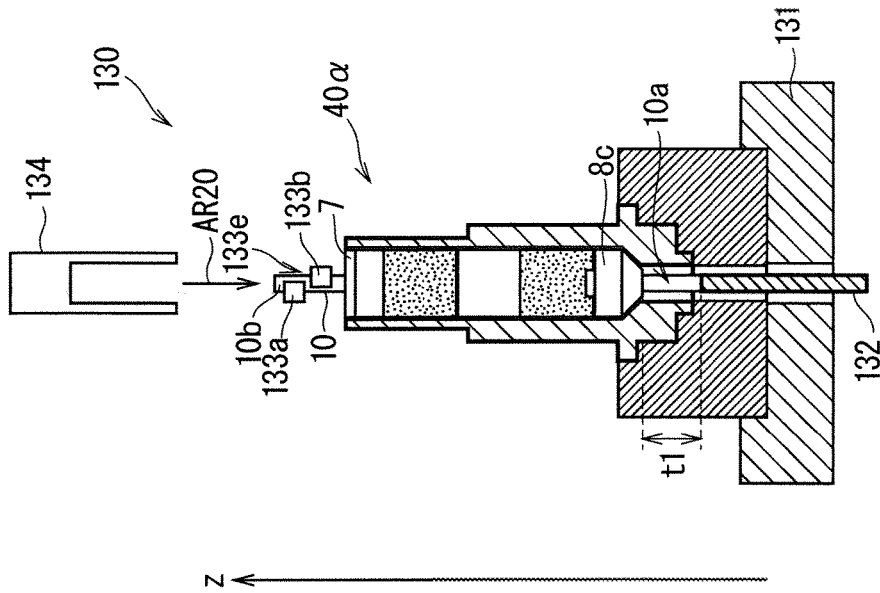
FIGS. 12A and 12B are views illustrating a state halfway through the tentative sealing process in stages.

Upon disposition and fixing, the positioning pin elevating mechanism 132m raises the element positioning pin 132 to the vertical upper side in the hole part 131b and the hole part 111b as indicated by an arrow AR16 in FIG. 12A to place the element positioning pin 132 in a predetermined position (a step S22).

More specifically, when a target value of a distance between a lowermost end of the ceramic supporter 8c and a lowermost end of the sensor element 10 (the end in the first tip portion 10a side) under a state that the assembled body 40 is hermetically sealed finally (referred to as a protruding length) is defined as t0, the element positioning pin 132 is disposed so that the protruding length is set to t1 which is shorter than t0. Accordingly, the sensor element 10 is pushed up as indicated by an arrow AR17, so that the second tip portion 10b protrudes from the tubular body 30. The position where the sensor element 10 is located at this time is defined as a first position.

Such a placement of the sensor element 10 in the first position where the protruding length is t1 due to pushing up the lowermost end of the sensor element 10 with the element positioning pin 132 is performed in consideration of the shifting that the sensor element 10 descends from the first position in the process in the subsequent stages, and the protruding length gets closer to t0. A difference between the protruding lengths t0 and t1 is experimentally determined in advance.

After the element positioning pin 132 is disposed in the first tip portion 10a side of the sensor element 10, an existing range of the sensor element 10 in the horizontal plane is subsequently limited by the element constraining jig 133 (a step S23).

Figure 12B:
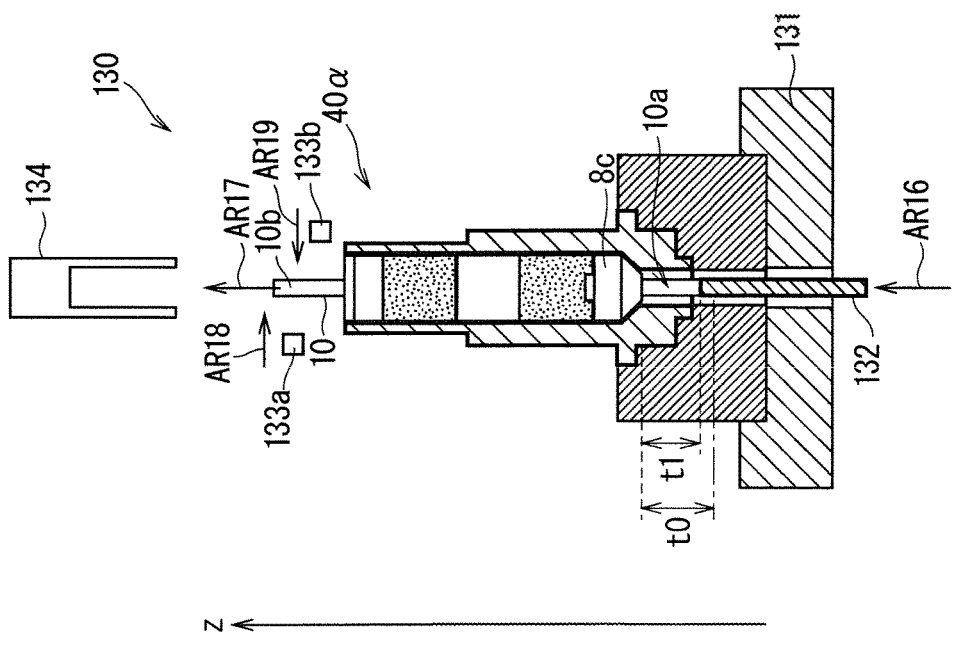

Specifically, the element constraining jig 133a and the element constraining jig 133b are moved in a direction close to each other as indicated by arrows AR18 and AR19 in FIG. 12A by the constraining jig movement mechanism 133m, thereby being disposed to form the constraining region 133e shown in FIGS. 11A and 11B. FIG. 12B shows a state where the element constraining jig 133a and the element constraining jig 133b are disposed as described above. Accordingly, in the subsequent processes, the existing range of the sensor element 10 in the horizontal plane (more generally, in a plane perpendicular to the extending direction of the sensor element 10 and the tubular body 30) is limited within the range of the constraining region 133e.

After the constraining region 133e is formed, the tentative sealing (the first compression) is subsequently performed by the tentative sealing jig 134 (a step S24).

The tentative sealing is achieved by lowering the tentative sealing jig 134 from the upper side of the semi-assembled body 40α toward the vertically lower side as indicated by an arrow AR20 in FIG. 12B, with the tentative sealing jig elevating mechanism 134m not shown in FIG. 12B.

When the tentative sealing jig elevating mechanism 134m lowers the tentative sealing jig 134, the abutting part 134a of the tentative sealing jig 134 abuts to the washer 7 in due course. At this time, the sensor element 10 and the element constraining jig 133 (133a and 133b) are housed in the cavity part 134b.

Figure 13A:
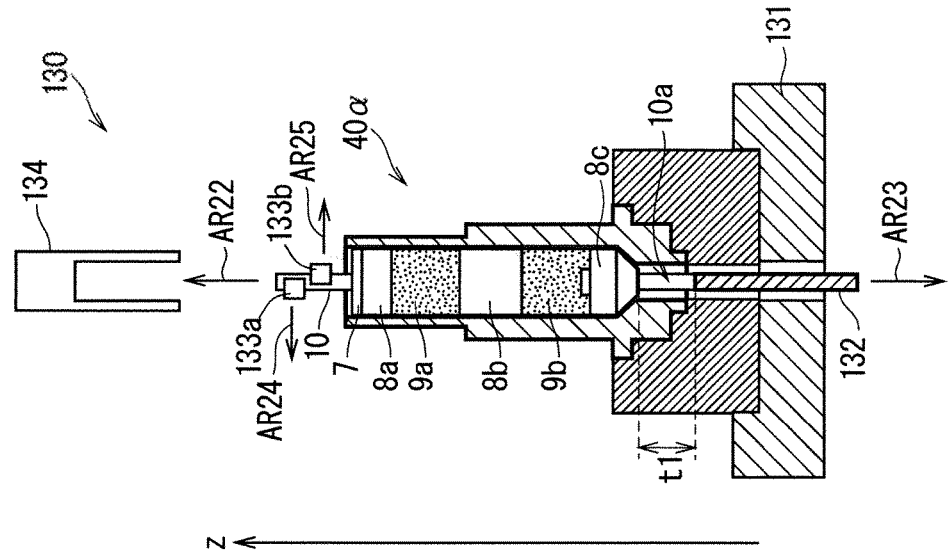
FIGS. 13A and 13B are views illustrating a state halfway through the tentative sealing process in stages.
Figure 13B:
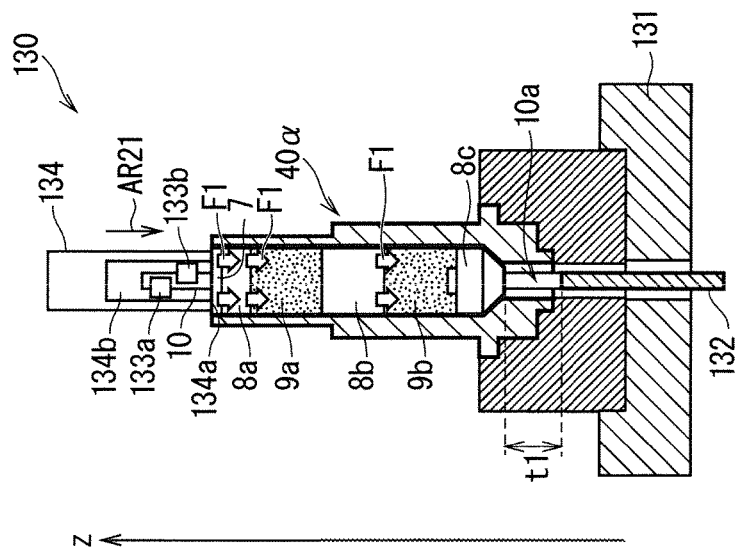

The tentative sealing jig elevating mechanism 134m continues to lower the tentative sealing jig 134 as indicated by an AR21 in FIG. 13A after the abutting part 134a abuts to the washer 7. The abutting part 134a of the tentative sealing jig 134 thereby presses the washer 7 to apply a vertically downward force (load) F1 (a first force) to the washer 7. Herein, the force F1 is applied within a range that the sensor element 10 can be fixed but a crack (or a break) does not occur in the sensor element 10. The actual value of the force F1 may be set in view of an area of the abutting part 134a which abuts to the washer 7.

When the force F1 acts on the washer 7 from the abutting part 134a, the washer 7 is slightly pushed vertically downward, and the force F1 also acting on the powder compacts 9a and 9b via the ceramic supporters 8a and 8b acts as a compression force. The powder compacts 9a and 9b are thereby compressed. In accordance with the compression, a gap between the powder compacts 9a and 9b and the sensor element 10 disappears, and the powder compacts 9a and 9b are attached firmly to the sensor element 10. Then, the sensor element 10 which has been displaceable in the vertical direction is fixed by the powder compacts 9a and 9b. Since the sensor element 10, which is positioned by the element positioning pin 132, is kept in the first position, the sensor element 10 is fixed, as a result, to the first position at which the protruding length in the lowermost end of the sensor element 10 is t1.

After the tentative sealing is finished, as indicated by arrows AR22 and AR25 in FIG. 131, the tentative sealing jig 134, the element positioning pin 132, the element constraining jig 133a, and the element constraining jig 133b are sequentially taken off (a step S25). Then, the transportation pallet 111 holding the semi-assembled body 40α, on which the tentative sealing has been performed, is delivered from the pallet mounting stand 131 to the pallet movement mechanism 112 by the pallet deliver mechanism 113 (a step S26). That is to say, the transportation pallet 111 is disposed in the second deliver position Pos2 again. The tentative sealing process is thereby finished.

Figure 14A:
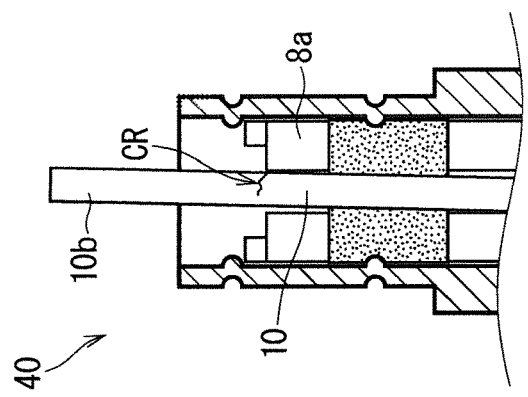
FIGS. 14A to 14C are cross-sectional views of a main part of the assembled body 40 for describing an effect of formation of a constraining region 133e at the time of the tentative sealing.
Figure 14B:
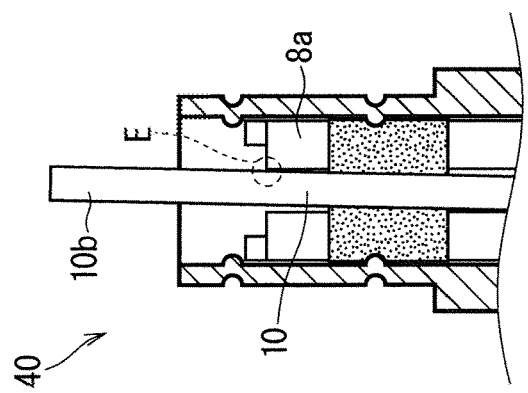
Figure 14C:
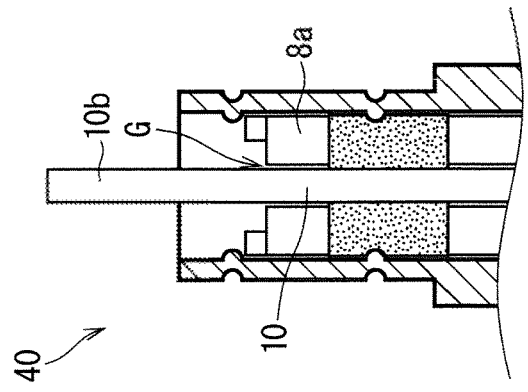

In the above tentative sealing process, the tentative sealing is performed with forming the constraining region 133e, as described above. FIGS. 14A to 14C are cross-sectional views of a main part of the assembled body 40 for describing an effect of formation of the constraining region 133e at the time of the tentative sealing.

The assembled body 40 is obtained through the main sealing process, the first swaging process, and the second swaging process after the tentative sealing process, and it is ideal that in the assembled body 40, the sensor element 10 is fixed to have a gap G between the sensor element 10 and the ceramic supporter 8a as shown in FIG. 14A. If the sensor element 10 is fixed in the assembled body 40 with being excessively inclined at the second tip portion 10b side or being totally displaced, the sensor element 10 may come in contact with the ceramic supporter 8a as indicated by a broken line part E shown in FIG. 14B, for example, and a stress may act on the sensor element 10 from the ceramic supporter 8a. Such a stress acting on the sensor element 10 may cause a defect such as a crack CR, a chip, or a breakage of the sensor element 10 originated in the crack CR, as shown in FIG. 14C. Such an inclination or displacement of the sensor element 10 is also referred to as "the misalignment" hereinafter. The defect due to the breakage of the sensor element 10 is also referred to as "the breakage failure of the element".

Such a misalignment of the sensor element 10 is most likely to occur in the tentative sealing process which is performed under a circumstance that the sensor element 10 is not completely fixed although it is annularly mounted with each annularly-mounted member and is positioned by the element positioning pin 132.

In this preferred embodiment, in view of the above points, the tentative sealing is performed under the circumstance that the constraining region 133e is formed by the pair of element constraining jigs 133, so that the misalignment, which may occur in the sensor element 10 at the time of the tentative sealing, is suppressed to such an extent that the sensor element 10 only comes in direct contact with the element constraining jig 133a or the element constraining jig 133b. A plane size of the constraining region 133e which is actually formed, the distance Δh between the element constraining jigs 133a and 133b, or the like, are different according to the size of the sensor element 10, the target value t0 of the protruding length of the sensor element 10, or the like. However, as long as at least a clearance between the pair of element constraining jigs 133 and the sensor element 10 at the time when the constraining region 133e is formed is equal to or smaller than a maximum possible design value of the gap between the sensor element 10 and the ceramic supporter 8a, which is closest to the constraining region 133e in the three ceramic supports 8 and, the sensor element 10 does not come in contact with the ceramic supporter 8a even if the sensor element 10 is inclined in the assembled body 40 to some degree.

FIG. 15 is a view describing how to evaluate the misalignment of the sensor element 10 in the assembled body 40. In this preferred embodiment, the degree of the misalignment of the sensor element 10 in the assembled body 40 is evaluated with a distance ΔC between a position C0 of a central axis of the inner tube 6 in the cross section perpendicular to the longitudinal direction of the assembled body 40 and a position C1 of a central axis of the sensor element 10. Therefore, the distance ΔC is also referred to as "the misalignment amount".

FIG. 16 is a view exemplifying an effect of the element constraining jig 133. Specifically, FIG. 16 is a histogram indicating a distribution of the misalignment amount in case of preparing the thirty assembled bodies 40 using the element constraining jig 133 at the time of the tentative sealing ("constrained" in FIG. 16) and the thirty assembled bodies 40 without using the element constraining jig ("not constrained" in FIG. 16) and evaluating the misalignment amount for all the assembled bodies 40.

It is confirmed from FIG. 16 that the alignment amount tends to be smaller in the case of "constrained" compared with the case of "not constrained". This means that using the element constraining jig 133 at the time of the tentative sealing has the effect of suppressing the misalignment.

<Main Sealing and First Swaging>

The semi-assembled body 40α on which the tentative sealing is performed in the tentative sealing processing part 130 is provided to the main sealing (the second compression) process (the step S3 in FIG. 5) and the subsequent first swaging process (the step S4 in FIG. 5) performed in the main sealing/swaging processing part 140. The main sealing process is a process performed mainly for purpose of securing the airtightness between the measurement gas space and the reference gas space. The first swaging process is a process performed for completely constraining the annularly-mounted member in the tubular body 30 of the main-sealed semi-assembled body 40α.

Figure 17:
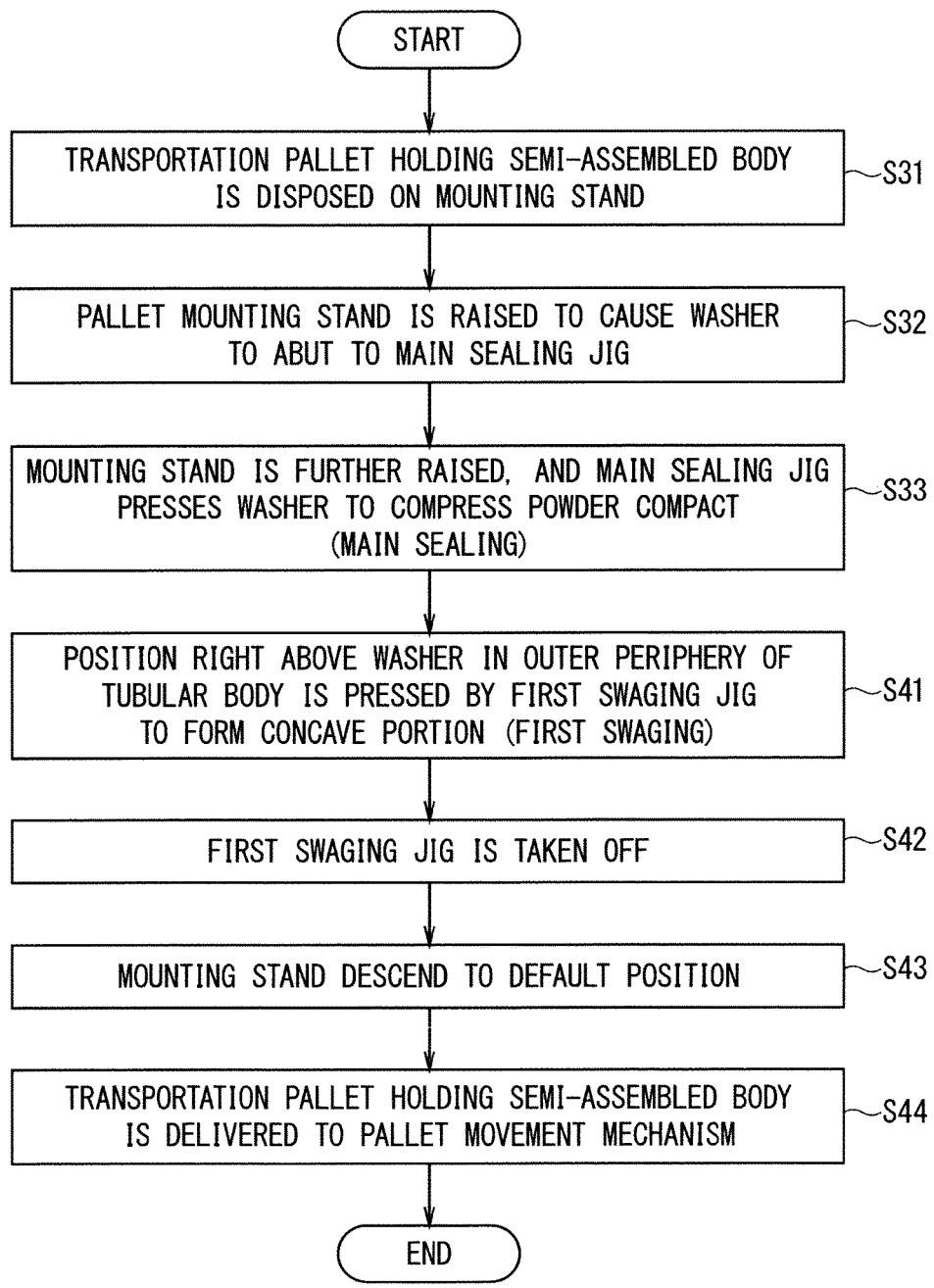
FIG. 17 is a view illustrating a more specific procedure of a main sealing process and a first swaging process.
Figure 19:
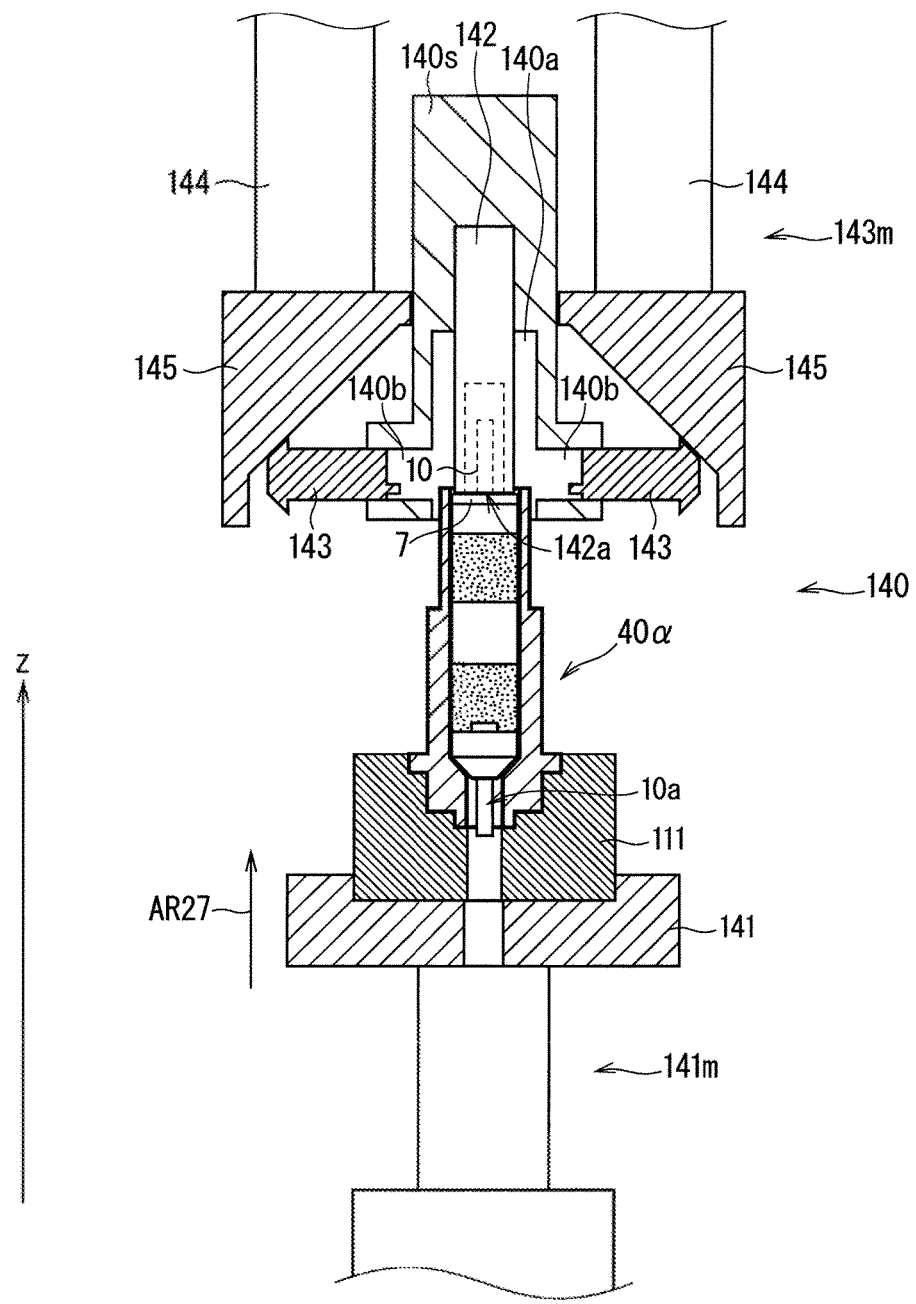
FIG. 19 is a view illustrating a state halfway through the main sealing process in stages.
Figure 20:
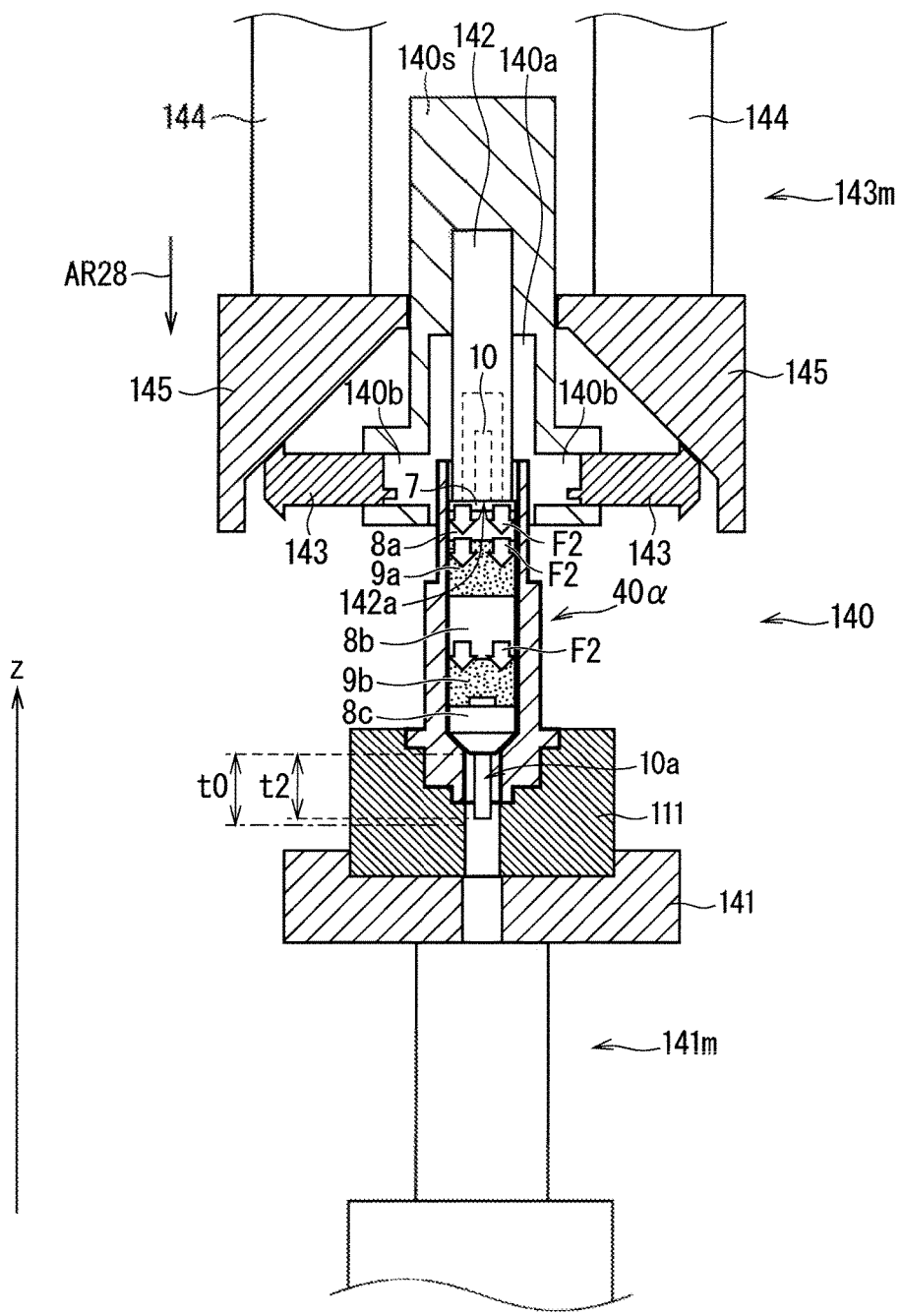
FIG. 20 is a view illustrating a state halfway through the main sealing process in stages.

FIG. 17 is a view illustrating a more specific procedure of the main sealing (the second compression) process and the first swaging process. The main sealing process and the first swaging process are sequentially performed in the main sealing/swaging processing part 140. FIG. 18 is a side view (a partial cross-sectional view) schematically illustrating a structure of the main sealing/swaging processing part 140. FIGS. 19 and 20 are views illustrating a state halfway through the main sealing process in stages. FIGS. 21A and 21B are views for describing an operation of the swaging jig movement mechanism 143m at the time of the first swaging. Furthermore, FIGS. 22, 23, and 24 are views illustrating a state halfway through the first swaging process in stages.

The main sealing/swaging processing part 140 mainly includes the pallet mounting stand 141, the main sealing jig 142, and the first swaging jig 143.

FIG. 18 illustrates a state where the transportation pallet 111 holding (placing and fixing) the semi-assembled body 40α is disposed on the pallet mounting stand 141. FIG. 18 also illustrates, in a manner similar to FIG. 10, a state where the semi-assembled body 40α is disposed and fixed in the assembly posture, in which the thickness direction of the sensor element 10 coincides the horizontal direction when seeing FIG. 18. The state where the transportation pallet 111 to which the semi-assembled body 40α is placed and fixed is disposed on and fixed to the pallet mounting stand 141 is also referred to simply as a state where the semi-assembled body 40α is fixed to the pallet mounting stand 141.

Although the pallet mounting stand 141 has a configuration similar to the pallet mounting stand 131 included in the tentative sealing processing part 130, it differs from the pallet mounting stand 131 in that it can be elevated in the vertical direction by the mounting stand elevating mechanism 141m. The mounting stand elevating mechanism 141m is made up of a servo cylinder.

The main sealing/swaging processing part 140 includes a support shaft 140s extending in the vertical direction in an upper position of the pallet mounting stand 141, and the main sealing jig 142 is attached to the support shaft 140s. More specifically, the support shaft 140s has a cavity part 140a which opens downward in its lower end, and the main sealing jig 142 is fixedly provided to the support shaft 140s so as to protrude to the cavity part 140a.

The main sealing jig 142 includes a substantially annular abutting part 142a, which abuts to the washer 7 which constitutes the semi-assembled body 40α from its upper side, in a lowermost end thereof in the vertical direction, and, a cavity part 142b which opens toward a vertically lower side. The main sealing jig 142 is disposed coaxially with the semi-assembled body 40α fixed to the pallet mounting stand 141.

A through hole 140b is provided in the support shaft 140s so as to extend laterally from the cavity part 140a, and the first swaging jig 143 is provided in the through hole 140b so as to be movable along an extending direction of the through hole 140b.

FIG. 18 illustrates the two through holes 140b in the horizontal direction of FIG. 18 and also illustrates the first swaging jig 143 disposed in each through hole 140b, however, the through hole 140b is actually provided in each of four sides of the cavity part 140a, that is to say, in four parts in total as described hereinafter. The first swaging jig 143 is also provided in each of the through hole 140b in the four parts (refer to FIGS. 21A and 21B).

The first swaging jig 143 includes a claw part 143a in one end directed to the cavity part 140a side and a guided part 143b which is guided by the swaging jig movement mechanism 143m in the other end side.

The swaging jig movement mechanism 143m includes a servo cylinder 144 provided to be extensible in the vertical direction and a guide member 145 provided in a lower end of the servo cylinder 144. The servo cylinder 144 and the guide member 145 are provided in four parts in total to correspond to each first swaging jig 143. The guide member 145 includes a guide surface 146 for guiding the guided part 143b of the first swaging jig 143. The guide surface 146 is inclined at an angle of a predetermined degrees with respect to the vertical direction and is perpendicular to a vertical plane including the extending direction of the through hole 140b in which the corresponding first swaging jig 143 exists. The guided part 143b of the first swaging jig 143 is provided to be in contact with the guide surface 146 and to be movable along the inclination direction of the guide surface 146.

In performing the main sealing process and the subsequent first swaging process in the main sealing/swaging processing part 140, the transportation pallet 111, which has been delivered from the tentative sealing processing part 130 in the second delivery position Pos2 and holds (places and fixes) the semi-assembled body 40α, is disposed in the third delivery position Pos3 by the pallet movement mechanism 112, and then, the transportation pallet 111 is disposed on and fixed to the pallet mounting stand 141 in the main sealing/swaging processing part 140 together with the semi-assembled body 40α, by the pallet delivery mechanism 113, as shown in FIG. 18 (a step S31).

After the transportation pallet 111 is disposed and fixed as described above, with the operation of the mounting stand elevating mechanism 141m, the pallet mounting stand 141 to which the semi-assembled body 40α is fixed is raised as indicated by an arrow AR26 in FIG. 18. When the pallet mounting stand 141 continues to be raised, the washer 7 of the semi-assembled body 40α comes to abut to the abutting part 142a of the main sealing jig 142 in due course, as shown in FIGS. 14A to 14C (a step S32). At this time, the sensor element 10 is housed in the cavity part 142b.

The mounting stand elevating mechanism 141m continues to raise the pallet mounting stand 141 as indicated by an arrow AR27 in FIG. 19 after the abutting part 142a abuts to the washer 7. The abutting part 142a of the main sealing jig 142 thereby presses the washer 7 to apply a vertically downward force (load) F2 (a second force) to the washer 7 as shown in FIG. 20. At this time, the force F2 is set to be large compared with the force F1 applied at the time of the tentative sealing. The actual value of the force F2 may be set in view of an area of the abutting part 142a which abuts to the washer 7.

When the force F2 acts on the washer 7 from the abutting part 142a, the washer 7 is further pushed vertically downward, and the force F2 also acting on the powder compacts 9a and 9b via the ceramic supporters 8a and 8b acts as a compression force. The powder compacts 9a and 9b are thereby further compressed. As a result, the hermetic sealing is achieved between the measurement gas space and the reference gas space. Accordingly, the main sealing (the second compression) is achieved (a step S33).

An upper limit value of the pressure acting on the washer 7 at the time of applying the force F2 may be appropriately set in view of a material strength of the main sealing jig 142, the washer 7, or the ceramic supporter 8, for example.

Since the main sealing is performed without causing the element positioning pin 132 to abut to the sensor element 10, the sensor element 10 which is once fixed in the first position by the powder compacts 9a and 9b at the time of the tentative sealing further slightly descends at the time of the main sealing. When the protruding length of the sensor element 10 after the main sealing is defined as t2, t2 has a value closer to t0 rather than t1. The position of the sensor element 10 after the main sealing is defined as a second position. Although it is ideal to satisfy t2=t0, it can be determined that the sensor element 10 is successfully fixed as long as a value Δt=t2−t0 falls within a predetermined error range allowed in light of characteristics desired for the gas sensor 1, that is to say, as long as the second position is within a range which is determined in advance for the position of the sensor element 10 in the assembled body 40 (the semi-assembled body 40α in this stage). Accordingly, in this preferred embodiment, the position of the element positioning pin 132 is determined so that the second position satisfies such a condition of the range. The allowable error range of Δt may be appropriately determined in advance.

In this preferred embodiment, the reason why the hermetic sealing is performed in two-stages is to prevent the occurrence of the chip (the break) in the sensor element 10 caused by applying a strong force at the time of the sealing. That is to say, although the lowermost end of the sensor element 10 abuts to the element positioning pin 132 at the time of the tentative sealing, the force F1 added to compress the powder compact 9 at the time of the tentative sealing is sufficiently smaller than the force F2 added at the time of the main sealing for securing the airtightness. Since the lowermost end of the sensor element 10 does not abut to the element positioning pin 132 at the time of the main sealing, the strong force does not act on the first tip portion 10a of the sensor element 10. Accordingly, in the case of the two-stage sealing performed in this preferred embodiment, the chip (the break) does not occur in the sensor element 10. In this preferred embodiment, accordingly, the occurrence of the defect caused by the chip (the break) in the sensor element 10 can be reliably prevented at the time of the hermetic sealing of the assembled body 40.

Furthermore, the sensor element 10 can be appropriately fixed in the desired position by appropriately determining a position of the element positioning pin 132 at the time of the tentative sealing, the force F1 acting on the powder compact 9 at the time of the tentative sealing, and the force F2 acting on the powder compact 9 at the time of the main sealing.

Specifically, in some cases, there is a strong correlation (a linear relationship, for example) between the protruding length t1 after the tentative sealing and the protruding length t2 after the main sealing. In the case that such a correlation is specified in advance, the protruding length t2 of the sensor element 10 after the main sealing can be set within the allowable error range of Δt based on the correlation, by appropriately determining the position of the lowermost end of the sensor element 10 at the time of the tentative sealing (that is to say, the upper end position of the element positioning pin 132) and the values of the forces F1 and F2 acted on by the tentative sealing jig 134 and the main sealing jig 142 at the time of the tentative sealing and the main sealing. That is to say, the sensor element 10 can be fixed in the desired position in light of the characteristics of the gas sensor 1.

After the main sealing is performed according to the above described manner, the first swaging process is subsequently performed while maintaining the state where the main sealing jig 142 is abutting to the washer 7. In outline, the first swaging is achieved by, as indicated by an arrow AR28 in FIG. 20, extending the servo cylinder 144 vertically downward in the swaging jig movement mechanism 143m.

FIGS. 21A and 21B are views for describing detailed configuration and operation of the first swaging jig 143 and the swaging jig movement mechanism 143m which is a movement mechanism of the first swaging jig 143. As illustrated by a schematic top view in a lower side of FIG. 21A, in the main sealing/swaging processing part 140, the four first swaging jigs 143 are provided toward four directions in the horizontal plane, respectively. Each first swaging jig 143 is configured to be movable along the through hole 140b extending in the horizontal direction. Under the state that the washer 7 of the semi-assembled body 40α abuts to the main sealing jig 142, these four first swaging jigs 143 are symmetrically located with respect to the inner tube 6 of the semi-assembled body 40α.

In the swaging jig movement mechanism 143m, when the servo cylinder 144 corresponding to each first swaging jig 143 is extended vertically downward as indicated by the arrow AR29, the guide member 145 associated with the servo cylinder 144 descends vertically downward. The guide member 145 then applies a vertically downward force to the guided part 143b of the first swaging jig 143 which is in contact with the guide surface 146 of the guide member 145 and is about to press down the guided part 143b. However, as described above, although the guided part 143b is provided to be movable along the inclination direction of the guide surface 146 which is the inclination surface, the first swaging jig 143 as a whole is configured to be movable along the through hole 140b extending in the horizontal direction. That is to say, the moving direction of the first swaging jig 143 is limited within the horizontal plane. Accordingly, as a result, when the guide member 145 descends due to the extension of the servo cylinder 144, the guided part 143b is relatively raised along the guide surface 146 as indicated by an arrow AR30 in FIG. 21A and at the same time, the first swaging jig 143 moves in the through hole 140b toward the inner tube 6 as indicated by an arrow AR31. When the servo cylinder 144 extends by a predetermined distance ΔZ, the claw part 143a of the first swaging jig 143 comes to abut to an outer periphery surface of the inner tube 6.

As shown in FIGS. 21A and 21B, an end of the claw part 143a included in each first swaging jig 143 has a curved surface in accordance with a shape of the inner tube 6, so that when the claw part 143a abuts to the inner tube 6, its whole curved surface is abutted to the inner tube 6.

As shown in FIG. 21B, a position (a height position) in which each claw part 143a abuts to the outer periphery surface of the inner tube 6 is set to a position right above the washer 7. In the manufacturing apparatus 100 according to this preferred embodiment, determined are the second force F2 added to the washer 7 in the main sealing process and the configuration and operation manner of the swaging jig movement mechanism 143m including the shape of the claw part 143a of the first swaging jig 143 or the like, in order to satisfy the positional relationship.

As shown in FIG. 22, when the servo cylinder 144 is continuously extended vertically downward as indicated by an arrow AR32 after the claw part 143a of the first swaging jig 143 comes to abut to the outer periphery surface of the inner tube 6, the inner tube 6 is pressed by the claw part 143a. The inner tube 6 is thereby swaged from the outer periphery side, and as shown in FIG. 23, the concave portion 6a is formed in the outer periphery surface of the inner tube 6 located right above the washer 7 (a step S41). The annularly-mounted member in the tubular body 30 is thereby completely constrained. Since the first swaging jigs 143 are located only in the four sides as shown in FIGS. 21A and 21B, the concave portion 6a is not necessarily formed around the inner tube 6 in the whole circumferential direction uniformly and continuously.

After the concave portion 6a is formed, the servo cylinder 144 is shortened vertically upward as indicated by an arrow AR33 in FIG. 23. Accordingly, the first swaging jig 143 which has pressed the inner tube 6 is also taken off as indicated by an arrow AR34 (a step S42).

After the first swaging jig 143 is taken off, the mounting stand elevating mechanism 141m operates again to lower the pallet mounting stand 141 to a default position as indicated by an arrow AR35 (a step S43). FIG. 24 illustrates a state after the pallet mounting stand 141 descends to the default position.

Then, the transportation pallet 111 holding the semi-assembled body 40α, on which the first swaging has been performed, is delivered from the pallet mounting stand 141 to the pallet movement mechanism 112 by the pallet deliver mechanism 113 (a step S44). That is to say, the transportation pallet 111 is disposed in the second deliver position Pos3 again. The main sealing process and the subsequent first swaging process are thereby finished.

<Second Swaging (Retightening)>

The semi-assembled body 40α on which the main sealing and the first swaging are performed in the main sealing/swaging processing part 140 is provided to the second swaging (retightening) process performed in the retightening processing part 150 (the step S5 in FIG. 5). The second swaging process is a process for further securing the constraining of the annularly-mounted member in the tubular body 30.

Figure 26:
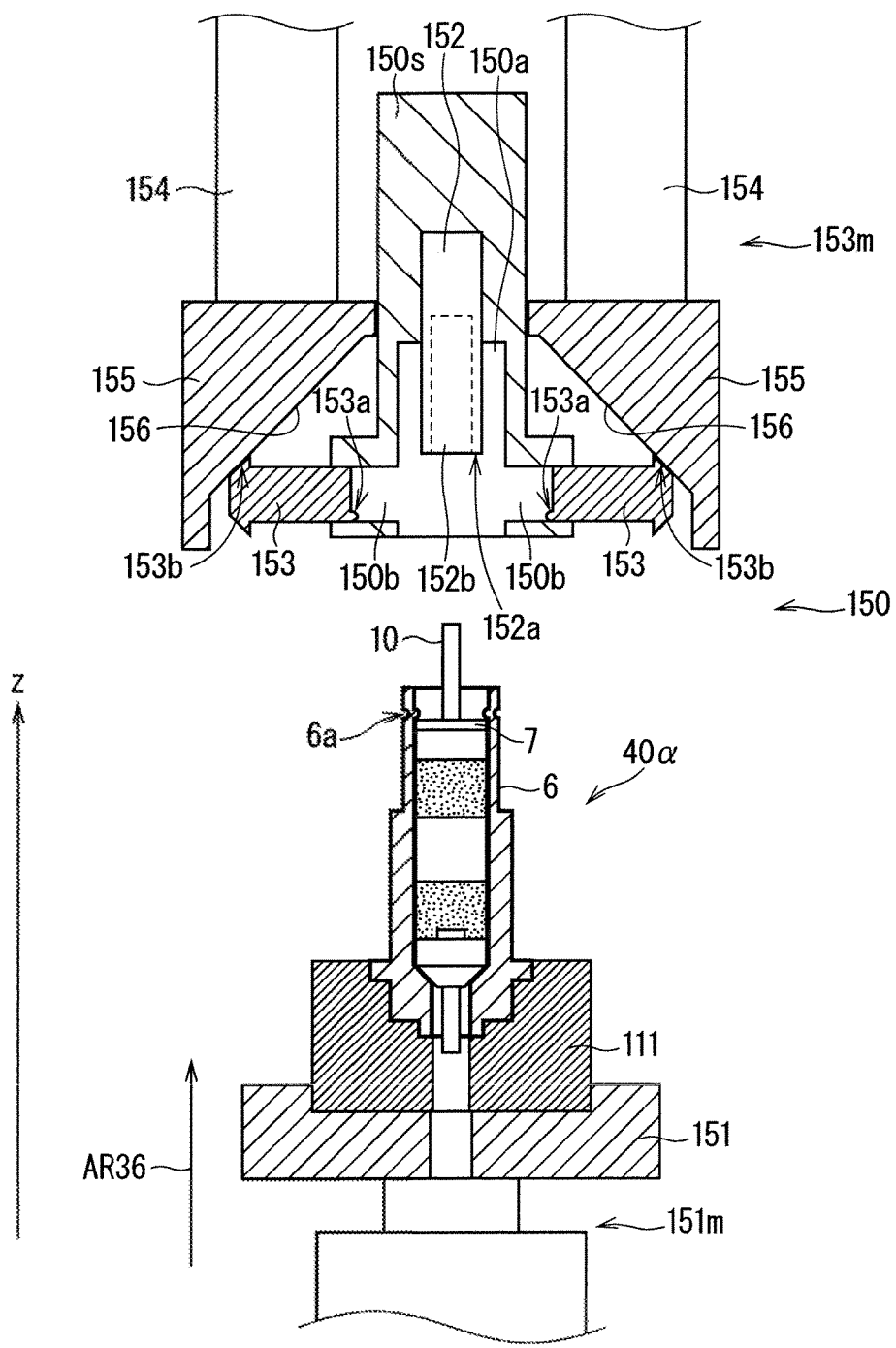
FIG. 26 is a side view schematically illustrating a structure of a retightening processing part 150.

FIG. 25 is a view illustrating a more specific procedure of the second swaging process. FIG. 26 is a side view (a partial cross-sectional view) schematically illustrating a structure of the retightening processing part 150. Furthermore, FIGS. 27, 28, 29, and 30 are views illustrating a state halfway through the second swaging process in stages.

The retightening processing part 150 mainly includes the pallet mounting stand 151, the retightening assist jig 152, and the second swaging jig 153.

FIG. 26 illustrates a state where the transportation pallet 111 holding (placing and fixing) the semi-assembled body 40α is disposed on the pallet mounting stand 151. FIG. 26 also illustrates, in a manner similar to FIG. 10, a state where the semi-assembled body 40α is disposed and fixed in the assembly posture, in which a thickness direction of the sensor element 10 coincides to the horizontal direction when seeing FIG. 26. The state where the transportation pallet 111 to which the semi-assembled body 40α is placed and fixed is disposed on and fixed to the pallet mounting stand 151 is also referred to simply as a state where the semi-assembled body 40α is fixed to the pallet mounting stand 151.

The retightening processing part 150 has a configuration similar to the main sealing/swaging processing part 140 described above. That is to say, the pallet mounting stand 151 and the mounting stand elevating mechanism 151m have configurations similar to the pallet mounting stand 141 and the mounting stand elevating mechanism 141m of the main sealing/swaging processing part 140. The retightening processing part 150 includes a support shaft 150s extending in the vertical direction in an upper position of the pallet mounting stand 151, and the support shaft 150s has a cavity part 150a which opens downward in a lower end thereof. The retightening assist jig 152 is fixedly provided to the support shaft 150s so as to protrude to the cavity part 150a. These configurations are similar to the configuration manner of the support shaft 140s, the cavity part 140a, and the main sealing jig 142 in the main sealing/swaging processing part 140.

However, a height position of an abutting part 152a of the retightening assist jig 152 is determined so that a height position of the powder compact 9a constituting the semi-assembled body 40α coincides with a height position of a claw part 153a of the second swaging jig 153 under a state that the washer 7 abuts to the abutting part 152a. A protruding length of the retightening assist jig 152 protruding from the support shaft 150s is thereby smaller than that of the main sealing jig 142 protruding from the support shaft 140s.

The configurations of the second swaging jig 153 (the claw part 153a and a guided part 153b), a through hole 150b in which the second swaging jig 153 is disposed, and the swaging jig movement mechanism 153m for moving the second swaging jig 153 in the horizontal plane (a servo cylinder 154, a guide member 155, and the guide surface 156) are also substantially similar to those of the first swaging jig 143 (the claw part 143a and the guided part 143b), a through hole 140b in which the first swaging jig 143 is disposed, and the swaging jig movement mechanism 143m for moving the first swaging jig 143 in the horizontal plane (the servo cylinder 144, the guide member 145, and the guide surface 146). Accordingly, a detailed description of the configuration in the retightening processing part 150 is omitted.

However, the shape of the claw part 153a of the second swaging jig 153 may differ from the shape of the claw part 143a of the first swaging jig 143. The shape of the claw part 153a of the second swaging jig 153 illustrated in FIGS. 26 to 30 differs from the shape of the claw part 143a of the first swaging jig 143 illustrated in FIGS. 18 to 24.

In performing the second swaging (retightening) process in the retightening processing part 150 having the above configuration, firstly, the transportation pallet 111, which has been delivered from the main sealing/swaging processing part 140 in the third delivery position Pos3 and holds (places and fixes) the semi-assembled body 40α, is disposed in the fourth delivery position Pos4 by the pallet movement mechanism 112, and then, the transportation pallet 111 is disposed on and fixed to the pallet mounting stand 151 in the retightening processing part 150 together with the semi-assembled body 40α, by the pallet delivery mechanism 113, as shown in FIG. 26 (a step S51).

After the transportation pallet 111 is disposed and fixed as described above, with the operation of the mounting stand elevating mechanism 151m, the pallet mounting stand 151 to which the semi-assembled body 40α is fixed is raised as indicated by an arrow AR36 in FIG. 26. When the pallet mounting stand 151 continues to be raised, the washer 7 of the semi-assembled body 40α comes to abut to the abutting part 152a of the retightening assist jig 152 in due course, as shown in FIG. 27 (a step S52). At this time, the sensor element 10 is housed in the cavity part 152b.

Figure 28:
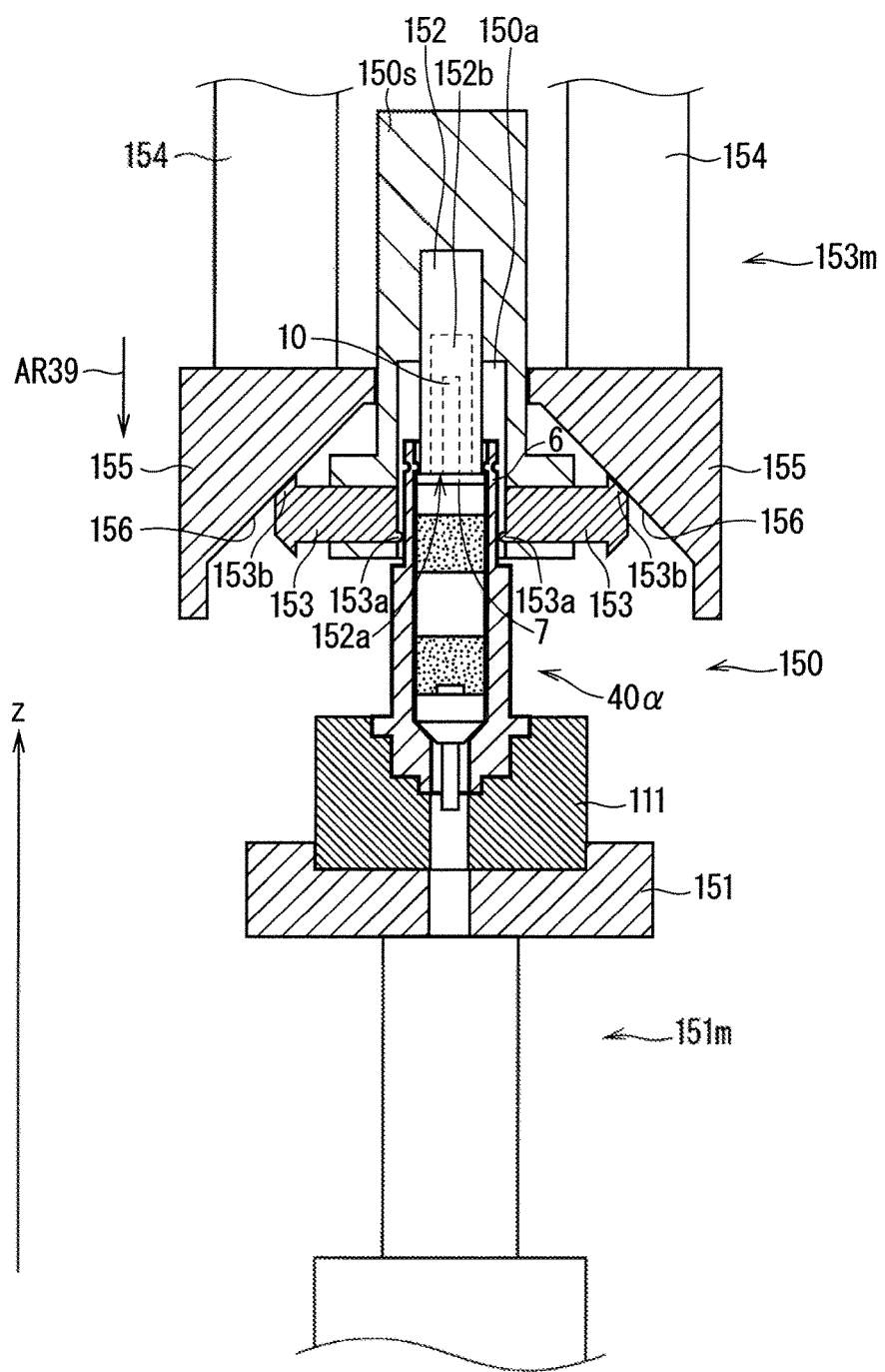
FIG. 28 is a view illustrating a state halfway through the second swaging process in stages.

After the washer 7 abuts to the abutting part 152a according to the above described manner, the servo cylinder 154 is extended vertically downward in the swaging jig movement mechanism 153m as indicated by an arrow AR37 in FIG. 27. Then, the second swaging jig 153 moves in the through hole 150b toward the inner tube 6 as indicated by an arrow AR38, and the claw part 153a of the second swaging jig 153 comes to abut to the outer periphery surface of the inner tube 6 in the lateral position of the powder compact 9a in due course as shown in FIG. 28.

Figure 29:
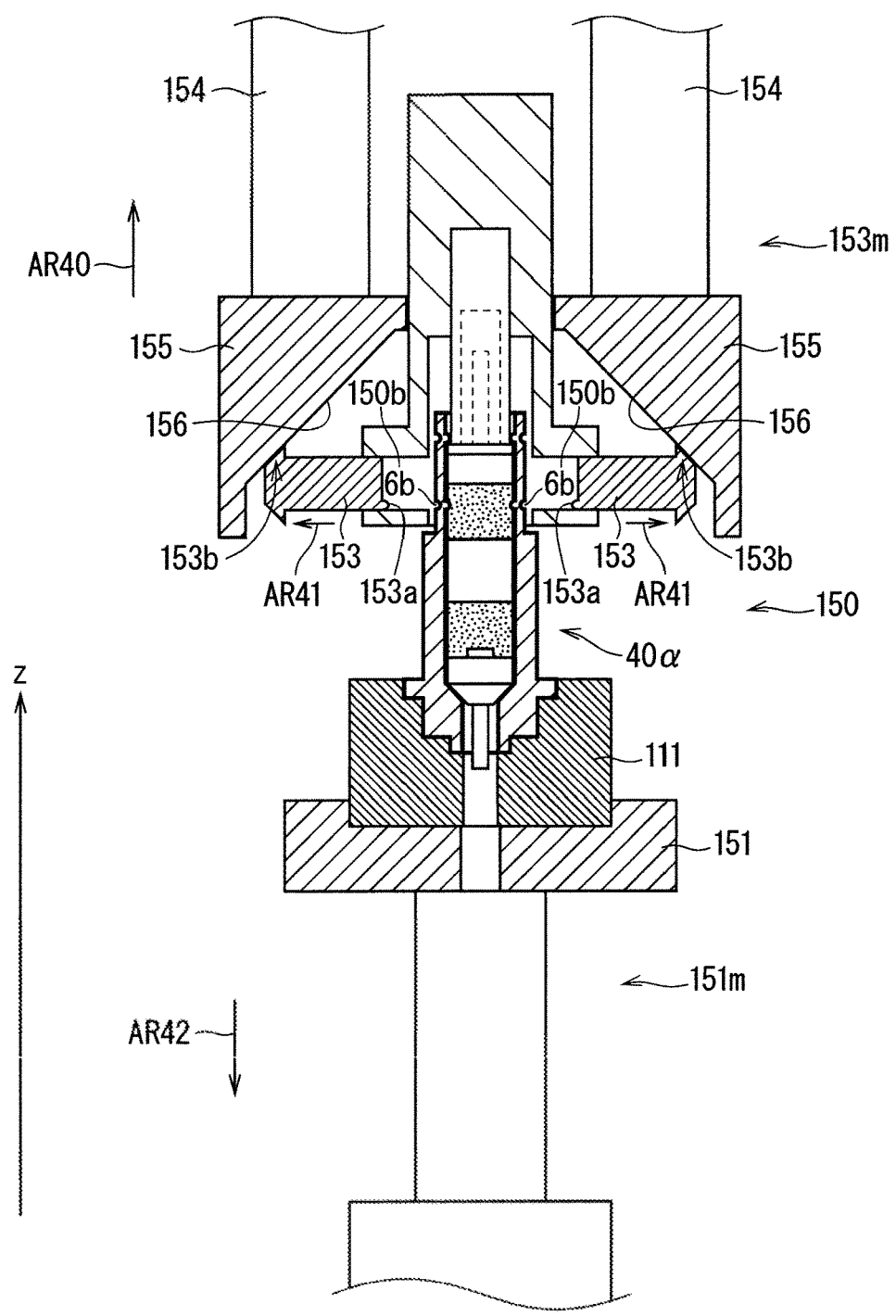
FIG. 29 is a view illustrating a state halfway through the second swaging process in stages.

When the servo cylinder 154 is continuously extended vertically downward, as indicated by an arrow AR39, after the claw part 153a comes to abut to the outer periphery surface of the inner tube 6, the inner tube 6 is pressed by the claw part 153a. The inner tube 6 is thereby swaged from the outer periphery side, and as shown in FIG. 29, the concave portion 6b is formed in the outer periphery surface of the inner tube 6 in the lateral position of the powder compact 9a (a step S53). The constraining of the annularly-mounted member in the tubular body 30 is further secured as a result that the concave portion 6b is formed. The assembly of the assembled body 40 is finished by forming the concave portion 6b.

After the concave portion 6b is formed, the servo cylinder 154 is shortened vertically upward as indicated by an arrow AR40 in FIG. 29. Accordingly, the second swaging jig 153 which has pressed the inner tube 6 is also taken off as indicated by an arrow AR41 (a step S54).

Figure 30:
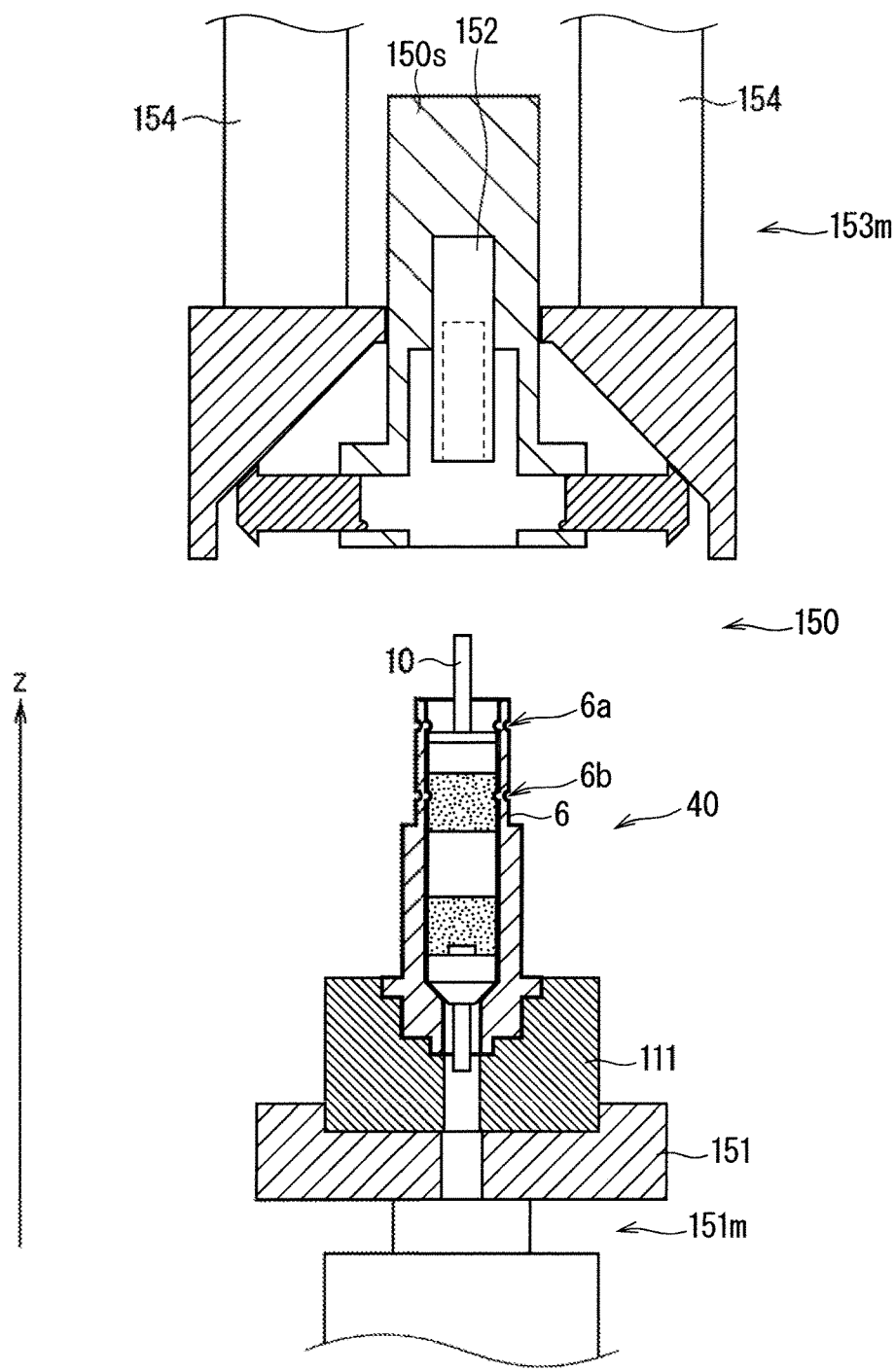
FIG. 30 is a view illustrating a state halfway through the second swaging process in stages.

After the second swaging jig 153 is taken off, the mounting stand elevating mechanism 151m operates again to lower the pallet mounting stand 151 to a default position as indicated by an arrow AR42 (a step S55). FIG. 30 illustrates a state after the pallet mounting stand 141 descends to the default position.

Then, the transportation pallet 111 holding the assembled body 40 is delivered from the pallet mounting stand 151 to the pallet movement mechanism 112 by the pallet deliver mechanism 113 (a step S56). That is to say, the transportation pallet 111 is disposed in the fourth deliver position Pos4 again. The second swaging (retightening) process is thereby finished.

In this preferred embodiment, the assembled body 40 constituting the main body of the gas sensor 1 is manufactured by the procedure described above. As described above, in this preferred embodiment, positioning and fixing the sensor element 10 and hermetically sealing the space of both end sides of the sensor element 10 by compressing the powder compact 9 is performed in the two stages, that is, the tentative sealing (the first compression) mainly for purpose of positioning the sensor element 10 and the main sealing (the second compression) performed after the tentative sealing without using the element positioning pin 132, and furthermore, the range of inclination or displacement of the sensor element 10 is bound by the element constraining jig 133 at the time of the tentative sealing. Accordingly, the occurrence of the defect caused by the chip (the break) or the breakage failure of the element in the sensor element 10 is appropriately suppressed inside the assembled body 40.

The position of the element positioning pin 132 is determined in consideration of the positional deviation of the sensor element at the time of the main sealing, so that fixing of the sensor element 10 in a desired position without the chip (the break) therein as well as hermetic sealing is achieved inside the assembled body 40.

The inventor or the present invention confirmed that an occurrence ratio of the breakage failure of the element inside the assembled body 40 (a ratio of breakage failure of the element) when the assembled body 40 is assembled without using the element constraining jig 133 at the time of the tentative sealing is 0.3%, whereas the ratio of breakage failure of the element is reduced to 0.001% when the element constraining jig 133 is used at the time of the tentative sealing.

<Inspection of Assembled Body>

The assembled body 40 having reached to completion through the retightening is provided to the inspection process performed in the inspection processing part 160, that is to say, the washer inclination inspection process (the step S6 in FIG. 5) and the subsequent continuity inspection process (the step S7 in FIG. 5).

The washer inclination inspection process is performed in order to exclude the assembled body 40 in which the washer 7 is inclined beyond a predetermined allowable range from a manufacturing object of the gas sensor 1. The breakage failure of the element tends to occur easily in the gas sensor 1 having the washer 7 with larger inclination. It is considered that this is because, when the washer 7 is inclined, the ceramic supporter 8a which is in contact with the washer 7 is also inclined, so that even when the sensor element 10 is not inclined or displaced, the sensor element 10 comes in contact with the ceramic supporter 8a and the stress thereby acts on the sensor element 10, and the sensor element 10 is broken by the stress. This tendency is also confirmed from a result of an impact test performed on the plurality of assembled bodies 40 having different degrees of inclination of washer 7.

In this preferred embodiment, defined as a washer inclination amount is a difference value between a maximum value and a minimum value in heights of four points in the washer 7 making 90-degree angle with each other in a circumferential direction, and the washer inclination amount is used as an index value indicating a degree of the inclination of the washer 7.

Figure 31:
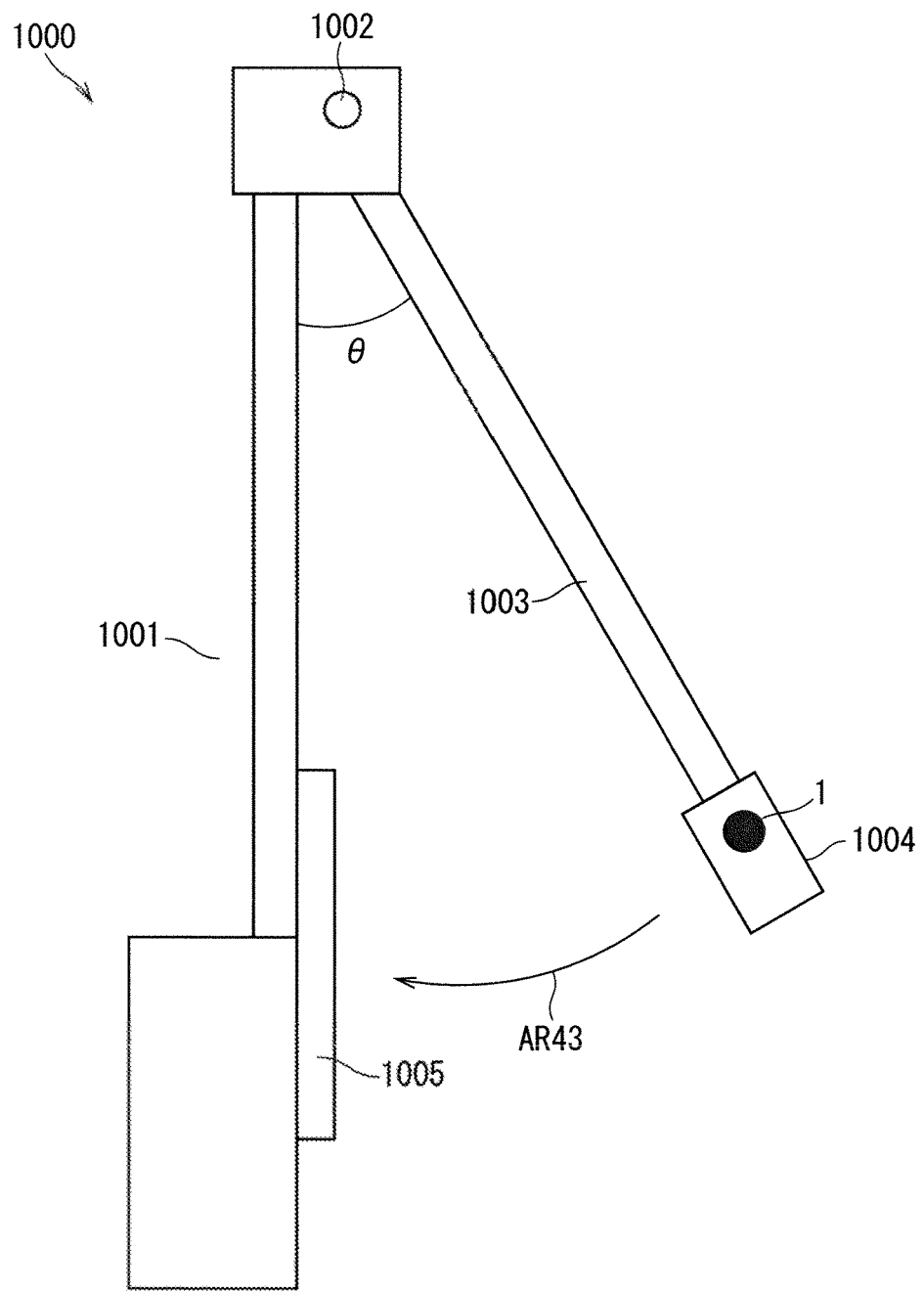
FIG. 31 is a view exemplifying a structure of an impact test apparatus 1000 of the assembled body 40.

FIG. 31 is a view exemplifying a structure of an impact test apparatus 1000 for the assembled body 40. The impact test apparatus 1000 includes a support shaft 1001 extending in the vertical direction, an arm part 1003 pivoting in a vertical plane around a pivoting center 1002 located in an upper end portion of the support shaft 1001, an attachment part 1004, to which the gas sensor 1 is attached, provided in an end portion opposite to the pivoting center 1002 in the arm part 1003, and a resin plate 1005 attached to the support shaft 1001 to abut to the attachment part 1004 when the attachment part 1004 is located in a lowermost end portion in the vertical plane.

More specifically, the assembled body 40 is attached to the attachment part 1004 in such a posture that the longitudinal direction of the assembled body 40 is perpendicular to the vertical plane in which the arm part 1003 pivots, with the bolt portion 3a being screwed with the attachment part 1004.

FIG. 32 is a view exemplifying a result of an impact test performed using the impact test apparatus 1000. The detail of the impact test is as follows.

(1) The arm part 1003 in which the assembled body 40 is attached to the attachment part 1004 is temporarily held to have an angle θ with respect to the vertical direction.

(2) When the above held state is released, the attachment part 1004 pivots as indicated by an arrow AR43 and collides with the resin plate 1005.

(3) Confirmed is whether or not the sensor element 10 is broken in the assembled body 40 after the collision.

(4) The processes of (1) to (3) are repeatedly performed on the assembled body 40 in which the sensor element 10 has not been broken, with a larger angle θ.

A default value of the angle θ was set to 50° and an incremental value of the angle θ was set to 10°. A pivoting radius of the arm part 1003 was 1217 mm, and the resin plate 1005 was made of polyacetal.

FIG. 32 shows a relationship between the angle (θ) provided to the sensor element 10 and a ratio (an occurrence rate) of the sensor element 10 which is broken at the angle for each of three levels, that is, $0 \leq X < 0.1$ mm, $0.1$ mm $\leq X < 0.2$ mm, and $0.2 \leq X < 0.3$ mm as the washer inclination amount (X) in the assembled body 40 being subject to the test. As can be seen from FIG. 32, the sensor element 10 tends to be broken as the washer inclination amount gets large as 0.2 mm or more. The result indicates that the washer inclination inspection process has a technical significance. The assembled body 40 in which the defect occurs as exemplified in FIGS. 14B and 14C can be reliably excluded by performing the washer inclination inspection process.

In the meanwhile, the continuity inspection process is performed in order to reliably exclude the assembled body 40 in which the breakage failure of the element occurs from the manufacturing object of the gas sensor 1. Because the conduction between the heater 70 and the electrode terminal 13 cannot be obtained in the broken sensor element 10, the assembled body 40 in which the breakage failure of the element occurs can be reliably excluded.

Figure 33:
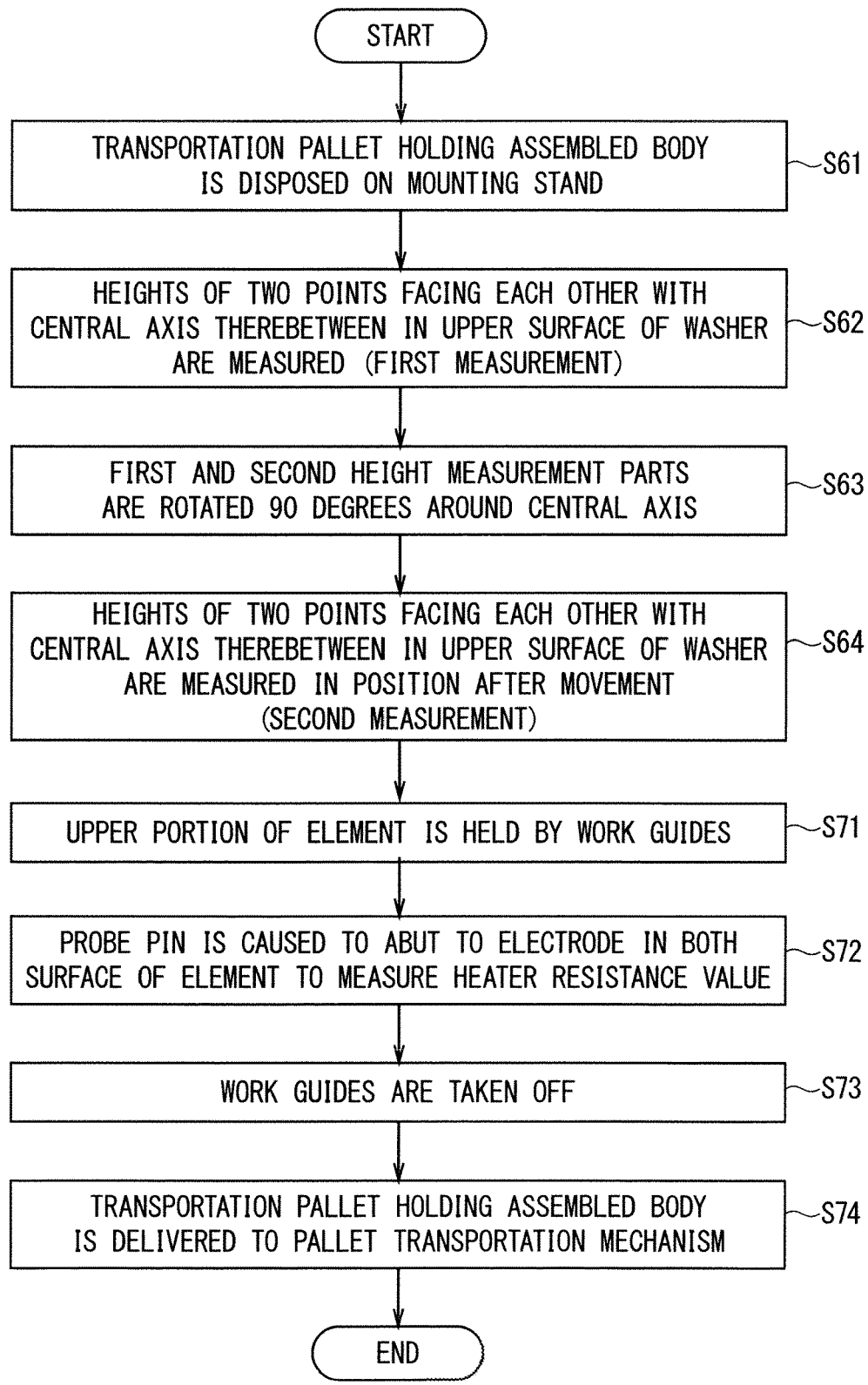
FIG. 33 is a view illustrating a more specific procedure of a washer inclination inspection process and a subsequent continuity inspection process.
Figure 34:
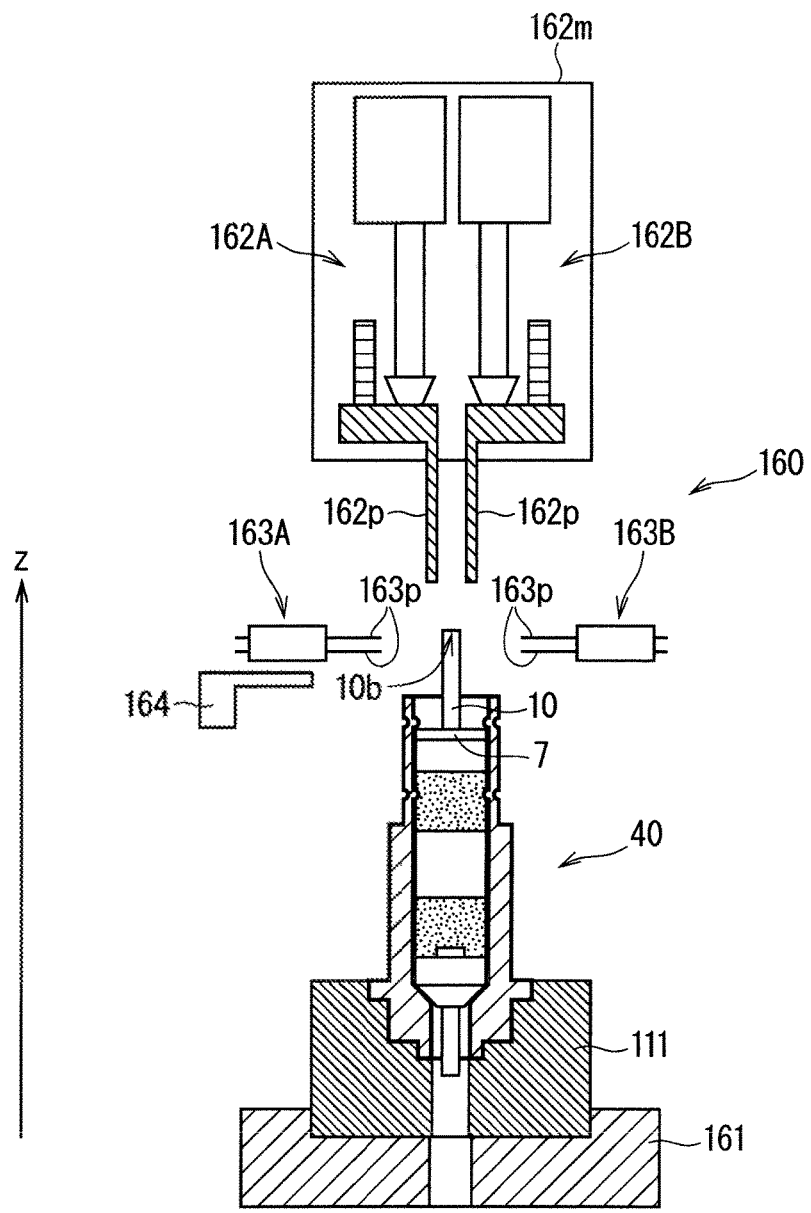
FIG. 34 is a side view schematically illustrating a structure of an inspection processing part 160.
Figure 35A:
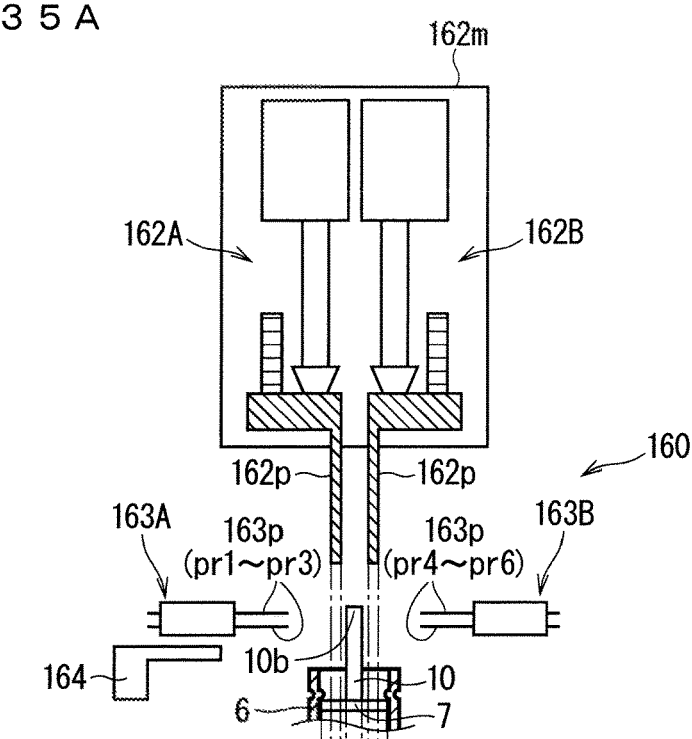
FIGS. 35A and 35B are views more specifically illustrating a positional relationship of constituent elements of the inspection processing part 160 at a time of starting the inspection process.
Figure 35B:
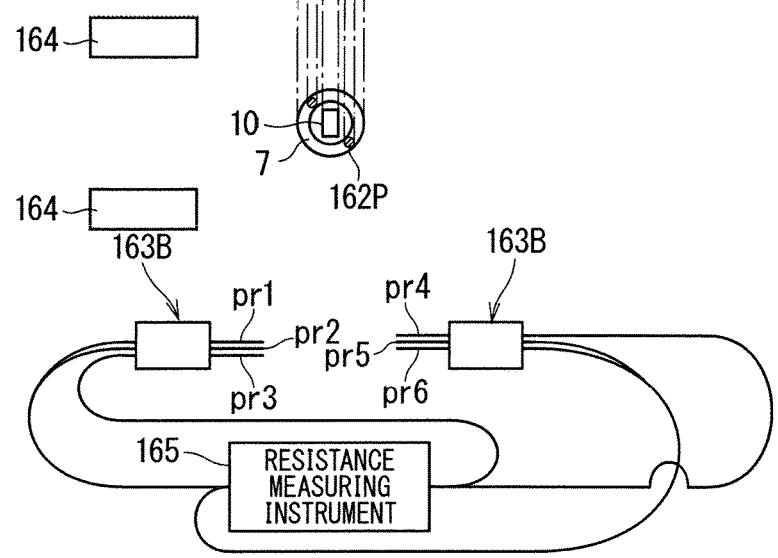
Figure 37:
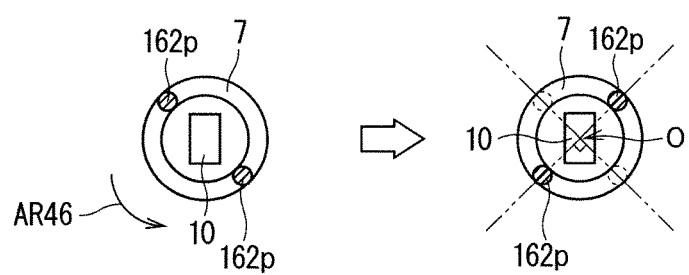
FIG. 37 is a view illustrating a state halfway through the washer inclination inspection process.
Figure 38C:
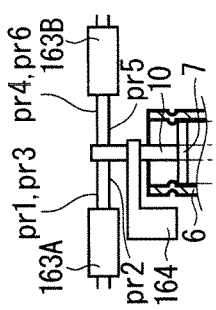
FIGS. 38A to 38C are views illustrating a state halfway through the continuity inspection process in stages.
Figure 38B:
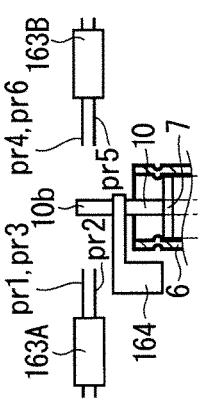
Figure 38A:
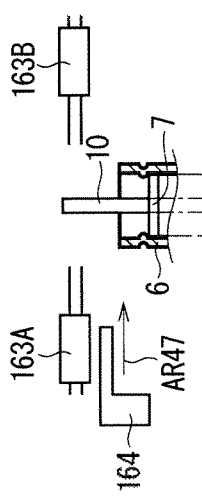
Figure 39A:
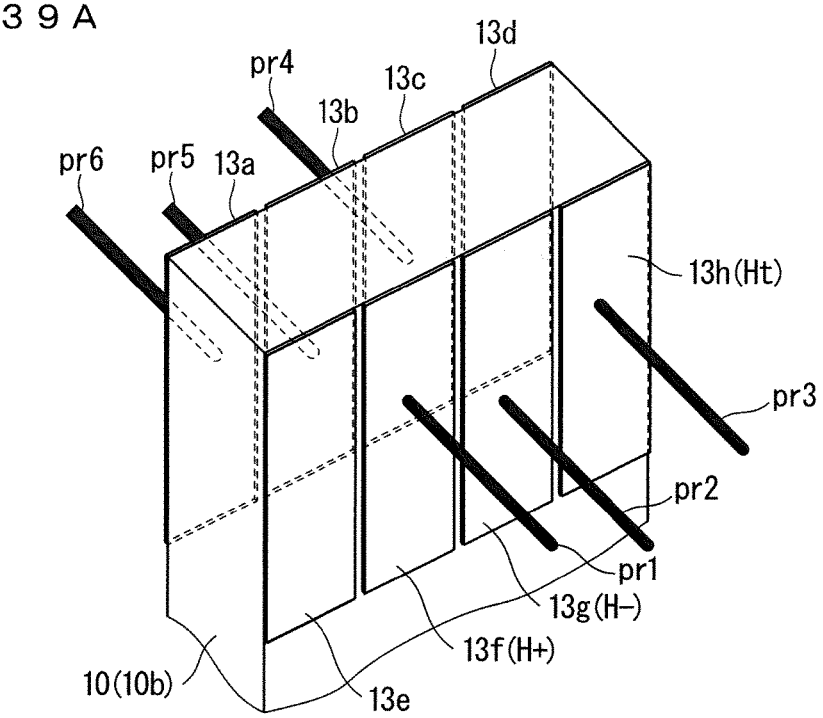
FIGS. 39A and 39B are views illustrating a relationship between a direction of the sensor element 10 and an object with which each probe pin of a first conduction measurement part 163A and second conduction measurement part 163B is abutted in the continuity inspection process.
Figure 39B:
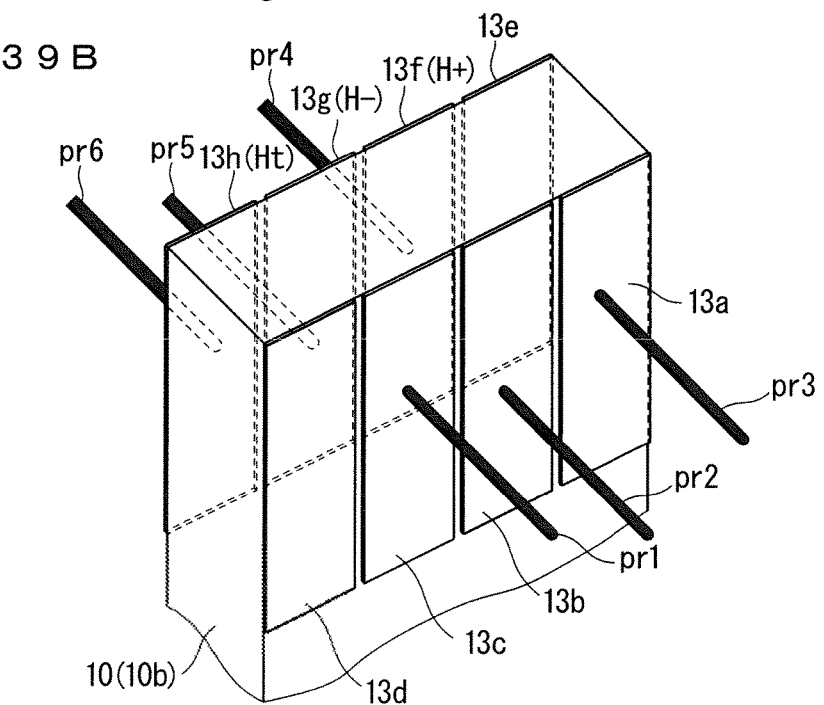

FIG. 33 is a view illustrating a more specific procedure of the washer inclination inspection process and the subsequent continuity inspection process performed in the inspection processing part 160. FIG. 34 is a side view (a partial cross-sectional view) schematically illustrating a structure of the inspection processing part 160. FIGS. 35A and 35B are views more specifically illustrating a positional relationship of constituent elements of the inspection processing part 160 at a time of starting the inspection process. Specifically, FIG. 35A is a partial view of FIG. 34, and FIG. 35B is a planar view of a main part corresponding to the partial view of FIG. 34. FIGS. 36 and 37 are views illustrating a state halfway through the washer inclination inspection process. FIGS. 38A to 38C are views illustrating a state halfway through the continuity inspection process in stages. FIGS. 39A and 39B are views illustrating a relationship between a direction of the sensor element 10 and an abutting target to which each probe pin of the first conduction measurement part 163A and second conduction measurement part 163B is abutted in the continuity inspection process.

The inspection processing part 160 mainly includes the pallet mounting stand 161, the first height measurement part 162A, the second height measurement part 162B, the first conduction measurement part 163A, the second conduction measurement part 163B, and a pair of work guides 164.

FIG. 34 illustrates a state where the transportation pallet 111 holding (placing and fixing) the assembled body 40 is disposed on the pallet mounting stand 161. FIG. 34 also illustrates, in a manner similar to FIG. 10, a state where the assembled body 40 is disposed and fixed in the assembly posture, in which the thickness direction of the sensor element 10 coincides to the horizontal direction of FIG. 34. The state where the transportation pallet 111 to which the assembled body 40 is placed and fixed is disposed on and fixed to the pallet mounting stand 161 is also referred to simply as a state where the assembled body 40 is fixed to the pallet mounting stand 161.

The pallet mounting stand 161 has a configuration similar to the pallet mounting stand 131 included in the tentative sealing processing part 130.

As shown in FIG. 34, the first height measurement part 162A and the second height measurement part 162B are provided above the pallet mounting stand 161 so that they can be integrally elevated and rotated in the horizontal plane by the height measurement part drive mechanism 162m. Each of the first height measurement part 162A and the second height measurement part 162B is a dial gauge or a digital gauge, for example, and has a probe 162p extending vertically downward. The first height measurement part 162A and the second height measurement part 162B are integrally lowered by the height measurement part drive mechanism 162m, so that heights of two different positions in the upper surfaces of the washer 7 can be measured at the same time with the probe 162p provided in each of the first height measurement part 162A and the second height measurement part 162B being abutted to those positions.

More specifically, as exemplified in FIG. 35B, the two probes 162p in the first height measurement part 162A and the second height measurement part 162B are disposed to be located above two points opposing to each other with a central axis therebetween in the upper surface of the washer 7, so that the heights of the two points can be measured at the same time.

In the inspection processing part 160, the height measurement part drive mechanism 162m integrally rotates the first height measurement part 162A and the second height measurement part 162B in the horizontal plane, so that an array direction of the probes 162p provided in the first height measurement part 162A and the second height measurement part 162B can be changed. Accordingly, the inspection processing part 160 can measure heights of four different positions or more in the upper surface of the washer 7.

Each of the first conduction measurement part 163A and the second conduction measurement part 163B has three probe pins 163p as shown in FIG. 35B. With these probe pins 163p being abutted to the predetermined electrode terminal 13 of the sensor element 10, the continuity inspection is performed. However, the first conduction measurement part 163A and the second conduction measurement part 163B stand by in a lateral position of the assembled body 40 until the continuity inspection process comes to be performed, as shown in FIGS. 35A and 35B.

The three probe pins 163p provided in the first conduction measurement part 163A are also referred to as probe pins pr1, pr2, and pr3 from a central portion toward an end portion in this order in planar view. The three probe pins 163p included in the second conduction measurement part 163B are also referred to as probe pins pr4, pr5, and pr6 from the central portion toward the end portion in this order in planar view.

Only the probe pin pr2 in the three probe pins 163p provided in the first conduction measurement part 163A is disposed in a height position different from the other two probe pins. That is to say, the probe pins pr1 to pr3 are disposed so that those tip portions are not located in the same straight line, in other words, a line segment connecting the tip portions forms a triangle. In the similar manner, only the probe pin pr5 in the three probe pins 163p provided in the second conduction measurement part 163B is disposed in a height position different from the other two probe pins. That is to say, also the probe pins pr4 to pr6 are disposed so that those tip portions are not located in the same straight line, in other words, a line segment connecting the tip portions forms a triangle. The above arrangement has an effect of enhancing stability in an abutting state where the probe pins 163p abut to the sensor element 10 compared with a case where the tip portions of the three probe pins 163p are arranged in the same straight line.

As schematically shown in FIG. 35B, the probe pins pr1 and pr2 of the first conduction measurement part 163A and the probe pins pr4 and pr5 of the second conduction measurement part 163B are electrically connected to one electrode of the resistance measuring instrument 165, and the probe pin pr3 of the first conduction measurement part 163A and the probe pin pr6 of the second conduction measurement part 163B are electrically connected to the other electrode of the resistance measuring instrument 165.

The pair of work guides 164 is provided to abut to the sensor element 10 from both side of the sensor element 10 at the time of the continuity inspection, thereby holding and fixing the sensor element 10. The pair of work guides 164, in a manner similar to the first conduction measurement part 163A and the second conduction measurement part 163B, also stand by in a lateral position of the assembled body 40 as shown in FIGS. 35A and 35B until the continuity inspection process comes to be performed.

In performing the washer inclination inspection process and the subsequent continuity inspection process in the inspection processing part 160, firstly, the transportation pallet 111, which has been delivered from the retightening processing part 150 in the fourth delivery position Pos4 and holds (places and fixes) the assembled body 40, is disposed in the fifth delivery position Pos5 by the pallet movement mechanism 112, and then, the transportation pallet 111 is disposed on and fixed to the pallet mounting stand 161 in the inspection processing part 160 together with the assembled body 40, by the pallet delivery mechanism 113, as shown in FIG. 34 (a step S61).

After the transportation pallet 111 is disposed and fixed as described above, heights of two points opposing to each other with the central axis therebetween in the upper surface of the washer 7 (making 180-degree angle with each other in the circumferential direction of the washer 7) are measured by the first height measurement part 162A and the second height measurement part 162B (a first measurement) (a step S62).

Figure 36A:
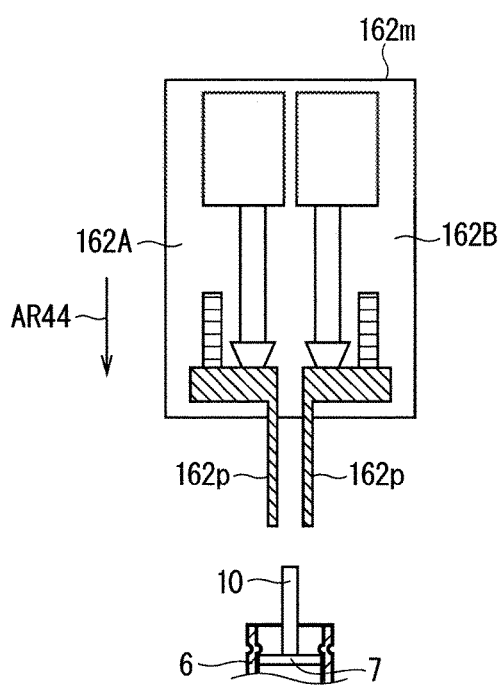
FIGS. 36A and 36B are views illustrating a state halfway through the washer inclination inspection process.

Specifically, under the state that the two probes 162p provided in each of the first height measurement part 162A and the second height measurement part 162B are located above two points opposing to each other with the central axis therebetween in the upper surface of the washer 7 as shown in FIG. 35B, the height measurement part drive mechanism 162m lowers the first height measurement part 162A and the second height measurement part 162B vertically downward as indicated by an arrow AR44 in FIG. 36A, thereby causing each probe 162p to abut to the upper surface of the washer 7.

The height position of the tip portion of each probe 162p in the abutting state is obtained as a measurement value in the first height measurement part 162A and the second height measurement part 162B in the first measurement. Each measurement value is provided to the inclination determination part 105.

The heights of the four points in the washer 7 making 90-degree angle with each other in the circumferential direction need to be measured to obtain the inclination amount for the determination target in the washer inclination inspection process, and in the first measurement described above, the measurement at the two points opposing to each other with the sensor element 10 therebetween among such four points is achieved.

Figure 36B:
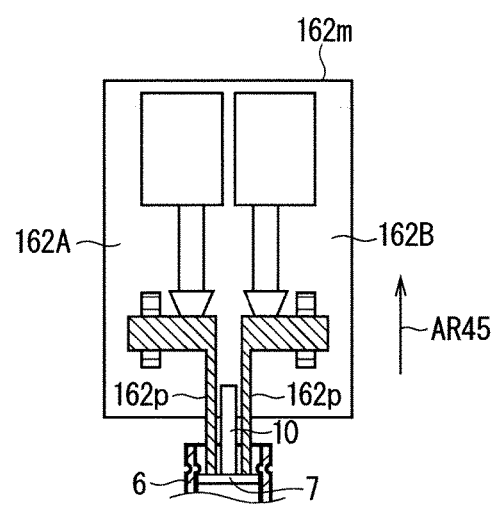

After the first measurement is completed, the height measurement part drive mechanism 162m temporarily raises the first height measurement part 162A and the second height measurement part 162B vertically upward as indicated by an arrow AR45 in FIG. 36B to separate the probes 162p from the washer 7. Subsequently, the height measurement part drive mechanism 162m rotates the first height measurement part 162A and the second height measurement part 162B 90 degrees around a central axis O of the washer 7 (a step S63).

Accordingly, as indicated by an arrow AR46 in FIG. 37, the position of each probe 162p of the first height measurement part 162A and the second height measurement part 162B rotates 90 degrees around the central axis O of the washer 7.

After the rotational movement is performed, a height measurement (a second measurement) is performed on two points opposing to each other with the central axis therebetween in the upper surface of the washer 7 (facing each other in a direction perpendicular to the array direction of the probes 162p in the first measurement), in a manner similar to the above first measurement, by the first height measurement part 162A and the second height measurement part 162B at the position after the movement (a step S64). The measurement values in the first height measurement part 162A and the second height measurement part 162B at this time are also provided to the inclination determination part 105.

After the second measurement is completed, the height measurement part drive mechanism 162m raises the first height measurement part 162A and the second height measurement part 162B vertically upward as indicated by the arrow AR45 in FIG. 36B to separate the probes 162p from the washer 7. The washer inclination inspection process is thereby finished.

In the case that the first measurement is performed under the state that the array direction of the two probes 162p in the horizontal plane is inclined with respect to the sensor element 10, the second measurement is also performed under the state that the array direction of the two probes 162p in the horizontal plane is inclined with respect to the sensor element 10. This manner is preferable in that interference between a protruding part inside the inner tube 6 caused by providing the concave portions 6a from the four side of the outer periphery and the probe 162p descending at the time of the inclination measurement is prevented, so that the probe 162p can be reliably caused to abut to the washer 7.

After the washer inclination inspection process is finished, the continuity inspection process is subsequently performed. Firstly, the work guide movement mechanism 164m not shown in FIGS. 38A to 38C moves the pair of work guides 164 in the standby state as indicated by arrows AR47 and AR48 in FIG. 38A, thereby causing the pair of work guides 164 to hold a portion near the second tip portion 10b of the sensor element 10, as shown in FIG. 38B (a step S71).

After the work guides 164 hold the sensor element 10, the conduction measurement part drive mechanism 163m not shown in FIGS. 38A to 38C moves the first conduction measurement part 163A and the second conduction measurement part 163B, which are also in the standby state, as indicated by an arrow AR49 in FIG. 38B. Subsequently, as shown in FIG. 38C, each probe pin 163p (pr1 to pr3 and pr4 to pr6) are caused to abut to the electrode terminal 13 provided in the two main surfaces P1 of the sensor element 10 to measure the resistance value (the heater resistance value) $R_H$ of the heater 70 (a step S72).

However, there are two ways to abut the probe pins pr1 to pr3 provided in the first conduction measurement part 163A and probe pins p4 to p6 provided in the second conduction measurement part 163B, as shown in FIGS. 39A and 39B, in accordance with the direction of the sensor element 10 in the assembled body 40, therefore, only one of the first conduction measurement part 163A and the second conduction measurement part 163B actually contributes to the measurement (calculation) of the heater resistance value $R_H$.

For example, in the case shown in FIG. 39A, the probe pins pr1, pr2, and pr3 provided in the first conduction measurement part 163A abut to the electrode terminals 13f (H+ electrode), 13g (H− electrode), and 13h (Ht electrode), respectively, so that the first conduction measurement part 163A contributes to the measurement (calculation) of the heater resistance value $R_H$.

In contrast, in the case shown in FIG. 39B, the probe pins pr4, pr5, and pr6 provided in the second conduction measurement part 163B abut to the electrode terminals 13f (H+ electrode), 13g (H− electrode), and 13h (Ht electrode), respectively, so that the second conduction measurement part 163B contributes to the measurement (calculation) of the heater resistance value $R_H$.

As described above, the reason why there are the two ways in combination of the probe pin 163p and the electrode terminal 13 to which the probe pin 163p abuts in this preferred embodiment is that, although the electrode terminals 13f (H+ electrode), 13g (H− electrode), and 13h (Ht electrode) used for calculating the heater resistance value $R_H$ are provided in only one of the two main surfaces P1 (P1a and P1b) of the sensor element 10 (the main surface P1b in the case of FIGS. 3A to 3C), the two main surfaces P1*a* and P1*b* are especially not distinguished in the sequential processes described above, so that it varies depending on the individual assembled body 40 which of the first conduction measurement part 163A and the second conduction measurement part 163B the main surfaces P1*a* and P1*b* are directed to, respectively.

Therefore, the abutting of each probe pin 163*p* of the first conduction measurement part 163A and the second conduction measurement part 163B according to the manner shown in FIG. 38C means that the probe pins 163*p* are concurrently abutted to the plurality of electrode terminals 13 which may correspond to the heater electrode terminals, regardless of which of the manner shown in FIG. 39A or 39B is achieved.

However, as shown in FIG. 35B, since the probe pins which come to be abutted the same electrode terminal are connected to the same electrode of the resistance measuring instrument 165, the heater resistance value $R_H$ of the sensor element 10 can be obtained by the resistance measuring instrument 165 regardless of which of the first conduction measurement part 163A and the second conduction measurement part 163B contributes the actual measurement. In other words, in this preferred embodiment, the heater resistance value $R_H$ can be obtained by one measurement operation regardless of the direction of the heater electrode terminals 13 (13*f* (H+ electrode), 13*g* (H− electrode), and 13*h* (Ht electrode)).

According to the above configuration of connection, the heater resistance value $R_H$ can be obtained without specifying the direction of the sensor element 10, so that the above configuration of connection is deemed to contribute to the improvement of the productivity of the gas sensor 1.

The obtained heater resistance value $R_H$ is provided from the resistance measuring instrument 165 to the conduction determination part 106. To be exact, a resistance value $R_1$ between the H+ electrode and the Ht electrode and a resistance value $R_2$ between the H− electrode and the Ht electrode are directly measured by the resistance measuring instrument 165, and the heater resistance value $R_H$ is the value calculated from the equation (1) described above.

Since the resistance values $R_1$ and $R_2$ reach an infinite value at the side of the probe pin 163*p* being abutted to the electrode terminal 13 which is not the heater electrode terminal, the value of the heater resistance value $R_H$ cannot be obtained.

As shown in FIGS. 39A and 39B, either one of the first conduction measurement part 163A and second conduction measurement part 163B does not contribute to the measurement of the heater resistance value $R_H$. However, the manner of causing the first conduction measurement part 163A and second conduction measurement part 163B to abut to the sensor element 10 from its both sides as described above brings the effect that the state where the probe pins 163*p* undertaking the measurement of the heater resistance value $R_H$ abut to the sensor element 10 (more specifically, the H+ electrode, the H− electrode, and the Ht electrode) is stabilized by causing the probe pins 163*p* not undertaking the measurement to support the opposite side of the sensor element 10. It can be said that the probe pins 163*p* not contributing to the measurement of the heater resistance value $R_H$ in the first conduction measurement part 163A and second conduction measurement part 163B also function as a supporting member for stabilizing the state where the probe pins 163*p* contributing to the measurement of the heater resistance value $R_H$ abut to the electrode terminal, including the fact described above that the height positions of the probe pins pr2 and pr5 are different from those of the other probe pins 163*p*.

After the heater resistance value $R_H$ is obtained by the resistance measuring instrument 165, the abutting of the probe pins 163*p* is dissolved, and subsequently, the work guides 164 are also taken off to the default standby position (a step S73).

After the work guides 164 are taken off, the transportation pallet 111 holding the assembled body 40 is delivered from the pallet mounting stand 161 to the pallet movement mechanism 112 by the pallet deliver mechanism 113 (a step S74). That is to say, the transportation pallet 111 is disposed in the fifth deliver position Pos5 again. The inspection process is thereby finished.

<Determination of Inspection Result>

After the inspection process is finished, a determination processing based on an inspection result in the washer inclination inspection process and the continuity inspection process is performed for the individual assembled body 40.

Firstly, the inclination determination part 105 performs the inclination determination processing. Specifically, the inclination determination part 105 specifies a maximum value and a minimum value in the values of the heights in the four points in the washer 7 obtained by the first measurement and the second measurement in the washer inclination inspection process, thereafter to calculate the washer inclination amount as the difference value between the maximum value and the minimum value. Subsequently, the inclination determination part 105 compares the washer inclination amount and a predetermined threshold value, and determines that the assembled body 40 has passed the washer inclination inspection when the washer inclination amount is smaller than the threshold value (YES in the step S8).

For example, when the impact test result shown in FIG. 32 is obtained in advance, it is considered to be preferable that the threshold value of the washer inclination amount is set to 0.2 mm.

Subsequently, the conduction determination part 106 performs the conduction determination processing for the assembled body 40 which has passed the washer inclination inspection. Specifically, the heater resistance value $R_H$ measured in the continuity inspection process for the sensor element 10 included in the assembled body 40 is compared with the predetermined threshold value, and when the heater resistance value $R_H$ is smaller than the threshold value, the conduction determination part 106 determines that the assembled body 40 has passed the continuity inspection (YES in the step S9). The result that the heater resistance value $R_H$ is larger than the threshold value indicates that the conduction is not sufficiently secured in the sensor element 10. It is likely that the breakage failure of the element occurs in the assembled body 40 for which such a result is obtained in the conduction determination processing.

The assembled body 40 which has passed both the inclination determination processing and the continuity inspection processing is the OK product (the non-defective product), so that it is delivered to the assembled body standby part 170 so as to be provided to the process in the subsequent stages.

In the meanwhile, the assembled body 40 which is rejected in the inclination determination processing by reason that the washer inclination amount exceeds the predetermined threshold value (NO in the step S8) and the assembled body 40 which is rejected in the continuity inspection processing by reason that the heater resistance value $R_H$ is larger than the predetermined threshold value (NO in the step S9) are the NG product (the defective product), so that they are discarded without being provided to the process in the subsequent stages.

As described above, in this preferred embodiment, since the inclination or displacement of the sensor element 10 is limited with the usage of the element constraining jig 133 at the time of the hermetic sealing of the assembled body 40, the ratio of the breakage failure of the element in the assembled body 40 is sufficiently reduced in the first place. However, performing the inspection process described above thereby to exclude the defective product enables that the defect of the gas sensor 1 caused by the breakage of the sensor element 10 is almost certainly prevented.

As described above, according to this preferred embodiment, the range of inclination or displacement of the sensor element is constrained by the element constraining jig at the time of the tentative sealing for fixing the sensor element with the powder compact performed in the process of manufacturing the assembled body constituting the main body of the gas sensor, so that the occurrence of the breakage failure of the element inside the assembled body can be appropriately suppressed.

Moreover, the washer inclination inspection process is performed after completing the assembled body, so that the usage of the assembled body having the breakage failure of the element due to the washer inclination or holding a potential of having it in the future, to the gas sensor can be appropriately prevented.

Furthermore, the washer continuity inspection process is performed after completing the assembled body, so that the usage of the assembled body having the breakage failure of the element to the gas sensor can be appropriately prevented.

In addition, the continuity inspection process is performed subsequent to the washer inclination inspection process, so that the usage of the assembled body having the breakage failure of the element or holding a potential of having it in the future to the gas sensor can be almost certainly prevented. However, both the washer inclination inspection process and the continuity inspection process are not necessary, but only one of them may be performed as long as the usage of the assembled body having the breakage failure of the element to the gas sensor is sufficiently suppressed.

The invention claimed is:

1. A method for manufacturing a gas sensor, said method including a step of obtaining an assembled body constituting said gas sensor by performing a predetermined processing on a semi-assembled body which is manufactured in advance, wherein said semi-assembled body comprises:
an annular-mounted assembly in which a plurality of annularly-mounted members each having a disc shape or cylindrical shape are annularly mounted around a sensor element with an elongated plate shape comprising a ceramic, the plurality of annularly-mounted members including at least a first ceramic powder compact located on one end side of said sensor element and a second ceramic powder compact located on an other end side of said sensor element opposite said one end side of said sensor element: and
a tubular body which is annularly mounted to an outer periphery of said annularly-mounted members and capable of engaging said one end side of said annularly-mounted members therein, and
said step of obtaining said assembled body comprising steps of:
a) causing said one end side of said sensor element constituting said semi-assembled body to abut to a predetermined positioning member for positioning said sensor element with respect to said semi-assembled body; and
b) applying a first force to said annularly-mounted members from said other end side of said sensor element having been positioned through said step a) and thereby compressing said first powder compact and said second powder compact so as to fix said sensor element inside of said tubular body, wherein
said step b) is performed while constraining said sensor element in a predetermined constraining region in said other end side of said sensor element.

2. The method for manufacturing said gas sensor according to claim 1,
said step b) comprising a step of:
b-1) forming said constraining region with a pair of constraining jigs, wherein
said first powder compact and said second powder compact are compressed after said constraining region is formed in said step b-1).

3. The method for manufacturing said gas sensor according to claim 2, wherein
in said step b-1), said constraining region is formed with said pair of constraining jigs being disposed at a predetermined distance from each other in a direction along a longitudinal direction of said sensor element.

4. The method for manufacturing said gas sensor according to claim 2, wherein
said plurality of annularly-mounted members include a plurality of ceramic insulators and
in said step b-1), a clearance between said pair of constraining jigs and said sensor element is equal to or smaller than a maximum value of a gap between one of said plurality of ceramic insulators, which is closest to said constraining region in said plurality of ceramic insulators, and said sensor element.

5. The method for manufacturing said gas sensor according to claim 1,
said step of obtaining said assembled body further comprising a step of:
c) after said step b), applying a second force which is larger than said first force to said annularly-mounted members from said other end side of said sensor element with said one end side of said sensor element not abutting to any positioning member including said positioning member such that a position of said sensor element is not fixed when applying the second force and thereby further compressing said first powder compact and said second powder compact so as to hermetically seal between spaces located on said one end side and said other end side of said sensor element inside of said tubular body.

6. The method for manufacturing said gas sensor according to claim 5, wherein
a posture of each of said semi-assembled body and said assembled body in which a longitudinal direction of said sensor element extends in a vertical direction and said other end side is located in an upper side is defined as an assembly posture of each of said semi-assembled body and said assembled body,
said step a) is a step of causing said positioning member to abut to said one end side of said sensor element from a lower side of said sensor element with said semi-assembled body being in said assembly posture,
in said step b), said first force is applied to an upper portion of said annularly-mounted members as a vertically downward force under a state that said semi-assembled body is in said assembly posture and said sensor element has been positioned through said step a), so that said first powder compact and second powder compact are compressed, and said sensor element is fixed in a first position depending on a position of said positioning member by said compressed first powder compact and said compressed second powder compact, and in said step c), said second force is applied to said upper portion of said annularly-mounted members in said state where said semi-assembled body is in said assembly posture.

7. The method for manufacturing said gas sensor according to claim 6, wherein said sensor element is displaced from said first position to a second position in a vertical direction through said step c), and said positioning member is disposed in said step a) so that said second position is located within a predetermined range which is determined in advance as a position of said sensor element in said assembled body.

8. The method for manufacturing said gas sensor according to claim 7, wherein in said step a), said positioning member is disposed so that said second position is located within said predetermined range which is determined based on a correlation between said first position and said second position of said sensor element, said correlation being specified in advance.

9. The method for manufacturing said gas sensor according to claim 6, said annularly-mounted members including a washer, and the method further comprising steps of:

f) obtaining an inclination amount of said washer in a state where said assembled body is in said assembly posture; and g) determining that said assembled body is a defective product when said inclination amount exceeds a predetermined threshold value.

10. The method for manufacturing said gas sensor according to claim 9, wherein in said step f), a difference value between a maximum value and a minimum value in the values of heights in four points in said washer making 90-degree angle with each other in a circumferential direction is obtained as said inclination amount.

11. The method for manufacturing said gas sensor according to claim 10, said step f) comprising steps of:

f-1) measuring height positions of two points opposing to each other with said sensor element therebetween in said four points by two height measurement elements at a time; and f-2) measuring height positions of remaining two points which have not been measured in said step f-1) in said four points by said two height measurement elements at a time, and said inclination amount is calculated based on a measurement result in said step f-1) and said step f-2).

12. The method for manufacturing said gas sensor according to claim 6, said sensor element including a heater made up of a resistance heater therein, a plurality of heater electrode terminals being electrically connected to said heater in said other end side, and the method further comprising steps of:

h) measuring a resistance value of said heater via said plurality of heater electrode terminals of said sensor element included in said assembled body; and i) determining that said assembled body is a defective product when said resistance value of said heater obtained in said step h) exceeds a predetermined threshold value.

13. The method for manufacturing said gas sensor according to claim 12, wherein said plurality of heater electrode terminals are provided only in one of two main surfaces opposing to each other of said sensor element, and in said step h), while probe pins for measurement are abutted to a plurality of electrode terminals which may correspond to said plurality of heater electrode terminals included in each of said two main surfaces with said assembled body being in said assembly posture, said resistance value of said heater is measured via electrode terminals which actually correspond to said plurality of heater electrode terminals in said plurality of electrode terminals.

14. The method for manufacturing said gas sensor according to claim 13, wherein said plurality of heater electrode terminals are three electrode terminals, and in said step h), three probe pins for measurement, whose end portions are not located in an identical straight line, are prepared for each side of said two main surfaces, and each of said three probe pins for measurement are abutted to either of said three electrode terminals which may correspond to said plurality of heater electrode terminals in each side of said two main surfaces.

15. The method for manufacturing said gas sensor according to claim 5, said step of obtaining said assembled body further comprising a step of:

d) swaging said tubular body, in said state where said semi-assembled body is in an assembly posture, with a first swaging element from an outer periphery thereof, in a first swaging position which is located above an uppermost portion of said annularly-mounted members whose first powder compact and second powder compact have been compressed in said step c).

16. The method for manufacturing said gas sensor according to claim 15, wherein said step d) is successively performed subsequent to said step c) with said second force being kept to apply to said upper portion of said annularly-mounted members.

17. The method for manufacturing said gas sensor according to claim 15, said step of obtaining said assembled body further comprising a step of:

e) swaging said tubular body, in said state where said semi-assembled body is in said-assembly posture, with a second swaging element from an outer periphery thereof, in a second swaging position which is located in a lateral position of said second powder compact after said step d).

18. A gas sensor manufacturing apparatus, said apparatus including at least an element for obtaining an assembled body constituting said gas sensor by performing a predetermined processing on a-semi-assembled body which is manufactured in advance, wherein said semi-assembled body comprises:

an annular-mounted assembly in which a plurality of annularly-mounted members each having a disc shape or cylindrical shape are annularly mounted around a sensor element with an elongated plate shape comprising a ceramic, the plurality of annularly-mounted members including at least a first ceramic powder compact located on one end side of said sensor element and a second ceramic powder compact located on an other end side of said sensor element opposite said one end side of said sensor element; and a tubular body which is annularly mounted to an outer periphery of said annularly-mounted members and capable of engaging said one end side of said annularly-mounted members therein, and said element for obtaining said assembled body comprising:

a positioning member abutting to said one end side of said sensor element constituting said semi-assembled body for positioning said sensor element with respect to the semi-assembled body;

a first compression element applying a first force to said annularly-mounted members from an other end side of said sensor element which has been positioned by said positioning member and thereby performing a first compression of compressing said first powder compact and said second powder compact; and a constraining element capable of constraining said sensor element in a predetermined constraining region in said other end side of said sensor element, wherein said first compression element performs said first compression under a state that said constraining element constrains said sensor element in said constraining region n said other end side of said sensor element, thereafter to fix said sensor element inside said tubular body.

19. The gas sensor manufacturing apparatus according to claim 18, wherein said constraining element is a pair of constraining jigs, and each of said pair of constraining jigs are disposed at a predetermined distance from each other in a direction along a longitudinal direction of said sensor element at the time of forming said constraining region.

20. The gas sensor manufacturing apparatus according to claim 18, wherein said plurality of annularly-mounted members include a plurality of ceramic insulators, and said constraining region is formed so that a clearance between said constraining element and said sensor element is equal to or smaller than a maximum value of a gap between one of said plurality of insulators, which is closest to said constraining region in said plurality of insulators, and said sensor element.

21. The gas sensor manufacturing apparatus according to claim 18, said first compression element comprising:

a first compression jig abutting to said annularly-mounted members from said other end side of said sensor element to apply said first force, wherein said first compression jig abuts to said annularly-mounted members, thereby applying said first force, while housing therein said constraining element forming said constraining region.

22. The gas sensor manufacturing apparatus according to claim 18, said element for obtaining said assembled body further comprising:

a second compression element applying, after said first compression, a second force which is larger than said first force to said annularly-mounted members from said other end side of said sensor element with said one end side of said sensor element not abutting to any positioning member including said positioning member such that a position of said sensor element is not fixed when applying the second force and thereby performing a second compression of further compressing said first powder compact and said second powder compact, so as to hermetically seal between spaces located on said one end side and said other end side of said sensor element is performed inside of said tubular body.

23. The gas sensor manufacturing apparatus according to claim 22, wherein a posture of each of said semi-assembled body and said assembled body in which a longitudinal direction of said sensor element extends in a vertical direction and said other end side is located in an upper side is defined as an assembly posture of each of said semi-assembled body and said assembled body, said positioning member abuts to said one end side of said sensor element from a lower side of said sensor element with said semi-assembled body being in said assembly posture, in said first compression, said first force is applied to an upper portion of said annularly-mounted members as a vertically downward force under a state that said semi-assembled body is in said assembly posture and said sensor element has been positioned with said positioning member, so that said first powder compact and said second powder compact are compressed, and said sensor element is fixed in a first position depending on a position of said positioning member by said compressed first powder compact and said compressed second powder compact, and in said second compression, said second force is applied to said upper portion of said annularly-mounted members in said state where said semi-assembled body is in said assembly posture.

24. The gas sensor manufacturing apparatus according to claim 23, wherein said sensor element is displaced from said first position to a second position in a vertical direction through said second compression, and said positioning member is disposed so that said second position is located within a predetermined range which is determined in advance as a position of said sensor element in said assembled body.

25. The gas sensor manufacturing apparatus according to claim 24, wherein said positioning member is disposed so that said second position is located within said predetermined range which is determined based on a correlation between said first position and said second position of said sensor element, said correlation being specified in advance.

26. The gas sensor manufacturing apparatus according to claim 23, said annularly-mounted members including a washer, and the gas sensor manufacturing apparatus further comprising:

an inclination amount calculation element for obtaining an inclination amount of said washer in a state where said assembled body is in said assembly posture; and an inclination determination element for determining that said assembled body is a defective product when said inclination amount exceeds a predetermined threshold value.

27. The gas sensor manufacturing apparatus according to claim 26, wherein said inclination amount calculation element obtains a difference value between a maximum value and a minimum value in the values of heights in four points in said washer making 90-degree angle with each other in a circumferential direction as said inclination amount.

28. The gas sensor manufacturing apparatus according to claim 27, wherein
said inclination amount calculation element is configured to perform
a first measurement to measure height positions of two points opposing to each other with said sensor element therebetween in said four points by two height measurement elements at a time and
a second measurement to measure height positions of remaining two points which have not been measured in said first measurement in said four points by said two height measurement elements at a time,
thereby calculating said inclination amount based on a measurement result in said first measurement and said second measurement.

29. The gas sensor manufacturing apparatus according to claim 23,
said sensor element including a heater made up of a resistance heater therein, and
a plurality of heater electrode terminals being electrically connected to said heater in said other end side,
the gas sensor manufacturing apparatus further comprising:
a resistance measurement element measuring a resistance value of said heater via said plurality of heater electrode terminals of said sensor element included in said assembled body; and
a continuity determination element determining that said assembled body is a defective product when said resistance value of said heater obtained in said resistance measurement element exceeds a predetermined threshold value.

30. The gas sensor manufacturing apparatus according to claim 29, wherein
said plurality of heater electrode terminals are provided only in one of two main surfaces opposing to each other of said sensor element, and
said resistance measurement element makes probe pins for measurement abutted to a plurality of electrode terminals which may correspond to said plurality of heater electrode terminals included in each of said two main surfaces with said assembled body being in said assembly posture, and measures said resistance value of said heater via electrode terminals which actually correspond to said plurality of heater electrode terminals in said plurality of electrode terminals.

31. The gas sensor manufacturing apparatus according to claim 30, wherein
said plurality of heater electrode terminals are three electrode terminals, and
said resistance measurement element includes three probe pins for measurement, whose end portions are not located in an identical straight line, for each side of said two main surfaces, and causes each of said three probe pins for measurement to abut to either of said three electrode terminals which may correspond to plurality of heater electrode terminals in each side of said two main surfaces.

32. The gas sensor manufacturing apparatus according to claim 22,
said element for obtaining said assembled body further comprising:
a first swaging element performing a first swaging for swaging said tubular body, in said state where said semi-assembled body is in an assembly posture, from an outer periphery thereof, in a first swaging position which is located right above an uppermost portion of said annularly-mounted members whose first powder compact and second powder compact have been compressed by said second compression.

33. The gas sensor manufacturing apparatus according to claim 32, wherein
said first compression element performs said first swaging with said second compression element keeping to apply said second force to said upper portion of said annularly-mounted members.

34. The gas sensor manufacturing apparatus according to claim 32,
said element for obtaining said assembled body further comprising:
a second swaging element performing a second swaging for swaging said tubular body, in said state where said semi-assembled body is in said assembly posture, from an outer periphery thereof, in a second swaging position which is located in a lateral position of said second powder compact after said first swaging.

* * * * *